United States Patent
Shikada et al.

(10) Patent No.: US 6,562,306 B1
(45) Date of Patent: *May 13, 2003

(54) APPARATUS FOR PRODUCING DIMETHYL ETHER

(75) Inventors: Tsutomu Shikada, Fukuyama (JP); Takashi Ogawa, Yokohama (JP); Masatsugu Mizuguchi, Kunitachi (JP); Masami Ono, Yokohama (JP)

(73) Assignee: NKK Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/587,153

(22) Filed: Jun. 2, 2000

Related U.S. Application Data

(62) Division of application No. 08/847,347, filed on Apr. 24, 1997, now Pat. No. 6,147,125.

(30) Foreign Application Priority Data

| May 20, 1996 | (JP) | 8-124780 |
| May 21, 1996 | (JP) | 8-125370 |
| May 22, 1996 | (JP) | 8-126669 |
| May 13, 1996 | (JP) | 8-117243 |
| Dec. 19, 1996 | (JP) | 8-339758 |

(51) Int. Cl.[7] ............... B01J 23/90; B01J 8/00; B01J 35/02; C07C 27/00; C07C 27/06

(52) U.S. Cl. ........ 422/223; 422/211; 422/234; 422/187; 422/188; 518/700; 518/705; 518/706; 518/722; 518/728

(58) Field of Search .............. 422/211, 223, 422/234, 187, 188; 518/700, 705, 706, 722, 728

(56) References Cited

U.S. PATENT DOCUMENTS

| 2,256,622 A | * | 9/1941 | Murphree et al. ......... 422/191 |
| 4,098,809 A | | 7/1978 | Pagani |
| 4,375,424 A | | 3/1983 | Slaugh |
| 4,863,894 A | | 9/1989 | Chinchen et al. |
| 5,070,058 A | | 12/1991 | Sawicki et al. |
| 5,218,003 A | | 6/1993 | Lewnard et al. |
| 5,324,335 A | * | 6/1994 | Benham et al. .............. 44/452 |
| 5,389,689 A | | 2/1995 | Fujimoto et al. |
| 5,466,720 A | | 11/1995 | Fujimoto et al. |
| 5,753,716 A | * | 5/1998 | Peng et al. ................. 518/700 |
| 5,958,986 A | * | 9/1999 | Mart et al. ................. 518/709 |

FOREIGN PATENT DOCUMENTS

| EP | 324475 | 7/1989 |
| EP | 0 324 475 | 7/1989 |
| EP | 404408 | 12/1990 |
| EP | 0 409 086 | 1/1991 |
| EP | 409086 | 1/1991 |
| EP | 482753 | 4/1992 |
| EP | 483609 | 5/1992 |
| EP | 591538 | 4/1994 |
| GB | 2093365 | 9/1982 |
| GB | 2253623 | 9/1992 |
| JP | 2-9833 | 1/1990 |
| JP | 2-280836 | 11/1990 |
| JP | 3-52835 | 3/1991 |
| JP | 3-181435 | 8/1991 |
| JP | 4-264046 | 9/1992 |
| WO | WO 93/10069 | 5/1993 |

* cited by examiner

Primary Examiner—Glenn Caldarola
Assistant Examiner—Douglas W. Rudnick
(74) Attorney, Agent, or Firm—Frishauf, Holtz, Goodman & Chick, P.C.

(57) ABSTRACT

An apparatus for producing dimethyl ether comprising: a slurry-bed reactor filled with a dimethyl ether synthesis catalyst and a medium oil therefor; a condenser for condensing a gasified medium oil discharged from the reactor; an adsorber for removing a catalyst-deactivation ingredient from the medium oil condensed in the condenser; and recycle means for recycling the medium oil to the slurry-bed reactor.

8 Claims, 10 Drawing Sheets

REACTION PRESSURE 50atm
INITIAL H2/CO=1

REACTION PRESSURE 50atm
INITIAL H2/CO=1

APPARATUS FOR PRODUCING DIMETHYL ETHER

This is a division of application Ser. No. 08/847,347, filed Apr. 24, 1997, now U.S. Pat. No. 6,147,125.

BACKGROUND OF THE INVENTION

1. Field of the Invention

The present invention relates to a catalyst for dimethyl ether, a method for producing the catalyst, and a method for producing dimethyl ether by using the catalyst.

2. Description of the Related Arts

There are several known methods for manufacturing dimethyl ether starting from a mixed gas of carbon monoxide, carbon dioxide, and hydrogen under the presence of a catalyst suspended in a solvent.

For example, JP-A-2-9833 (the term "JP-A-" referred to herein signifies "Unexamined Japanese patent publication"), JP-A -3-181435, JP-A-3-52835, JP-A-4-264046, WO 93/10069 disclose methods for manufacturing dimethyl ether or a mixture of dimethyl ether and methanol through the contact of a synthesis gas with a mixture of a methanol synthesis catalyst and a methanol dehydration catalyst suspended in an inert liquid.

The method disclosed in JP-A-2-9833 is a method of direct synthesis of dimethyl ether from a synthesis gas, which method comprises the step of contacting a synthesis gas consisting of hydrogen, carbon monoxide and carbon dioxide with a solid catalyst, or reacting the synthesis gas react under the presence of the solid catalyst to conduct catalytic synthesis of dimethyl ether from the synthesis gas, wherein the synthesis gas undergoes catalytic action under the presence of the solid catalyst system, and wherein the solid catalyst is a single catalyst or a mixture of plurality of catalysts which are suspended in a liquid medium in a three-phase (slurry phase) reactor system, and wherein the three-phase reactor system comprises at least a single three-phase reactor.

The method disclosed in JP-A-3-181435 is a method for manufacturing dimethyl ether from a mixed gas of carbon monoxide and hydrogen, or a mixed gas of carbon monoxide and hydrogen and further containing carbon dioxide and/or water vapor, wherein a catalyst is used in a slurry form by suspension thereof in a solvent.

The method disclosed in JP-A-3-52835 is a method of dimethyl ether synthesis characterized in that a synthesis gas is reacted under the presence of a solid methanol synthesis catalyst to produce methanol, and that the produced methanol is reacted under the presence of a solid dehydration catalyst to produce dimethyl ether. According to the method, dimethyl ether is synthesized from a synthesis gas consisting of hydrogen, carbon monoxide, and carbon dioxide. That is, the synthesis gas is contacted with a solid catalyst system comprising a methanol-synthesizing ingredient and a dehydrating (ether-forming) ingredient, wherein the solid catalyst system is a single catalyst or a mixture of plurality of catalysts in a three-phase (liquid phase) reactor system, and wherein the reactor system is controlled to keep the minimum effective methanol rate to at least a level of 1.0 g-mole of methanol per 1 kg of catalyst per hour.

The method disclosed in WO 93/10069 is a method for manufacturing dimethyl ether from a mixed gas containing carbon monoxide and either or both of water and water vapor, or from a mixed gas containing carbon monoxide and either or both of water and water vapor and further containing carbon dioxide, wherein a catalyst is used in a form of solvent slurry, which catalyst is prepared by pulverizing a mixed catalyst containing at least zinc oxide and, copper oxide or chromium oxide, and aluminum oxide, by adhering these ingredients together under pressure, and by pulverizing them again to suspend in the solvent.

On the other hand, dimethyl ether is synthesized generally in a fixed bed system. There is a known catalyst for a fixed bed system, which catalyst is prepared by depositing a methanol synthesis catalyst onto a support of metallic oxide such as alumina, then by calcining them together. (JP-A-2-280386)

The methods for manufacturing dimethyl ether disclosed in JP-A-2-9833, JP-A-3-52835, JP-A-4-264046, and JP-A-3-181435, however, raise problems such that the two kinds of or three kinds of catalysts suspended in a solvent separate from each other in the reactor owing to the difference in specific gravity among the methanol synthesis catalyst, the methanol dehydration catalyst, and the water gas shift catalyst, which induces a distribution in catalyst concentration or deposition of one of these catalysts, thus significantly degrading the use efficiency of the catalysts.

The catalyst disclosed in WO 93/10069 is prepared by integrating the above-described three kinds of catalysts by means of a mechanical method. These types of catalysts also raise a problem, that during a period of use in a slurry state, the catalyst particles separate from each other to induce a distribution in catalyst concentration and catalyst deposition.

SUMMARY OF THE INVENTION

It is an object of the present invention to provide a catalyst suitable for producing dimethyl ether at a high yield and a method for producing the catalyst, and to provide a method for producing dimethyl ether at a high space time yield.

To attain the object, the present invention provides a first catalyst suitable for producing dimethyl ether, the catalyst comprising:

alumina particles having an average size of 200 $\mu$m or less;

a layer comprising a methanol synthesis catalyst, the layer being formed around each of the alumina particles; and the methanol synthesis catalyst having a weight ratio of 0.05 to 5 to a weight of the alumina particles.

In the first catalyst, the average size of the alumina particles is preferably 1 to 100 $\mu$m. The average size of 1 to 50 $\mu$m is more preferable.

The methanol synthesis catalyst may comprise copper oxide, zinc oxide and alumina. It is desirable that a weight ratio of the copper oxide:the zinc oxide:the alumina is 1:0.05 to 20:0 to 2. The methanol synthesis catalyst may comprise zinc oxide, chromium oxide and alumina. It is desirable that a weight ratio of the zinc oxide:the chromium oxide:the alumina being 1:0.1 to 10:0 to 2.

The first catalyst suitable for producing dimethyl ether is produced by the following method comprising the steps of:

forming a layer comprising a methanol synthesis catalyst around each of alumina particles; and washing the alumina particles, around which the layer was formed, with an acid aqueous solution.

The forming of the layer may comprise:

forming a slurry by introducing the alumina particles into an aqueous solution containing a metallic salt of active element of the methanol synthesis catalyst;

heating the slurry; and neutralizing the heated slurry with a base solution, thereby the active element of the methanol synthesis catalyst being deposited around each of the alumina particles.

The deposition of the active element of the methanol synthesis catalyst is preferably carried out at a temperature of 50 to 90° C.

Dimethyl ether is produced by using the first catalyst. A method for producing dimethyl ether comprising the steps of:

provinding the first catalyst suitable for producing dimethyl ether, the catalyst;

forming a slurry by introducing the catalyst into a solvent; and introducing a mixed gas comprising carbon monoxide and hydrogen into the slurry.

The present invention provides a second catalyst suitable for producing dimethyl ether, the catalyst comprising:

alumina particles having pores;

deposits which exist inside the pores; and the deposits comprising copper oxide, zinc oxide, and alumina.

It is preferable that the alumina particles have an average size of 200 μm or less. A weight ratio of the copper oxide:the zinc oxide:the alumina is preferably 1:0.05 to 20:0 to 2.

The second catalyst suitable for producing dimethyl ether is produced by the method comprising the steps of:

(a) introducing an alumina having pores into an aqueous solution containing a copper salt, a zinc salt and an aluminum salt for impregnating the pores with the aqueous solution;

(b) vaporizing the aqueous solution on a surface of the alumina;

(c) contacting the alumina subjected to the step (b) with a solution containing a deposition agent for hydrolyzing the copper salt, the zinc salt and the aluminum salt to copper hydroxide, zinc hydroxide and aluminum hydroxide and for depositing the copper hydroxide, the zinc hydroxide and the aluminum hydroxide within the pores of the alumina;

(d) washing the alumina subjected to the step (c); and (e) calcining the washed alumina.

Dimethyl ether is produced by using the second catalyst. A method for producing dimethyl ether comprising the steps of:

providing the second catalyst suitable for producing dimethyl ether;

forming a slurry by introducing the catalyst into a solvent; and introducing a mixed gas comprising carbon monoxide and hydrogen into the slurry.

The present invention provides a third catalyst suitable for producing dimethyl ether, the catalyst comprising:

a methanol synthesis catalyst;

a methanol dehydration catalyst; and a binder for integrating the methanol synthesis catalyst and the methanol dehydration catalyst.

The methanol synthesis catalyst may comprise copper oxide, zinc oxide and alumina. A weight ratio of the copper oxide:the zinc oxide:the alumina is preferably 1:0.05 to 20:0 to 2. Also, the methanol synthesis catalyst may comprise zinc oxide, chromium oxide and alumina. A weight ratio of the zinc oxide:the chromium oxide the alumina is preferably 1:0.1 to 10:0 to 2. The methanol dehydration catalyst may be at least one selected from the group consisting of γ-alumina, silica-alumina and zeolite. The third catalyst may further comprise a water gas shift catalyst. The water gas shift catalyst may comprise iron oxide and chromium oxide. The binder may be alumina sol or clay.

Dimethyl ether is produced by using the third catalyst. A method for producing dimethyl ether comprising the steps of:

providing the third catalyst suitable for producing dimethyl ether;

forming a slurry by introducing the catalyst into a solvent; and introducing a mixed gas comprising carbon monoxide and hydrogen into the slurry.

Further, the present invention provides a method for producing a catalyst suitable for producing dimethyl ether, the method comprising the steps of:

(a) preparing a methanol synthesis catalyst, a methanol dehydration catalyst, a water gas shift catalyst and a solvent;

(b) calculating an A value regarding to the methanol synthesis catalyst, the methanol dehydration catalyst and the water gas shift catalyst using an average particle size of the catalyst, a particle density of the catalyst and a density of the solvent, the A value being defined by the following equation:

$$A = D^2(P-S),$$

where

D denotes the average particle size of the catalyst, (cm),

P denotes the particle density of the catalyst, (g/cm$^3$), and

S denotes the density of the solvent, (g/cm$^3$), (c) controlling at least one of the group consisting of the average particle size of the catalyst, the particle density of the catalyst and the density of the solvent to maintain differences in the A values within $\pm 1 \times 10^{-6}$ g/cm among the methanol synthesis catalyst, the methanol dehydration catalyst, and the water gas shift catalyst;

(d) after the step (c), suspending the methanol synthesis catalyst, the methanol dehydration catalyst, and the water gas shift catalyst in the solvent.

Furthermore, dimethyl ether can be produced by the method comprising the steps of:

providing a mixed gas containing carbon monoxide and at least one selected from the group of hydrogen and water vapor;

contacting the mixed gas with a first catalyst consisting essentially of a methanol synthesis catalyst, a dehydration catalyst and a water gas shift catalyst; and contacting the mixed gas, which contacted with the first catalyst, with a second catalyst consisting essentially of at least one selected from the group of a dehydration catalyst and a water gas shift catalyst.

Moreover, dimethyl ether can be produced by the method comprising the steps of:

(a) reacting a raw material gas containing carbon monoxide and hydrogen in the presence of a catalyst to produce a reaction gas including dimethyl ether, carbon dioxide, carbon monoxide and hydrogen;

(b) separating the reaction gas into the carbon monoxide and the hydrogen, and the dimethyl ether and the carbon dioxide;

(c) recycling the carbon monoxide and the hydrogen which were separated from the reaction gas in the step (b);

(d) removing the carbon dioxide from the dimethyl ether and the carbon dioxide of the step (b) to gain the dimethyl ether; and (e) recycling the dimethyl ether which was gained in the step (d) to the step (b).

Further, dimethyl ether can be produced by the method comprising the steps of:

preparing a slurry which is produced by dispersing a dimethyl ether synthesis catalyst into a medium oil;

contacting a raw material gas containing carbon monoxide and hydrogen with the slurry to produce a product gas containing a vaporized medium oil;

cooling the product gas to condense the vaporized medium oil;

obtaining dimethyl ether from the product gas from which the vaporized medium oil was condensed;

removing a catalyst-deactivation ingredient from the condensed medium oil; and recycling the medium oil, from which the catalyst-deactivation ingredient was-removed, to the step of preparing the slurry.

Further, the present invention provides an apparatus for producing dimethyl ether comprising:

a slurry-bed reactor filled with a dimethyl ether synthesis catalyst and a medium oil therefor;

a condenser for condensing a vaporized medium oil discharged from the reactor;

an adsorber for removing a catalyst-deactivation ingredient from the medium oil condensed in the condenser; and recycle means for recycling the medium oil to the slurry-bed reactor.

DESCRIPTION OF THE EMBODIMENT

Embodiment 1

Figure 1:
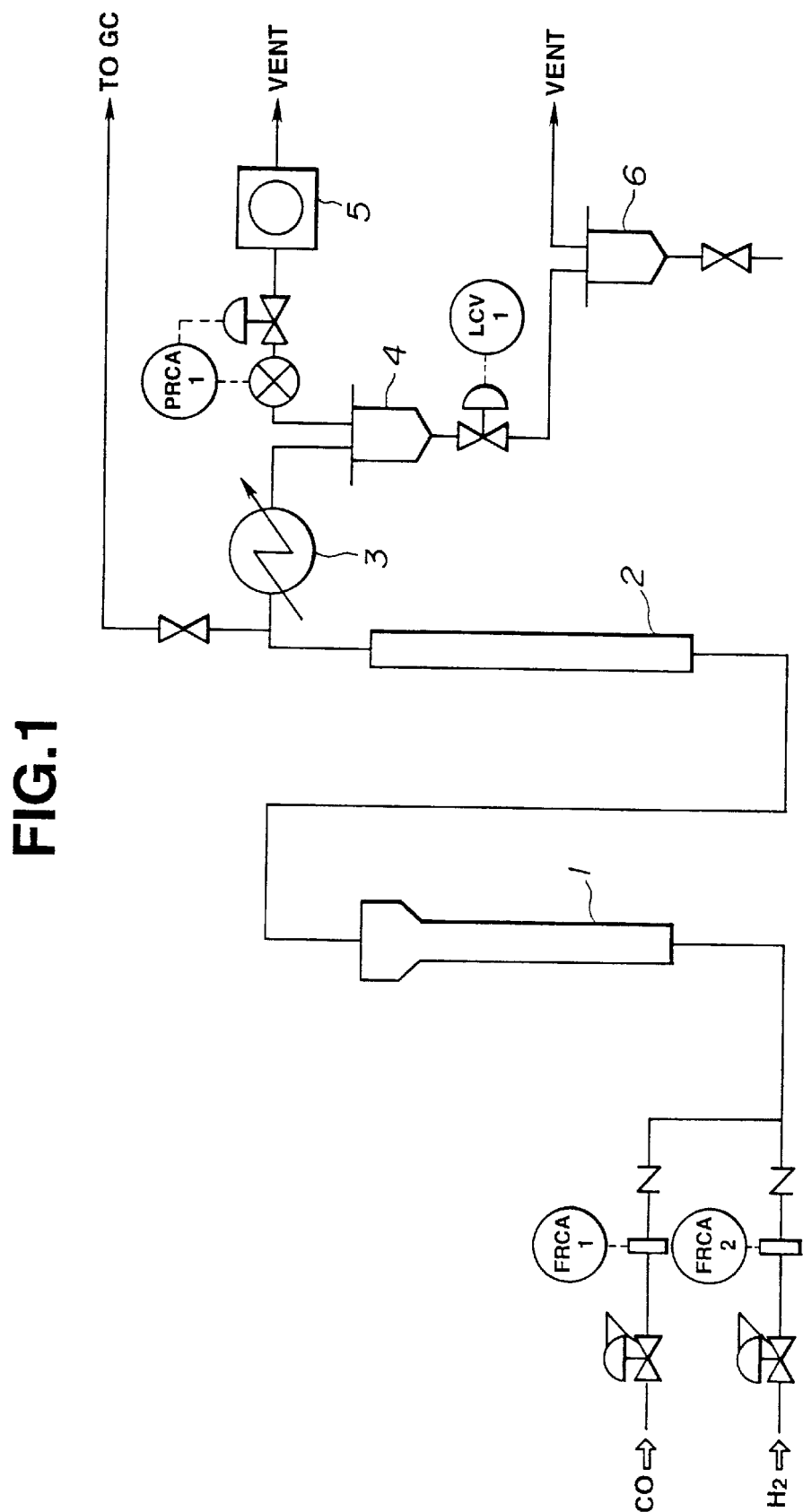
FIG. 1 is a schematic representation showing the apparatus for producing a dimethyl ether used in the embodiment 5.

The catalyst according to the present invention comprises alumina particles and a methanol synthesis catalyst layer formed around each of the alumina particles. Alumina functions as a methanol-dehydration catalyst, and alumina in use as an ordinary catalyst may be applied without further processing. A preferable size of alumina particles is fine, preferably 200 μm or less of average particle size, more preferably in an approximate range of from 1 to 100 μm, and most preferably in an approximate range of from 1 to 50 μm. To prepare the preferred average particle size, alumina may be pulverized as needed.

Methanol synthesis catalyst may be copper oxide-zinc oxide-alumina system and zinc oxide-chromium oxide-alumina system. A preferable mixing ratio of individual ingredients of copper oxide, zinc oxide, and alumina is: in an approximate range of from 0.05 to 20 wt.parts of zinc oxide to 1 wt.parts of copper oxide, more preferably in an approximate range of from 0.1 to 5 wt.parts; in an approximate range of from 0 to 2 wt.parts of alumina, more preferably in an approximate range of from 0 to 1 wt.parts. A preferable mixing ratio of individual ingredients of zinc oxide, chromium oxide, and alumina is: in an approximate range of from 0.1 to 10 of chromium oxide to 1 wt.parts of zinc oxide, more preferably in an approximate range of from 0.5 to 5; and in an approximate range of from 0 to 2 wt.parts of alumina, more preferably in an approximate range of from 0 to 1 wt.parts.

A preferable ratio of the methanol synthesis catalyst layer formed around alumina particle is in a range of from 0.05 to 5 by wt.parts to 1 wt.parts of alumina, more preferably in a range of from 0.1 to 3 wt.parts, and most preferably in a range of from 0.5 to 2 wt.parts.

The catalyst achieves 30 % or higher CO conversion, or normally in an approximate range of from 35 to 60%, and particularly in an approximate range of from 45 to 55%, and achieves 20% or higher dimethyl ether yield, or normally in an approximate range of from 25 to 45%, and particularly in an approximate range of from 35 to 45%. A preferred particle size of the catalyst is small as far as possible within a range that no agglomeration problem occurs. A preferable average particle size of the catalyst is 200 μm or less, more preferably in an approximate range of from 1 to 100 μm, and most preferably in an approximate range of from 1 to 50 μm.

The method for manufacturing the catalyst according to the present invention is characterized in the steps of: forming a methanol synthesis catalyst around each of alumina particles; and washing the catalyst layer with an acid aqueous solution. For manufacturing the catalyst, powdered alumina is charged into an aqueous solution containing a metallic salt of active ingredient of methanol synthesis catalyst, for example an aqueous solution of copper salt, zinc salt, and aluminum salt, to prepare a slurry. Copper salt, zinc salt, and aluminum salt may be either inorganic salt or organic salt if only the salt is a water soluble salt. Nevertheless, a salt that likely generates hydroxide in water is not suitable. As for the salt of copper and of zinc (and chronium), nitrate, carbonate, organic acid salt are applicable. For the salt of halide and of aluminum, nitrate, carbonate, and organic salt are applicable. A preferable concentration of each ingredient is in an approximate range of from 0.1 to 3 mole/liter.

Thus prepared alumina slurry is then heated, and a base solution is added dropwise to the heated slurry to neutralize to deposit the active ingredient of the methanol synthesis catalyst around each of alumina particles. The alumina particle may be coated by copper salt, zinc salt, and aluminum salt separately at need. A preferable temperature of the slurry during the period of deposition is in a range of from 50 to 90° C., more preferably in a range of from 60 to 85° C. Any kind of base is applicable if only it can neutralize the acid in the slurry. The neutralization is to deposit copper, zinc, and aluminum, and a preferable pH value is in an approximate range of from 6 to 12, more preferably in an approximate range of from 7 to 10. After neutralization, the slurry is allowed to stand for an appropriate time or is subjected to mild agitation for aging to sufficiently develop the deposits.

The alumina particles on each of which the deposit is formed are separated from liquid. Thus separated solid alumina particles are washed with warm water. Normally, succeeding drying and calcining treatment provides a catalyst configured by alumina coated by a methanol synthesis catalyst. With the catalyst according to the present invention, however, methanol which is generated on the methanol synthesis catalyst migrates onto the alumina which is a methanol-dehydration catalyst, where the methanol undergoes dehydration and condensation by the action of acid active centers on the alumina to yield dimethyl ether, which mechanism is described later. In the deposit-forming operation described above, alumina contacts with base solution, and the acid active centers on alumina vanish. To recover the acid active centers on alumina, the method for manufacturing catalyst according to the present invention involves washing the alumina particles with an acid aqueous solution after forming the above-described deposit. For washing, the alumina particles may be suspended in an acid aqueous solution. Applicable acid for washing is either inorganic acid or organic acid. A preferable acid includes nitric acid, hydrochloric acid, and acetic acid, and more preferably nitric acid and hydrochloric acid. The concentration of acid for acid washing is in an approximate range of from 0.1 to 5 mole/liter, more preferably in an approximate range of from 0.5 to 2 mole/liter. The temperature for washing may be room temperature, and a warm temperature may also be applicable. The period for washing may be in an approximate range of from 10 to 30 min.

The next step is washing the alumina particles and deposits thoroughly with ion-exchanged water or the like to remove acid and base ions, followed by drying and calcining. The calcining may be carried out in air. The calcining temperature may be a temperature level that the metal hydroxide in the catalyst ingredients for methanol-synthesis is converted to metal oxide. For instance, a preferable calcining condition is preferably carried out at a temperature range of from 250 to 400° C. for a period of from 1 to 10 hours.

The above-described catalyst is used in a state of slurry a solvent. The amount of catalyst in the solvent depends on the kind of the solvent, the reaction conditions, and other variables. Normally, the amount of catalyst is in a range of from 1 to 50 wt. % to the amount of the solvent.

The kind of solvent used for synthesizing dimethyl ether according to the present invention is arbitrarily selected if only the solvent is in a liquid phase under the reaction conditions. Examples of the solvent are hydrocarbons of aliphatic, aromatic, and alicyclic groups, alcohol, ether, ester, ketone, halide, or their mixture.

Alternatively, gas oil after removing sulfur ingredients, vacuum gas oil, high boiling point distillates of coal tar after treated by hydrogenation are also applicable as the solvent.

By passing a mixed gas of carbon monoxide and hydrogen through thus prepared slurry of catalyst with solvent, dimethyl ether is obtained at a high yield. An applicable range of the molar mixing ratio of hydrogen to carbon monoxide ($H_2/CO$) is wide, for instance, in a range of from 20 to 0.1 as ($H_2/CO$), and more preferably from 10 to 0.2.

According to the reaction system, the mixed gas does not directly contact with catalyst only after being dissolved into a solvent. Consequently, catalytic reaction system, but the carbon monoxide and hydrogen contact with catalyst only after being dissolved into a solvent. Consequently, selection of an adequate kind of solvent taking into account of the solubility of carbon monoxide and hydrogen to the solvent establishes a constant composition of carbon monoxide and hydrogen in the solvent independent of the gas composition, and sustains the supply of the mixed gas at an established composition to the catalyst surface.

In the case of a mixed gas with a significantly low ratio of ($H_2/CO$), for example, 0.1 or less, or in the case of solely carbon monoxide without containing hydrogen, it is necessary to separately supply steam to convert a part of the carbon monoxide into hydrogen and carbon dioxide within the reactor.

Since solvent exists between the raw material gases and the catalyst, the gas composition does not necessarily agree with the composition on the catalyst surface. Therefore, it is acceptable that the mixed gas of carbon monoxide and hydrogen, or solely carbon monoxide gas includes a relatively high concentration of carbon dioxide (in a range of from 20 to 50%).

The manufacturing method according to the present invention significantly reduces the effect of ingredients that may act as a catalyst-poison on the catalyst compared with the gas-solid contact catalyst system. Examples of the catalyst-poisoning ingredients which may exist in the raw material gas are sulfur compounds such as hydrogen sulfide, cyan compounds such as hydrogen cyanide, and chlorine compounds such as hydrogen chloride. Even when the catalyst activity decreases as a result of poisoning, the productivity of the total reactor system is maintained at a constant level by withdrawing the slurry from the reactor and by charging fresh slurry containing catalyst of high activity to the reactor.

The reaction heat is recovered in a form of medium pressure steam using a cooling coil installed inside of the reactor while passing hot water through the cooling coil. The cooling system controls the reaction temperature at an arbitrary level.

A preferable reaction temperature is in a range of from 150 to 400° C., and particularly preferable in a range of from 200 to 350° C. The reaction temperature below 150° C. and above 400° C. degrades the conversion of carbon monoxide.

A preferable reaction pressure is in a range of from 10 to 300 kg/cm$^2$, and particularly preferable in a range of from 15 to 150 kg/cm$^2$. The reaction pressure below 10 kg/cm$^2$ results in a low conversion of carbon monoxide, and that above 300 kg/cm$^2$ requires a special design of the reactor and is uneconomical because of the need of a large amount of energy for pressurizing the system.

A preferable space velocity (charge rate of mixed gas per 1 g of catalyst under standard condition) is in a range of from 100 to 50000 ml/g·h, and particularly preferable from 500 to 30000 ml/g·h. The space velocity above 50000 ml/g·h degrades the conversion of carbon monoxide, and that below 100 ml/g·h is uneconomical because of the need of an excessively large reactor.

The catalyst for manufacturing dimethyl ether according to the present invention comprises alumina particles with a methanol synthesis catalyst layer formed around each of the alumina particles. The method for manufacturing the catalyst is characterized in the steps of: forming a catalyst active ingredients for synthesizing methanol around each of alumina particles; and washing the catalyst active ingredients with an acid aqueous solution. Since every catalyst ingredient has a size of a molecular level and since each of the ingredients chemically adsorbs by each other, they do not separate during the reaction period. In addition, a very small distance of adjacent active ingredients allows the reaction cycle described below to proceed promptly, thus improving the yield of dimethyl ether. That is, the sequent order of the reaction begins with the yielding of methanol from carbon monoxide and hydrogen on the methanol synthesis catalyst, then the produced methanol migrates onto the alumina inside of the catalyst, where the methanol undergoes dehydration and condensation on the acid active centers on alumina, thus yielding dimethyl ether and water. Furthermore, the water migrates onto the methanol synthesis catalyst, where the water reacts with carbon monoxide to yield carbon dioxide and hydrogen. The reaction follows the reaction formulae given below.

$$CO+2H_2 \rightarrow CH_3OH$$

$$2CH_3OH \rightarrow CH_3OCH_3+H_2O$$

$$CO+H_2O \rightarrow CO_3+H_2$$

The method for manufacturing dimethyl ether according to the present invention significantly increases the yield of dimethyl ether by using the catalyst which comprises alumina particles and methanol synthesis catalyst layer formed around each of the alumina particles in a state of slurry with a solvent. The method is free from problems such as plugging of catalyst and mechanical strength of catalyst, is designed to readily absorb the reaction heat through a cooling pipe or the like, and is designed to conduct withdrawing and filling of catalyst easily.

EXAMPLE

I. Preparation of Catalyst

Examples 1, 5 through 8

Each of 185 g of copper nitrate ($Cu(NO_3)_2 \cdot 3H_2O$), 117 g of zinc nitrate ($Zn(NO_3)_2 \cdot 6H_2O$), and 52 g of aluminum nitrate ($Al(NO_3)_3 \cdot 9H_2O$) were dissolved into about 1 liter of ion-exchanged water. To the solution, 100 g of fine powder of γ-alumina (N612, Nikki Kagaku Co.) having an approximate particle size of 20 μm or less was added. The prepared slurry was heated to around 80° C. and held at the temperature. Separately, about 1.4 kg of sodium carbonate ($Na_2CO_3$) was dissolved into about 1 liter of ion-exchanged water, which solution was then heated to about 80° C. The solution was added dropwise to the slurry until the slurry reached to pH 8.0. After completing the dropwise addition, the slurry was allowed to stand for about 1 hour for aging. Then, the slurry was filtered, and the cake was rinsed by ion-exchanged water at about 80° C. until sodium ion and nitric acid ion are not detected anymore. After the rinse, the resultant alumina particles were suspended in about 1 liter of aqueous solution of 1 mole/liter nitric acid, and were washed at room temperature for 20 min. The suspension was filtered to recover the alumina particles. The alumina particles were further rinsed with ion-exchanged water until no acid was detected anymore. The alumina particles were then dried at 120° C. for 24 hours followed by calcining thereof in air at 350° C. for 5 hours. The calcined alumina particles were classified to recover 120 μm or finer ones as the target catalyst.

Analysis of thus obtained catalyst gave the composition as $CuO:ZnO:Al_2O_3=31:16:53$ (by weight).

Example 2

Each of 37.1 g of copper nitrate ($Cu(NO_3)_2 3H_2O$), 23.4 g of zinc nitrate ($Zn(NO_3)_2$ $6H_2O$), and 10.3 g of aluminum nitrate ($Al(NO_3)_3 \cdot 9H_2O$) were dissolved into about 1 liter of ion-exchanged water. To the solution, 100 g of fine powder of γ-alumina (N612, Nikki Kagaku Co.) having an approximate particle size of 20 μm or less was added. The prepared slurry was heated to around 80° C. and held at the temperature. Separately, about 0.3 kg of sodium carbonate ($Na_2CO_3$) was dissolved into about 1 liter of ion-exchanged water, which solution was then heated to about 80° C. The solution was added dropwise to the slurry until the slurry reached to pH 8.0. After completing the dropwise addition, the slurry was allowed to stand for about 1 hour for aging. Then, the slurry was filtered, and the cake was rinsed by ion-exchanged water at about 80° C. until sodium ion and nitric acid ion were not detected anymore. After the rinse, the resultant alumina particles were suspended in about 1 liter of aqueous solution of 1 mole/liter nitric acid, and were washed following the procedure applied in Example 1. The alumina particles were then dried at 120° C. for 24 hours, followed by calcining thereof in air at 350° C. for 5 hours. The calcined alumina particles were classified to recover 120 μm or finer ones as the target catalyst.

Analysis of thus obtained catalyst gave the composition as $CuO:ZnO:Al_2O_3=20:11:69$ (by weight).

Example 3

Each of 92.6 g of copper nitrate ($Cu(NO_3)_2 \cdot 3H_2O$), 58.5 g of zinc nitrate ($Zn(NO_3)_2 \cdot 6H_2O$), and 25.5 g of aluminum nitrate ($Al(NO_3)_3 \cdot 9H_2O$) were dissolved into about 1 liter of ion-exchanged water. To the solution, 100 g of fine powder of γ-alumina (N612, Nikki Kagaku Co.) having an approximate particle size of 20 μm or less was added. The prepared slurry was heated to around 80° C. and held at the temperature. Separately, about 0.7 kg of sodium carbonate ($Na_2CO_3$) was dissolved into about 1 liter of ion-exchanged water, which solution was then heated to about 80° C. The solution was added dropwise to the slurry until the slurry reached to pH 8.0. After completing the dropwise addition, the slurry was allowed to stand for about 1 hour for aging. Then, the slurry was filtered, and the cake was rinsed by ion-exchanged water at about 80° C. until sodium ion and nitric acid ion were not detected anymore. After the rinse, the resultant alumina particles were suspended in about 1 liter of aqueous solution of 1 mole/liter nitric acid, and were washed following the procedure applied in Example 1. The alumina particles were then dried at 120° C. for 24 hours, followed by calcining thereof in air at 350° C. for 5 hours. The calcined alumina particles were classified to recover 120 μm or finer ones as the target catalyst.

Analysis of thus obtained catalyst gave the composition as $CuO:ZnO:Al_2O_3=31:16:53$ (by weight).

Example 4

Each of 185 g of copper nitrate ($Cu(NO_3)_2 \cdot 3H_2O$), 117 g of zinc nitrate ($Zn(NO_3)_2 \cdot 6H_2O$), and 52 g of aluminum nitrate ($Al(NO_3)_3 \cdot 9H_2O$) were dissolved into about 1 liter of ion-exchanged water. To the solution, 50 g of fine powder of γ-alumina (N612, Nikki Kagaku Co.) having an approximate particle size of 20 μm or less was added. The prepared slurry was heated to around 80° C. and held at the temperature. Separately, about 1.4 kg of sodium carbonate ($Na_2CO_3$) was dissolved into about 1 liter of ion-exchanged water, which solution was then heated to about 80° C. The solution was added dropwise to the slurry until the slurry reached to pH 8.0. After completing the dropwise addition, the slurry was allowed to stand for about 1 hr for aging. Then, the slurry was filtered, and the cake was rinsed by ion-exchanged water at about 80° C. until sodium ion and nitric acid ion were not detected anymore. After the rinse, the resultant alumina particles were washed by about 1 liter of aqueous solution of 1 mole/liter nitric acid following the procedure applied in Example 1. The alumina particles were then dried at 120° C. for 24 hours followed by calcining thereof in air at 350° C. for 5 hours. The calcined alumina particles were classified to recover 120 μm or finer ones as the target catalyst.

Analysis of thus obtained catalyst gave the composition as $CuO:ZnO:Al_2O_3$=41:21:38 (by weight).

Example 9

A catalyst was prepared following the procedure applied in Example 1 except that the temperature of slurry was set to 40° C.

Example 10

A catalyst was prepared following the procedure applied in Example 1 except that the temperature of slurry was set to 50° C.

Example 11

A catalyst was prepared following the procedure applied in Example 1 except that the temperature of slurry was set to 60° C.

Example 12

A catalyst was prepared following the procedure applied in Example 1 except that the temperature of slurry was set to 70° C.

Example 13

A catalyst was prepared following the procedure applied in Example 1 except that the temperature of slurry was set to 90° C.

Example 14

A catalyst was prepared following the procedure applied in Example 1 except that the temperature of slurry was set to 95° C.

Comparative Example 1

A catalyst was prepared following the procedure applied in Example 1 except that the temperature of slurry was set to 20° C.

Comparative Example 2

A catalyst was prepared following the procedure applied in Example 1 except that the cake was rinsed only with ion-exchanged water and not rinsed with aqueous solution of nitric acid.

Comparative Example 3

Each of 185 g of copper nitrate ($Cu(NO_3)_2 \cdot 3H_2O$), 117 g of zinc nitrate ($Zn(NO_3)_2 \cdot 6H_2O$), and 52 g of aluminum nitrate ($Al(NO_3)_3 \cdot 9H_2O$) were dissolved into about 1 liter of ion-exchanged water. Separately, about 1.4 kg of sodium carbonate ($Na_2CO_3$) was dissolved into about 1 liter of ion-exchanged water. Both of these solutions were added dropwise to about 3 liters of ion-exchanged water in a stainless steel vessel controlled at about 80° C., for a period of about 2 hours while maintaining the pH value of the mixture to 8.0±0.5. After completing the dropwise addition, the mixture was allowed to stand for about 1 hour for aging. When, during the processing period, pH value came outside of a range of 8.0±0.5, an aqueous solution of about 1 mole/liter nitric acid or of about 1 mole/liter sodium carbonate was added dropwise to the mixture to sustain the pH value in a range of 8.0±0.5. Then, the generated precipitate was filtered, and the cake was rinsed by ion-exchanged water until nitric acid ion is not detected in the filtrate anymore. The cake was then dried at 120° C. for 24 hours. followed by calcining thereof in air at 350° C. for 5 hours. A 50 g portion of the calcined cake was powdered in a ball mill along with 50 g of γ-alumina (N612, Nikki Kagaku Co.) for about 3 hours. The powder mixture was calcined in air at 450° C. for 3 hours. The calcined mixture was further powdered to about 120 μm or finer size as the target catalyst.

Analysis of thus obtained catalyst gave the composition as $CuO:ZnO:Al_2O_3$=31:16:53 (by weight).

II. Method for Activating Catalyst and Reaction Method

A 24 g of n-hexadecane (31. 1 ml) was charged to a bubble-tower reactor having 2 cm of inside diameter and 2 m of height, and 3.6 g of each of the above-described catalyst powders was added to make the contents of the reactor in a suspended state. In Examples 5 through 8, the catalyst of Example 1 was used. A mixed gas of hydrogen, carbon monoxide, and nitrogen (at a molar ratio $H_2:CO:N_2$ of 1:1:9) was introduced to pass through the bubble-tower at a flow rate of about 300 ml/min. While flowing the mixed gas through the bubble-tower, the temperature in the bubble-tower was gradually raised from room temperature to 220° C. within a period of several hours. At the same time, the concentration of nitrogen in the mixed gas was gradually reduced to a final level of zero. Then, the reaction system was held at 220° C. for about 3 hours to activate the catalyst.

The reaction was conducted at a specified temperature and pressure while introducing the mixed gas of hydrogen, carbon monoxide, and carbon dioxide at a molar ratio of $H_2/CO/CO_2$=47.5/47.5/5.0 and at a flow rate of 336 ml/min. (converted at a condition of normal temperature and pressure).

The obtained reaction products and non-reacted substances were analyzed by gas chromatography.

III. Reaction Conditions and Experimental Results

The reaction conditions and experimental results are shown in Tables 1 through 5.

TABLE 1

| | Example 1 | Example 2 | Example 3 | Example 4 |
|---|---|---|---|---|
| Condition | | | | |
| Temperature (° C.) | 280 | 280 | 280 | 280 |
| Pressure (kg/cm²-G) | 30 | 30 | 30 | 30 |
| Reaction Result | | | | |
| CO conversion (%) | 47.7 | 37.8 | 40.5 | 48.3 |

TABLE 1-continued

|  | Example 1 | Example 2 | Example 3 | Example 4 |
|---|---|---|---|---|
| Yield (C-mol %) |  |  |  |  |
| Dimethyl ether | 36.5 | 25.3 | 28.4 | 35.7 |
| Methanol | 2.0 | 0.7 | 1.1 | 2.4 |
| Hydrocarbons | 0.3 | 0.2 | 0.3 | 0.1 |
| $CO_2$ | 8.9 | 11.6 | 10.7 | 10.1 |
| Dimethyl ether space time yield (g/kg-cat · h) | 998 | 692 | 777 | 976 |

TABLE 2

|  | Example 5 | Example 6 | Example 7 | Example 8 |
|---|---|---|---|---|
| Condition |  |  |  |  |
| Temperature (° C.) | 250 | 300 | 280 | 280 |
| Pressure (kg/cm²-G) | 30 | 30 | 20 | 50 |
| Reaction Result |  |  |  |  |
| CO conversion (%) | 40.3 | 45.1 | 38.4 | 55.9 |
| Yield (C-mol %) |  |  |  |  |
| Dimethyl ether | 24.2 | 33.8 | 26.5 | 43.6 |
| Methanol | 3.8 | 1.7 | 1.5 | 2.2 |
| Hydrocarbons | 0.1 | 2.8 | 0.4 | 0.8 |
| $CO_2$ | 12.2 | 6.8 | 10.0 | 9.3 |
| Dimethyl ether space time yield (g/kg-cat · h) | 662 | 924 | 725 | 1192 |

TABLE 3

|  | Example 9 | Example 10 | Example 11 | Example 12 |
|---|---|---|---|---|
| Condition |  |  |  |  |
| Temperature (° C.) | 280 | 280 | 280 | 280 |
| Pressure (kg/cm²-G) | 30 | 30 | 30 | 30 |
| Reaction Result |  |  |  |  |
| CO conversion (%) | 38.8 | 40.2 | 46.9 | 47.8 |
| Yield (C-mol %) |  |  |  |  |
| Dimethyl ether | 28.5 | 31.1 | 36.1 | 35.9 |
| Methanol | 3.1 | 2.4 | 1.8 | 2.2 |
| Hydrocarbons | 0.1 | 0.1 | 0.2 | 0.2 |
| $CO_2$ | 7.1 | 6.6 | 8.8 | 9.5 |
| Dimethyl ether space time yield (g/kg-cat · h) | 779 | 850 | 987 | 982 |

TABLE 4

|  | Example 13 | Example 14 | Comparative Example 1 | Comparative Example 2 |
|---|---|---|---|---|
| Condition |  |  |  |  |
| Temperature (° C.) | 280 | 280 | 280 | 280 |
| Pressure (kg/cm²-G) | 30 | 30 | 30 | 30 |

TABLE 4-continued

|  | Example 13 | Example 14 | Comparative Example 1 | Comparative Example 2 |
|---|---|---|---|---|
| Reaction Result |  |  |  |  |
| CO conversion (%) | 41.9 | 40.0 | 30.1 | 18.4 |
| Yield (C-mol %) |  |  |  |  |
| Dimethyl ether | 32.1 | 29.3 | 17.5 | 6.5 |
| Methanol | 1.7 | 2.0 | 5.7 | 6.5 |
| Hydrocarbons | 0.1 | 0.2 | 0.1 | 0.1 |
| $CO_2$ | 8.0 | 8.5 | 6.8 | 1.3 |
| Dimethyl ether space time yield (g/kg-cat · h) | 878 | 801 | 478 | 178 |

TABLE 5

|  | Reaction result in Example 1 after 100 hours of continuous reaction | Reaction result in Example 3 after 100 hours of continuous reaction |
|---|---|---|
| Condition |  |  |
| Temperature (° C.) | 280 | 280 |
| Pressure (kg/cm²-G) | 30 | 30 |
| Reaction Result |  |  |
| CO conversion (%) | 41.9 | 27.3 |
| Yield (C-mol %) |  |  |
| Dimethyl ether | 36.3 | 13.8 |
| Methanol | 1.8 | 9.8 |
| Hydrocarbons | 0.2 | 0.5 |
| $CO_2$ | 8.8 | 3.2 |
| Dimethyl ether space time yield (g/kg-cat · h) | 992 | 377 |

The catalyst for manufacturing dimethyl ether according to the present invention provides effects of preventing separation of individual catalyst ingredients from each other during reaction, of assuring smooth progress of reaction cycle, and of achieving high dimethyl ether yield owing to the configuration thereof comprising alumina particles and methanol synthesis catalyst layer formed around each of the alumina particles.

The method for manufacturing dimethyl ether according to the present invention uses a slurry of solvent with a catalyst comprising alumina particles and methanol synthesis catalyst layer formed around each of the alumina particles, so the method provides effects of achieving high space time yield of dimethyl ether, of being free from problems of plugging of catalyst and of mechanical strength of catalyst, of easiness for removing reaction heat and for controlling reaction heat, of assuring wide application range of the ratio of carbon monoxide to hydrogen, of progress of reaction under the presence of high concentration of carbon dioxide, and of less influence of impurities and catalyst poisons.

Embodiment 2

The catalyst according to the present invention comprises an alumina having micropores with deposits of copper oxide, zinc oxide, and alumina therein. Alumina functions as a methanol-dehydration catalyst, and alumina in use as an ordinary catalyst may be applied without further processing. A preferable size of alumina particles is a fine size, preferably 200 μm or less of average particle size, more preferably in an approximate range of from 1 to 100 μm, and most preferably in an approximate range of from 1 to 50 μm. To prepare the preferred average particle size, alumina may be pulverized as needed.

The ratio of copper oxide, zinc oxide, and alumina which are deposited on the surface of micropores in alumina is in an approximate range of from 0.05 to 20 wt.parts of zinc oxide to 1 wt.parts of copper oxide, more preferably in an approximate range of from 0.1 to 5 wt.parts; in an approximate range of from 0 to 2 wt.parts of alumina to 1 wt.parts of copper oxide, more preferably in an approximate range of from 0 to 0.5 wt.parts. A preferable deposition amount is in an approximate range of from 0.05 to 5 wt.parts of the sum of copper oxide, zinc oxide, and alumina to 1 wt.parts of the alumina particles being deposited thereon, and more preferably in an approximate range of from 0.1 to 3 wt.parts, and most preferably in an approximate range of from 0.5 to 2 wt.parts.

The catalyst achieves 25% or higher CO conversion, or normally in an approximate range of from 30 to 50%, and particularly in an approximate range of from 40 to 50%, and achieves 20% or higher dimethyl ether yield, or normally in an approximate range of from 25 to 35%, and particularly in an approximate range of from 30 to 35%. A preferred particle size of the catalyst is small as far as possible within a range that no agglomeration problem occurs. A preferable average particle size of the catalyst is 200 μm or less, more preferably in an approximate range of from 1 to 100 μm, and most preferably in an approximate range of from 1 to 50 μm.

The method for manufacturing the catalyst according to the present invention is characterized in the steps of: depositing copper oxide, zinc oxide, and alumina onto the surface of micropores in alumina using a base solution; then calcining the alumina and the deposits. For manufacturing the catalyst, granulated alumina particles or alumina powder is impregnated with an aqueous solution containing adequate kinds of copper salt, zinc salt, and aluminum salt. The kind of copper salt, zinc salt, and aluminum salt may be either an inorganic salt or an organic salt if only the salt is soluble in water. Nevertheless, a salt that likely generates hydroxide in water by hydrolysis is not suitable. As for the salt of copper and of zinc, nitrate, carbonate, organic acid salt are applicable. For the salt of halide and of aluminum, nitrate, carbonate, and organic salt are applicable. A preferable concentration of each ingredient is in an approximate range of from 0.1 to 3 mole/liter.

After the aqueous solution of the salts fully penetrated into the micropores in alumina, excess amount of aqueous solution is removed as needed, then the remaining aqueous solution is vaporized to dry. At the point that the surface water on the alumina is vaporized off, or at the point that the total amount of applied aqueous solution of the salts filled the micropores in alumina, the alumina is brought into contact with a solution of the deposition agent. The deposition agent is a base, which reacts with an inorganic portion that structures the copper salt, the zinc salt, and the aluminum salt to form a water-soluble salt, while the deposition agent itself is able to be emitted by thermal decomposition during the succeeding calcining step. A preferable deposition agent includes ammonia, urea, and an organic base, and particularly ammonia is preferred. A base which cannot be thermally decomposed, such as sodium hydroxide, potassium hydroxide, and sodium carbonate, is not favorable because that type of base remains in micropores in alumina even after sufficient washing with water to interfere with the catalyst activity. A preferable concentration of the solution of deposition agent is in an approximate range of from 0.5 to 10 mole/liter. With the addition of solution of deposition agent, copper salt, zinc salt, and aluminum salt are hydrolyzed within the micropores in alumina by the base as a deposition agent, thus depositing those salts onto the surface of the micropores. The deposition of copper, zinc, and aluminum may be conducted separately, at need. Applicable deposition temperature is around 80° C. at the maximum, and room temperature is preferred. As for the pH value, the pH in the micropores is important, though the pH within the micropores cannot be measured. The pH value in the solution of deposition agent is always at alkali side (pH>12). The deposits are then fully washed with ion-exchanged water or the like to remove base ions and inorganic ions, and the alumina with deposits is dried and calcined. The calcining may be conducted in air. The temperature of calcining is preferably at a temperature that copper hydroxide, zinc hydroxide, and aluminum hydroxide are converted into copper oxide, zinc oxide, and alumina, respectively, and that base is thermally decomposed to emit, or, for example, in a range of from 250 to 400° C. for a period of 1 to 10 hours.

Thus prepared catalysts are used in a state of slurry with a solvent after classifying to remove a portion of the catalysts which excessively enlarged their size caused by deposition. The amount of catalyst in the solvent depends on the kind of the solvent, the reaction conditions, and other variables. Normally, the amount of catalyst is in a range of from 1 to 50 wt. % to the amount of the solvent.

The kind of solvent used for synthesizing dimethyl ether according to the present invention is arbitrarily selected if only the solvent is in a liquid phase under the reaction condition. Examples of the solvent are hydrocarbons of aliphatic, aromatic, and alicyclic groups, alcohol, ether, ester, ketone, halide, or their mixture.

Alternatively, gas oil after removing sulfur ingredients, vacuum gas oil, high boiling point distillates of coal tar after treated by hydrogenation are also applicable as the solvent.

By passing a mixed gas of carbon monoxide and hydrogen through thus prepared slurry of catalyst with solvent, dimethyl ether is obtained at a high yield. An applicable range of molar mixing ratio of hydrogen to carbon monoxide ($H_2/CO$) is wide, for instance, in a range of from 20 to 0.1 as ($H_2/CO$), and more preferably from 10 to 0.2. According to the reaction system, the mixed gas does not directly contact with the catalyst, which direct contact occurs in a gas-solid catalytic reaction system, but the carbon monoxide and hydrogen contact with catalyst only after dissolved into a solvent. Consequently, selection of an adequate kind of solvent taking into account of the solubility of carbon monoxide and hydrogen to the solvent establishes a constant composition of carbon monoxide and hydrogen in the solvent independent of the gas composition, and sustains the supply of the mixed gas at an established composition to the catalyst surface.

In the case of a mixed gas with a significantly low ratio of ($H_2/CO$), for example, 0.1 or less, or in the case of solely carbon monoxide without containing hydrogen, it is necessary to separately supply steam to convert a part of the carbon monoxide into hydrogen and carbon dioxide within the reactor.

Since solvent exists between the raw material gases and the catalyst, the gas composition does not necessarily agree with the composition on the catalyst surface. Therefore, it is acceptable that the mixed gas of carbon monoxide and hydrogen, or solely carbon monoxide gas includes a relatively high concentration of carbon dioxide (in a range of from 20 to 50%).

The manufacturing method according to the present invention significantly reduces the effect of ingredients that may act as a catalyst-poison on the catalyst compared with the gas-solid contact catalyst system. Examples of the catalyst-poisoning ingredients which may exist in the raw material gas are sulfur compounds such as hydrogen sulfide, cyan compounds such as hydrogen cyanide, and chlorine compounds such as hydrogen chloride. Even when the catalyst activity is decreased as a result of poisoning, the productivity of the total reactor system is maintained at a constant level by withdrawing the slurry from the reactor and by charging fresh slurry containing catalyst of high activity to the reactor.

The reaction heat is recovered in a form of medium pressure steam using a cooling coil installed inside of the reactor while passing hot water through the cooling coil. The cooling system controls the reaction temperature at an arbitrary level.

A preferable reaction temperature is in a range of from 150 to 400° C., and particularly preferable in a range of from 200 to 350° C. The reaction temperature below 150° C. and above 400° C. degrades the conversion of carbon monoxide.

A preferable reaction pressure is in a range of from 10 to 300 kg/cm$^2$, and particularly preferable in a range of from 15 to 150 kg/cm$^2$. The reaction pressure below 10 kg/cm$^2$ results in a low conversion of carbon monoxide, and that above 300 kg/cm$^2$ requires a special design of the reactor and is uneconomical because of the need of a large amount of energy for pressurizing the system.

A preferable space velocity (charge rate of mixed gas per 1 g of catalyst under standard condition) is in a range of from 100 to 50000 ml/g·h, and particularly preferable from 500 to 30000 ml/g·h. The space velocity above 50000 ml/g·h degrades the conversion of carbon monoxide, and that below 100 ml/g·h is uneconomical because of the need of an excessively large reactor.

The catalyst for manufacturing dimethyl ether according to the present invention is prepared by depositing copper oxide, zinc oxide and alumina onto the surface of micropores in alumina. Individual catalyst ingredients do not separate from each other during the reaction process. Therefore, the reaction cycle proceeds smoothly, and a high yield of dimethyl ether is attained.

The method for manufacturing dimethyl ether according to the present invention significantly increases the yield of dimethyl ether by using the catalyst in a state of a slurry with a solvent, which catalyst is prepared by depositing copper oxide, zinc oxide, and alumina on the surface of micropores in alumina,. The method is free from problems such as plugging of catalyst and mechanical strength of catalyst, is designed to readily absorb the reaction heat through a cooling pipe or the like, and is designed to conduct withdrawing and filling of catalyst easily.

EXAMPLE

I. Preparation of Catalyst

Examples 1, 5 Through 8

Each of 185 g of copper nitrate ($Cu(NO_3)_2 \cdot 3H_2O$), 117 g of zinc nitrate ($Zn(NO_3)_2 \cdot 6H_2O$), and 52 g of aluminum nitrate ($Al(NO_3)_3 \cdot 9H_2O$) were dissolved into about 1 liter of ion-exchanged water. To the solution, 100 g of fine powder of γ-alumina (N612, Nikki Kagaku Co.) having an approximate particle size of 20 μm or less was added. The water of the mixture was removed by vaporizing in a water-bath. The resulted material was put into about 1 liter of about 5 mole/liter aqueous ammonia. The mixture was held for about 1 hour. Then the mixture was further washed until no ammonium ion nor nitric acid ion was detected anymore. The mixture was dried at 120° C. for 24 hours. followed by calcined in air at 350° C. for 5 hours. The calcined particles were classified to recover 120 μm or finer ones as the target catalyst.

Analysis of thus obtained catalyst gave the composition as $CuO:ZnO:Al_2O_3$=31:16:53 (by weight).

Example 2

Each of 37.1 g of copper nitrate ($Cu(NO_3)_2 \cdot 3H_2O$), 23.4 g of zinc nitrate ($Zn(NO_3)_2 \cdot 6H_2O$), and 10.3 g of aluminum nitrate ($Al(NO_3)_3 \cdot 9H_2O$) were dissolved into about 200 ml of ion-exchanged water. To the solution, 100 g of fine powder of γ-alumina (N612, Nikki Kagaku Co.) having: an approximate particle size of 20 μm or less was added. The water of the mixture was removed by vaporizing in a water-bath. The resultant material was put into about 1 liter of about 1 mole/liter aqueous ammonia. The mixture was held for about 1 hour. Then the mixture was further washed until no ammonium ion nor nitric acid ion was detected anymore. The mixture was dried at 120° C. for 24 hours. followed by calcined in air at 350° C. for 5 hours. The calcined particles were classified to recover 120 μm or finer ones as the target catalyst.

Analysis of thus obtained catalyst gave the composition as $CuO:ZnO:Al_2O_3$=20:11:69 (by weight).

Example 3

Each of 92.6 g of copper nitrate ($Cu(NO_3)_2 \cdot 3H_2O$), 58.5 g of zinc nitrate ($Zn(NO_3)_2 \cdot 6H_2O$), and 25.5 g of aluminum nitrate ($Al(NO_3)_3 \cdot 9H_2O$) were dissolved into about 500 ml of ion-exchanged water. To the solution, 100 g of fine powder of γ-alumina (N612, Nikki Kagaku Co.) having an approximate particle size of 20 μm or less was added. The water of the mixture was removed by vaporizing in a water-bath. The resultant material was put into about 1 liter of about 2.5 mole/liter aqueous ammonia. The mixture was held for about 1 hour. Then the mixture was further washed until no ammonium ion nor nitric acid ion was detected anymore. The mixture was dried at 120° C. for 24 hours. followed by calcined in air at 350° C. for 5 hours. The calcined particles were classified to recover 120 μm or finer ones as the target catalyst.

Analysis of thus obtained catalyst gave the composition as $CuO:ZnO:Al_2O_3$=31:16:53 (by weight).

Example 4

Each of 185 g of copper nitrate ($Cu(NO_3)_2 \cdot 3H_2O$), 117 g of zinc nitrate ($Zn(NO_3)_2 \cdot 6H_2O$), and 52 g of aluminum nitrate ($Al(NO_3)_3 \cdot 9H_2O$) were dissolved into about 1 liter of ion-exchanged water. To the solution, 50 g of fine powder of γ-alumina (N612, Nikki Kagaku Co.) having an approximate particle size of 20 μm or less was added. The water of the mixture was removed by vaporizing in a water-bath. The resulted material was put into about 1 liter of about 5 mole/liter aqueous ammonia. The mixture was held for about 1 hour. Then the mixture was further washed until no ammonium ion nor nitric acid ion was detected anymore. The mixture was dried at 120° C. for 24 hours. followed by calcined in air at 350° C. for 5 hours. The calcined particles were classified to recover 120 μm or finer ones as the target catalyst.

Analysis of thus obtained catalyst gave the composition as $CuO:ZnO:Al_2O_3$=41:21:38 (by weight).

Example 9

Each of 185 g of copper nitrate ($Cu(NO_3)_2 \cdot 3H_2O$), 117 g of zinc nitrate ($Zn(NO_3)_2 \cdot 6H_2O$), and 52 g of aluminum nitrate ($Al(NO_3)_3 \cdot 9H_2O$) were dissolved into about 1 liter of ion-exchanged water. To the solution, 100 g of fine powder of γ-alumina (N612, Nikki Kagaku Co.) having an approximate particle size of 20 μm or less was added. The water of the mixture was removed by vaporizing in a water-bath. The resulted material was put into about 1 liter of about 10 mole/liter aqueous solution of urea. The mixture was heated to about 90° C. under agitation. At the point that pH value reached to about 8, the mixture was allowed to stand for cooling. Then the mixture was filtered, and the cake was rinsed. The cake was dried at 120° C. for 24 hours. followed by calcined in air at 350° C. for 5 hours. The calcined particles were classified to recover 120 μm or finer ones as the target catalyst.

Analysis of thus obtained catalyst gave the composition as $CuO:ZnO:Al_2O_3 = 31:16:53$ (by weight).

II. Method for Activating Catalyst and Reaction Method

A 24 g of n-hexadecane (31.1 ml) was charged to a bubble-tower reactor having 2 cm of inside diameter and 2 m of height, and 3.6 g of each of the above-described catalyst powders was added to make the contents of the reactor in a suspended state. In Examples 5 through 8, the catalyst of Example 1 was used. A mixed gas of hydrogen, carbon monoxide, and nitrogen (at a molar ratio $H_2:CO:N_2$ of 1:1:9) was introduced to pass through the bubble-tower at a flow rate of about 300 ml/min. While flowing the mixed gas through the bubble-tower, the temperature in the bubble-tower was aradually raised from room temperature to 220° C. within a period of several hours. At the same time, the concentration of nitrogen in the mixed gas was gradually reduced to a final level of zero. Then, the reaction system was held at 220° C. for about 3 hours. to activate the catalyst.

The reaction was conducted at a specified temperature and pressure while introducing the mixed gas of hydrogen, carbon monoxide, and carbon dioxide at a molar ratio of $H_2CO/CO_2 = 47.5/47.5/5.0$ and at a flow rate of 336 ml/min. (converted at a condition of normal temperature and pressure).

The obtained reaction products and non-reacted substances were analyzed by gas chromatography.

III. Reaction Conditions and Experimental Results

The reaction conditions and experimental results are shown in Tables 6 through 8.

TABLE 6

| | Example 1 | Example 2 | Example 3 | Example 4 |
|---|---|---|---|---|
| Condition | | | | |
| Temperature (° C.) | 280 | 280 | 280 | 280 |
| Pressure (kg/cm²-G) | 30 | 30 | 30 | 30 |
| Reaction Result | | | | |
| CO conversion (%) | 41.3 | 27.1 | 30.3 | 38.6 |
| Yield (C-mol %) | | | | |
| Dimethyl ether | 31.5 | 20.9 | 24.1 | 27.3 |
| Methanol | 1.8 | 0.7 | 1.4 | 2.0 |
| Hydrocarbons | 0.1 | 0.2 | 0.2 | 0.1 |
| $CO_2$ | 7.9 | 5.3 | 4.6 | 9.1 |
| Dimethyl ether space time yield (g/kg-cat · h) | 861 | 572 | 659 | 747 |

TABLE 7

| | Example 5 | Example 6 | Example 7 | Example 8 |
|---|---|---|---|---|
| Condition | | | | |
| Temperature (° C.) | 250 | 300 | 280 | 280 |
| Pressure (kg/cm²-G) | 30 | 30 | 20 | 50 |
| Reaction Result | | | | |
| CO conversion (%) | 29.5 | 38.4 | 32.2 | 45.6 |
| Yield (C-mol %) | | | | |
| Dimethyl ether | 23.8 | 32.4 | 24.6 | 33.2 |
| Methanol | 2.1 | 1.1 | 0.8 | 1.7 |
| Hydrocarbons | 0.1 | 0.6 | 0.1 | 0.5 |
| $CO_2$ | 3.5 | 4.3 | 6.7 | 10.2 |
| Dimethyl ether space time yield (g/kg-cat · h) | 651 | 886 | 673 | 908 |

TABLE 8

| | Example 9 |
|---|---|
| Condition | |
| Temperature (° C.) | 280 |
| Pressure (kg/cm²-G) | 30 |
| Reaction Result | |
| CO conversion (%) | 40.8 |
| Yield (C-mol %) | |
| Dimethyl ether | 30.7 |
| Methanol | 1.7 |
| Hydrocarbons | 0.2 |
| $CO_2$ | 8.2 |
| Dimethyl ether space time yield (g/kg-cat · h) | 840 |

The catalyst for manufacturing dimethyl ether according to the present invention provides effects of preventing separation of individual catalyst ingredients from each other during reaction, of assuring smooth progress of reaction cycle, and of achieving high dimethyl ether yield owing to the configuration thereof comprising an alumina having micropores with deposits of copper oxide, zinc oxide, and alumina therein.

The method for manufacturing dimethyl ether according to the present invention uses a slurry of solvent with a catalyst comprising an alumina having micropores with deposits of copper oxide, zinc oxide, and alumina therein, so the method provides effects of achieving high space time yield of dimethyl ether, of being free from problems of plugging of catalyst and of mechanical strength of catalyst, of easiness for removing reaction heat and for controlling reaction heat, of assuring wide application range of the ratio of carbon monoxide to hydrogen, of progress of reaction under the presence of high concentration of carbon dioxide, and of less influence of impurities and catalyst poisons.

Embodiment 3

The catalyst for manufacturing dimethyl ether according to the present invention is characterized in that at least a methanol synthesis catalyst and a methanol-dehydration catalyst are integrated together using a binder.

The method for manufacturing dimethyl ether according to the present invention comprises the step of charging a mixed gas of carbon monoxide and hydrogen, or a mixed gas of carbon monoxide, hydrogen, and further containing carbon dioxide and/or water vapor to a slurry of the catalyst with a solvent.

The catalyst according to the present invention is basically a catalyst in which a methanol synthesis catalyst, a methanol-dehydration catalyst, and a water gas shift catalyst are integrated together. Since, however, the methanol synthesis catalyst is inherently an excellent water gas shift catalyst, the methanol synthesis catalyst may play a role of the water gas shift catalyst.

The methanol synthesis catalyst may be copper oxide-zinc oxide-alumina system and zinc oxide-chromium oxide-alumina system. A preferable mixing ratio of individual ingredients of copper oxide, zinc oxide, and alumina is: in an approximate range of from 0.05 to 20 wt.parts of zinc oxide to 1 wt.parts of copper oxide, more preferably in an approximate range of from 0.1 to 5 wt.parts; in an approximate range of from 0 to 2 wt.parts of alumina, more preferably in an approximate range of from 0 to 1 wt.parts. A preferable mixing ratio of individual ingredients of zinc oxide, chromium oxide, and alumina is: in an approximate range of from 0.1 to 10 of chromium oxide to 1 wt.parts of zinc oxide, more preferably in an approximate range of from 0.5 to 5; and in an approximate range of from 0 to 2 wt.parts of alumina, more preferably in an approximate range of from 0 to 1 wt.parts. Applicable methanol-dehydration catalysts includes γ-alumina, silica-alumina, and zeolite. Examples of metallic oxide ingredient in zeolite are oxide of alkali metal such as sodium and potassium, and oxide of alkali earth metal such as calcium and magnesium. As described above, the methanol synthesis catalyst may substitute for the water gas shift catalyst. Other than the methanol synthesis catalyst, iron oxide-chromium oxide may substitute for the water gas shift catalyst. A preferable ratio of chromium oxide to iron oxide is in an approximate range of from 0.1 to 20 wt.parts to 1 wt.parts of iron oxide, more preferably in an approximate range of from 0.5 to 10.

Each of these methanol synthesis catalyst, methanol-dehydration catalyst, and water gas shift catalyst may be manufactured by known methods. For example, a water soluble salt of each metallic ingredient is used to prepare an aqueous solution containing these salts. The kind of salt is either inorganic salt or organic salt. Nevertheless, a salt that likely generates hydroxide in water is not suitable. Nitrate, carbonate, organic acid salt, and halide are applicable as the salt. A preferable concentration of each ingredient is in an approximate range of from 0.1 to 3 mole/liter. A base is added to the aqueous solution to neutralize the solution and to precipitate hydroxide. Then the solid is separated from liquid, which is then rinsed and dried, followed by calcining to obtain the target catalyst. Alternatively, a commercial catalyst may be used.

The mixing ratio of above-described methanol synthesis catalyst, methanol-dehydration catalyst, and water gas shift catalyst is not specifically limited, and is selected at an adequate ratio corresponding to the kind of each ingredient and the reaction condition. A preferable mixing ratio is often in an approximate range of from 0.5 to 10 wt.parts of methanol-dehydration catalyst per 1 wt.parts of methanol synthesis catalyst, and in an approximate range of from 0 to 5 wt.parts of water gas shift catalyst per 1 wt.parts of methanol synthesis catalyst.

These catalysts are co-pulverized, or pulverized in a mixed state. Co-pulverization is preferably done to an approximate average particle size of 200 μm or less, more preferably in an approximate range of from 1 to 100 μm, and most preferably in an approximate range of from 1 to 50 μm.

Thus prepared catalyst mixture particles are blended with a binder. The binder needs to have characteristics of durability to calcining (alteration is acceptable), function to bind individual catalysts to integrate them after calcining, and not degrading the activity of each catalyst. Alumina sol and clay are examples of the binder. A preferable ratio of binder to catalyst is in a range of from 0.005 to 1 wt.parts to 1 wt.parts of catalyst, more preferably in a range of from 0.01 to 1, and most preferably in a range of from 0.05 to 1.

After the co-pulverization, the mixture is processed by drying and calcining. The calcining may be carried out at a temperature ranging approximately from 250 to 500° C. for a period of approximately from 2 to 10 hours.

After the calcining, the mixture is pulverized for use. Preferably, the pulverization is conducted to an average particle size of 200 μm or less, more preferably to an approximate range of from 1 to 100 μm, and most preferably to an approximate range of from 1 to 50 μm.

Thus prepared catalyst achieves 35% or higher CO conversion, normally in an approximate range of from 40 to 60%, and particularly in an approximate range of from 50 to 60%, and achieves 25% or higher dimethyl ether yield, or normally in an approximate range of from 30 to 40%.

A primary characteristic of the method according to the present invention is to integrate a methanol synthesis catalyst, a methanol-dehydration catalyst, and a water gas shift catalyst using a binder. The integration is conducted for ensuring swift progress of the reaction cycle described below by making the distance among these catalysts very short, so that the catalysts are very close to each other without separating them from each other during the reaction period, thus improving the yield of dimethyl ether. That is, the reaction proceeds in the sequent order of: yielding methanol on the methanol synthesis catalyst from carbon monoxide and hydrogen; moving the methanol onto the methanol-dehydration catalyst to yield dimethyl ether and water by dehydration-condensation; moving the water onto the water gas shift catalyst and/or the methanol synthesis catalyst to yield hydrogen by reacting with carbon monoxide. The reaction is expressed by the formulae given below.

$$CO + 2H_2 \rightarrow CH_3OH$$

$$2CH_3OH \rightarrow CH_3OCH_3 + H_2O$$

$$CO + H_2O \rightarrow CO_3 + H_2$$

The above-described catalyst is used in a state of slurry of a solvent. The amount of catalyst in the solvent depends on the kind of the solvent, the reaction conditions, and other variables. Normally, the amount of catalyst is in a range of from 1 to 50 wt. % to the amount of the solvent.

The kind of solvent used for synthesizing dimethyl ether according to the present invention is arbitrarily selected if only the solvent is in a liquid phase under the reaction condition. Examples of the solvent are hydrocarbons of aliphatic, aromatic, and alicyclic groups, alcohol, ether, ester, ketone, halide, or their mixture.

Alternatively, gas oil after removing sulfur ingredients, vacuum gas oil, high boiling point distillates of coal tar after treated by hydrogenation are also applicable as the solvent.

By passing a mixed gas of carbon monoxide and hydrogen through thus prepared slurry of catalyst with solvent, dimethyl ether is obtained at a high yield. Applicable range of molar mixing ratio of hydrogen to carbon monoxide ($H_2$/CO) is wide, for instance, in a range of from 20 to 0.1 as ($H_2$/CO), and more preferably from 10 to 0.2.

According to the reaction system, the mixed gas does not directly contact with the catalyst, which direct contact occurs in a gas-solid catalytic reaction system, but the carbon monoxide and hydrogen contact with catalyst only after being dissolved into a solvent. Consequently, selection of an adequate kind of solvent taking into account of the solubility of carbon monoxide and hydrogen to the solvent establishes a constant composition of carbon monoxide and hydrogen in the solvent independent of the gas composition, and sustains the supply of the mixed gas at an established composition to the catalyst surface.

In the case of a mixed gas with a significantly low ratio of ($H_2$/CO), for example, 0.1 or less, or in the case of solely carbon monoxide without containing hydrogen, it is necessary to separately supply steam to convert a part of the carbon monoxide into hydrogen and carbon dioxide within the reactor.

Since solvent exists between the raw material gases and the catalyst, the gas composition does not necessarily agree with the composition on the catalyst surface. Therefore, it is acceptable that the mixed gas of carbon monoxide and hydrogen, or solely carbon monoxide gas includes a relatively high concentration of carbon dioxide (in a range of from 20 to 50%).

The manufacturing method according to the present invention significantly reduces the effect of ingredients that may act as a catalyst-poison on the catalyst compared with the gas-solid contact catalyst system. Examples of the catalyst-poisoning ingredients which may exist in the raw material gas are sulfur compounds such as hydrogen sulfide, cyan compounds such as hydrogen cyanide, and chlorine compounds such as hydrogen chloride. Even when the catalyst activity is decreased as a result of poisoning, the productivity of total reactor system is maintained at a constant level by withdrawing the slurry from the reactor and by charging fresh slurry containing catalyst of high activity to the reactor.

The reaction heat is recovered in a form of medium pressure steam using a cooling coil installed inside of the reactor while passing hot water through the cooling coil. The cooling system controls the reaction temperature at an arbitrary level.

A preferable reaction temperature is in a range of from 150 to 400° C., and particularly preferable in a range of from 200 to 350° C. The reaction temperature below 150° C. and above 400° C. degrades the conversion of carbon monoxide.

A preferable reaction pressure is in a range of from 10 to 300 kg/cm$^2$, and particularly preferable in a range of from 15 to 150 kg/cm$^2$. The reaction pressure below 10 kg/cm$^2$ results in a low conversion of carbon monoxide, and that above 300 kg/cm$^2$ requires a special design of the reactor and is uneconomical because of the need of a large amount of energy for pressurizing the system.

A preferable space velocity (charge rate of mixed gas per 1 g of catalyst under standard condition) is in a range of from 100 to 50000 ml/g·h, and particularly preferable from 500 to 30000 ml/g·h. The space velocity above 50000 ml/g·h degrades the conversion of carbon monoxide, and that below 100 ml/g·h is uneconomical because of the need of an excessively large reactor.

The catalyst for manufacturing dimethyl ether according to the present invention and a method therefor apply integration of a methanol synthesis catalyst, a methanol-dehydration catalyst, and a water gas shift catalyst with a binder, so the individual catalyst ingredients do not separate from each other during the reaction period. As a result, the reaction cycle proceeds smoothly and a high dimethyl ether yield is achieved.

The method for manufacturing dimethyl ether according to the present invention significantly increases the yield of dimethyl ether by using the catalyst which comprises an integrated condition of a methanol synthesis catalyst, a methanol-dehydration catalyst, and a water gas shift catalyst, in a state of a slurry with a solvent. The method is free from problems such as plugging of catalyst and mechanical strength of catalyst, is designed to readily absorb the reaction heat through a cooling pipe or the like, and is designed to conduct withdrawing and filling of catalyst easily.

EXAMPLE

I. Preparation of Catalyst

1) Preparation of CuO—ZnO—$Al_2O_3$ Catalyst

Each of 185 g of copper nitrate ($Cu(NO_3)_2.3H_2O$), 117 g of zinc nitrate ($Zn(NO_3)_2.6H_2O$), and 52 g of aluminum nitrate ($Al(NO_3)_3.9H_2O$) were dissolved into about 1 liter of ion-exchanged water. Separately, about 1.4 kg of sodium carbonate ($Na_2CO_3$) was dissolved into about 1 liter of ion-exchanged water. Both of the solutions were added dropwise to about 3 liters of ion-exchanged water in a stainless steel vessel which was controlled at about 60° C. within about 2 hours, while maintaining the contents to pH 7.0±0.5. Then, the contents were allowed to stand for about 1 hour for aging. When, during the treatment, the pH value went out from a range of pH 7.0±0.5, either of an aqueous solution of about 1 mole/liter nitric acid or an aqueous solution of about 1 mole/liter sodium carbonate was added dropwise to keep the range of pH 7.0±0.5. The resultant precipitate was filtered, and the cake was rinsed by ion-exchanged water until nitric acid ion was not detected anymore. After the rinse, the cake was dried at 120° C. for 24 hours. followed by calcining thereof in air at 350° C. for 5 hours to obtain the target methanol synthesis catalyst.

Analysis of thus obtained catalyst gave the composition as CuO:ZnO:$Al_2O_3$=31:32:7 (by weight).

2) Preparation of CuO—$Cr_2O_3$—ZnO Catalyst

Each of 0.30 kg of copper nitrate ($Cu(NO_3)_2.3H_2O$), 105 g of chromium nitrate ($Cr(NO_3)_2.3H_2O$), and 256 g of zinc nitrate ($Zn(NO_3)_2.6H_2O$) were dissolved into about 1 liter of ion-exchanged water. Separately, about 130 g of sodium carbonate ($Na_2CO_3$) was dissolved into about 1 liter of ion-exchanged water. Both of the solutions were added dropwise to about 3 liters of ion-exchanged water in a stainless steel vessel which was controlled at about 60° C. within about 2 hours while maintaining the contents to pH 8.5±0.5. Then, the contents were allowed to stand for about 1 hr for aging. When, during the treatment, the pH value went out from a range of pH 8.5±0.5, either of an aqueous solution of about 1 mole/liter nitric acid or an aqueous solution of about 1 mole/liter sodium carbonate was added dropwise to keep the range of pH 8.5±0.5. The resultant precipitate was filtered, and the cake was rinsed by ion-exchanged water until nitric acid ion was not detected anymore. After the rinse, the cake was dried at 120° C. for 24 hours followed by calcining thereof in air at 350° C. for 5 hours to obtain the target methanol synthesis catalyst.

Analysis of thus obtained catalyst gave the composition as CuO:$Cr_2O_3$:ZnO=1:2:3 (by weight).

3) Preparation of Cu—$Al_2O_3$ Catalyst

A 15.7 g of copper acetate ($Cu(CH_3COO)_2.H_2O$) was dissolved into about 200 ml of ion-exchanged water. A 95 g of γ-alumina (N612, Nikki Kagaku Co.) was further added to the mixture. The mixture was then vaporized to dry. The dried material was further dried in air at 120° C. for 24 hours, followed by calcining in air at 450° C. for 4 hours. The calcined material was treated in hydrogen gas stream at 400° C. for 3 hours to obtain a catalyst. Analysis of the catalyst gave the composition as Cu:$Al_2O_3$=5:95 (by weight).

Examples 1, 3, and 4

An 100 g aliquot of CuO—ZnO—$Al_2O_3$ catalyst prepared in the above treatment, 50 g of commercially available alumina (N612, Nikki Kagaku Co.), and a 50 g aliquot of CuO—$Cr_2O_3$—ZnO catalyst prepared in the above treatment were pulverized together in a ball mill for about 3 hours to a fine powder having about 20 μm or less of particle size. A 50 g of alumina sol (Alumina sol-520, Nissan Chemical Industries, Ltd.) was added to the catalyst powder to uniformly mix them together. The mixture was dried in air at 120° C. for 24 hours followed by calcining in air at 450° C. for 3 hours to unify these ingredients. The calcined material was pulverized to 120 μm or smaller particle size to obtain a catalyst.

Example 2

A 200 g aliquot of CuO—ZnO—$Al_2O_3$ catalyst prepared in the above treatment, 50 g of commercially available alumina (N612, Nikki Kagaku Co.), and a 50 g aliquot of CuO—$Cr_2O_3$—ZnO catalyst prepared in the above treatment were pulverized together in a ball mill for about 3 hours to a fine powder having about 20 μm or less of particle size. A 50 g of alumina sol (Alumina sol-520, Nissan Chemical Industries, Ltd.) was added to the catalyst powder to uniformly mix them together. The mixture was dried in air at 120° C. for 24 hours followed by calcining in air at 450° C. for 3 hours to unify these ingredients. The calcined material was pulverized to 120 μm or smaller particle size to obtain a catalyst.

Examples 5, 7, 8, 9, and 10

An 100 g aliquot of CuO—ZnO—$Al_2O_3$ catalyst prepared in the above treatment and a 50 g aliquot of Cu—$Al_2O_3$ catalyst prepared in the above treatment were-pulverized together in a ball mill for about 3 hours to a fine powder having about 20 μm or less of particle size. A 50 g of alumina sol (Alumina sol-520, Nissan Chemical Industries, Ltd.) was added to the catalyst powder to uniformly mix them together. The mixture was dried in air at 120° C. for 24 hours followed by calcining in air at 450° C. for 3 hours to unify these ingredients. The calcined material was pulverized to 120 μm or smaller particle size to obtain an integrated catalyst.

Example 6

A 200 g aliquot of CuO—ZnO—$Al_2O_3$ catalyst prepared in the above treatment and a 50 g aliquot of Cu—$Al_2O_3$ catalyst prepared in the above treatment were pulverized together in a ball mill for about 3 hours to a fine powder having about 20 μm or less of particle size. A 50 g of alumina sol (Alumina sol-520, Nissan Chemical Industries, Ltd.) was added to the catalyst powder to uniformly mix them together. The mixture was dried in air at 120° C. for 24 hours, followed by calcining in air at 450° C. for 3 hours to unify these ingredients. The calcined material was pulverized to 120 μm or smaller particle size to obtain an integrated catalyst.

Example 11

An 100 g aliquot of CuO—ZnO—$Al_2O_3$ catalyst prepared in the above treatment, 50 g of commercially available alumina (N612, Nikki Kagaku Co.), and a 50 g aliquot of CuO—$Cr_2O$—ZnO catalyst prepared in the above treatment were pulverized together in a ball mill for about 3 hours to a fine powder having about 20 μm or less of particle size. A 50 g of clay (Kunipia, Kunimine Kogyo Co.) was added to the catalyst powder to uniformly mix them together. The mixture was dried in air at 120° C. for 24 hours followed by calcining in air at 450° C. for 3 hours to unify these ingredients. The calcined material was pulverized to 120 μm or smaller particle size to obtain a catalyst.

Comparative Example

An 100 g aliquot of CuO—ZnO—$Al_2O_3$ catalyst prepared in the above treatment, 50 g of commercially available alumina (N612, Nikki Kagaku Co.), and a 50 g aliquot of CuO—$Cr_2O_3$—ZnO catalyst prepared in the above treatment were pulverized together in a ball mill for about 3 hours to a fine powder having about 20 μm or less of particle size. The mixture was calcined in air at 450° C. for 3 hours. The calcined material was pulverized to 120 μm or smaller particle size to obtain a catalyst.

II. Method for Activating Catalyst and Reaction Method

A 24 g of n-hexadecane (31. 1 ml) was charged to a bubble-tower reactor having 2 cm of inside diameter and 2 m of height, and 3.6 g of each of the above-described catalyst powders was added to make the contents of the reactor in a suspended state. A mixed gas of hydrogen, carbon monoxide, and nitrogen (at a molar ratio $H_2:CO:N_2$ of 1:1:9) was introduced to pass through the bubble-tower at a flow rate of about 300 ml/min. While flowing the mixed gas through the bubble-tower, the temperature in the bubble-tower was gradually raised from room temperature to 220° C. within a period of several hours. At the same time, the concentration of nitrogen in the mixed gas was gradually reduced to a final level of zero. Then, the reaction system was held at 220° C. for about 3 hours to activate the catalyst.

The reaction was conducted at a specified temperature and pressure while introducing the mixed gas of hydrogen, carbon monoxide, and carbon dioxide at a molar ratio of $H_2/CO/CO_2$=47.5/47.5/5.0 and at a flow rate of 336 ml/min. (converted at a condition of normal temperature and pressure).

The obtained reaction products and non-reacted substances were analyzed by gas chromatography.

III. Reaction Conditions and Experimental Results

The reaction conditions and experimental results are shown in Tables 9 and 10.

TABLE 9

| | | Example 1 | Example 2 | Example 3 | Example 4 | Example 5 | Example 6 |
|---|---|---|---|---|---|---|---|
| Condition | Temperature (° C.) | 280 | 280 | 250 | 300 | 280 | 280 |
| | Pressure (kg/cm²-G) | 30 | 30 | 30 | 30 | 30 | 30 |

TABLE 9-continued

|  |  | Example 1 | Example 2 | Example 3 | Example 4 | Example 5 | Example 6 |
|---|---|---|---|---|---|---|---|
| Reaction Result | CO conversion (%) | 51.7 | 48.3 | 45.4 | 47.1 | 52.9 | 51.3 |
|  | Yield Dimethyl ether | 35.2 | 31.4 | 27.7 | 29.6 | 35.8 | 33.9 |
|  | (C-mol %) Methanol | 2.1 | 5.3 | 6.9 | 1.8 | 2.4 | 2.6 |
|  | Hydrocarbons | 0.5 | 0.6 | 0.4 | 3.0 | 0.8 | 1.3 |
|  | $CO_2$ | 14.0 | 11.1 | 10.4 | 12.7 | 13.9 | 13.5 |
|  | Dimethyl ether space time yield (g/kg-cat · h) | 963 | 859 | 758 | 809 | 979 | 927 |

TABLE 10

|  |  | Example 7 | Example 8 | Example 9 | Example 10 | Example 11 | Comparative Example |
|---|---|---|---|---|---|---|---|
| Condition | Temperature (° C.) | 260 | 300 | 280 | 280 | 280 | 280 |
|  | Pressure (kg/cm²-G) | 30 | 30 | 20 | 50 | 30 | 30 |
| Reaction Result | CO conversion (%) | 46.5 | 50.4 | 38.8 | 57.1 | 44.8 | 32.4 |
|  | Yield Dimethyl ether | 25.1 | 33.9 | 27.2 | 37.1 | 29.5 | 22.9 |
|  | (C-mol %) Methanol | 5.9 | 2.2 | 3.1 | 2.9 | 3.1 | 1.1 |
|  | Hydrocarbons | 0.3 | 3.3 | 0.5 | 1.7 | 0.6 | 0.2 |
|  | $CO_2$ | 15.2 | 11.0 | 8.0 | 15.4 | 11.6 | 8.2 |
|  | Dimethyl ether space time yield (g/kg-cat · h) | 686 | 927 | 744 | 1015 | 807 | 626 |

The catalyst for manufacturing dimethyl ether according to the present invention provides effects of preventing separation of individual catalyst ingredients from each other during reaction, of assuring smooth progress of reaction cycle, and of achieving high dimethyl ether yield owing to the configuration thereof comprising a methanol synthesis catalyst, a methanol-dehydration catalyst, and a water gas shift-catalyst being integrated together using a binder.

The method for manufacturing dimethyl ether according to the present invention uses a slurry of solvent with a catalyst comprising a methanol synthesis catalyst, a methanol-dehydration catalyst, and a water gas shift catalyst being integrated together using a binder, so the method provides effects of achieving high space time yield of dimethyl ether, of being free from problems of plugging of catalyst and of mechanical strength of catalyst, of easiness for removing reaction heat and for controlling reaction heat, of assuring wide application range of the ratio of carbon monoxide to hydrogen, of progress of reaction under the presence of high concentration of carbon dioxide, and of less influence of impurities and catalyst poisons.

Embodiment 4

The inventors developed a method for manufacturing a catalyst to produce dimethyl ether, which method comprises: suspending a methanol synthesis catalyst, a methanol-dehydration catalyst, and a water gas shift catalyst in a solvent while maintaining the difference in an A value within $\pm 1 \times 10^{-6}$ g/cm among the methanol synthesis catalyst, the methanol-dehydration catalyst, and the water gas shift catalyst, wherein the A is defined by an equation of $A=D^2(P-S)$, where D denotes average particle size of catalyst concerned, (cm), P denotes particle density of catalyst concerned, (g/cm³), and S denotes solvent density, (g/cm³). The inventors found that the use of thus prepared catalyst in a slurry state achieved the production of dimethyl ether at a high yield and a high space time yield from a mixed gas of carbon monoxide and hydrogen, or further containing carbon dioxide and/or water vapor. Thus the inventors completed the present invention.

According to the present invention, each of the methanol synthesis catalyst, the methanol-dehydration catalyst, and the water gas shift catalyst is prepared under a control of the particle density and the particle size, then they are mixed together by a physical means. As a result, the method according to the present invention ensures prompt progress of the reaction described below to improve the yield of dimethyl ether by making the distance among these catalysts close to each other while preventing separation thereof during the reaction period. That is, the reaction proceeds in sequent order of: yielding methanol on the methanol synthesis catalyst from carbon monoxide and hydrogen; moving the methanol onto the methanol-dehydration catalyst to yield dimethyl ether and water by dehydration-condensation; moving the water onto the water gas shift catalyst and/or the methanol synthesis catalyst to yield hydrogen by the reaction of the water with carbon monoxide. The reaction is expressed by the formulae given below.

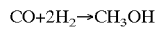

$$CO+2H_2 \rightarrow CH_3OH$$

$$2CH_3OH \rightarrow CH_3OCH_3+H_2O$$

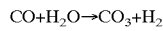

$$CO+H_2O \rightarrow CO_3+H_2$$

The catalyst according to the present invention basically comprises a methanol synthesis catalyst, a methanol-dehydration catalyst, and a water gas shift catalyst. Since, however, the methanol synthesis catalyst is inherently an excellent water gas shift catalyst, the methanol synthesis catalyst may function also the water gas shift catalyst.

Methanol synthesis catalyst may be copper oxide-zinc oxide-alumina system and zinc oxide-chromium oxide-alumina system. A preferable mixing ratio of individual ingredients of copper oxide, zinc oxide, and alumina is: in an approximate range of from 0.05 to 20 wt.parts of zinc oxide to 1 wt.parts of copper oxide, more preferably in an approximate range of from 0.1 to 5 wt.parts; in an approximate range of from 0 to 2 wt.parts of alumina, more preferably in an approximate range of from 0 to 1 wt.parts. A preferable mixing ratio of individual ingredients of zinc oxide, chromium oxide, and alumina is: in an approximate range of from 0.1 to 10 of chromium oxide to 1 wt.parts of zinc oxide, more preferably in an approximate range of from 0.5 to 5; and in an approximate range of from 0 to 2 wt.parts of alumina, more preferably in an approximate range of from 0 to 1 wt.parts. Applicable methanol-dehydration catalysts includes γ-alumina, silica-alumina, and zeolite. Examples of metallic oxide ingredient in zeolite are oxide of alkali metal such as sodium and potassium, and oxide of alkali earth metal such as calcium and magnesium. Examples of water gas shift catalyst are a copper oxide-zinc oxide system and an iron oxide-chromium oxide system. A preferable ratio of copper oxide to zinc oxide is in an approximate range of from 0.1 to 20 wt.parts of copper oxide to 1 wt.parts of iron oxide, more preferably in an approximate range of from 0.5 to 10. A preferable ratio of iron oxide to chromium oxide is in an approximate range of from 0.1 to 20 wt.parts of chromium oxide to 1 wt.parts of iron oxide, more preferably in an approximate range of from 0.5 to 10. A copper (including copper oxide) -alumina system is a catalyst which functions both as a methanol-dehydration catalyst and as a water gas shift catalyst.

Each of these methanol synthesis catalyst, methanol-dehydration catalyst, and water gas shift catalyst may be manufactured by known methods. For example, a water soluble salt of each metallic ingredient is used to prepare an aqueous solution containing these salts. The kind of salt is either an inorganic salt or an organic salt. Nevertheless, a salt that likely generates hydroxide in water is not suitable. Nitrate, carbonate, organic acid salt, and halide are applicable as the salt. A preferable concentration of each ingredient is in an approximate range of from 0.1 to 3 mole/l. A base is added to the aqueous solution to neutralize thereof and to precipitate hydroxide. Then the solid is separated from liquid, which is then rinsed and dried, followed by calcining to obtain the tar get catalyst. Alternatively, a commercial catalyst may be used.

The mixing ratio of the above-described methanol synthesis catalyst, methanol-dehydration catalyst, and water gas shift catalyst is not specifically limited, and is selected at an adequate ratio corresponding to the kind of each ingredient and the reaction condition. A preferable mixing ratio is often in an approximate range of from 0.5 to 10 wt.parts of methanol-dehydration catalyst per 1 wt.parts of methanol synthesis catalyst, and in an approximate range of from 0 to 5 wt.parts of water gas shift catalyst per 1 wt.parts of methanol synthesis catalyst.

A preferable difference in value of A that is derived from the above-described equation among individual catalyst types is within $\pm 1\times 10^{-6}$ g/cm which was given before, and more preferably within $\pm 5\times 10^{-7}$ g/cm. If the difference in A value exceeds $\pm 1\times 10^{-6}$, then the conversion of carbon monoxide decreases. The method for controlling the value A is not specifically limited. Generally, however, the control is carried out based mainly on the average particle size and the particle density of catalyst concerned because the density of solvent shows no significant change. If only the average particle size is kept constant, the particle density does not show significant change. Accordingly, the control of average particle size is a simple control method. Pulverization by ball mill is a method for controlling the average particle size. The determination of average particle size is done by sieve method (JIS Z8801-1982), sedimentation method, or other methods. The determination of particle density is carried out by picnometer method (JIS R-5201) and buoyancy method (JIS R6125).

The catalyst is used as a slurry with a solvent. The amount of catalyst in the solvent depends on the kind of the solvent, the reaction conditions, and other variables. Normally, the amount of catalyst is in a range of from 1 to 50 wt. % to the amount of the solvent.

The kind of solvent used for synthesizing dimethyl ether according to the present invention is arbitrarily selected if only the solvent is in a liquid phase under the reaction condition. Examples of the solvent are hydrocarbons of aliphatic, aromatic, and alicyclic groups, alcohol, ether, ester, ketone, halide, or their mixture.

Alternatively, gas oil after removing sulfur ingredients, vacuum gas oil, high boiling point distillates of coal tar after treated by hydrogenation are also applicable as the solvent.

By passing a mixed gas of carbon monoxide and hydrogen through thus prepared slurry of catalyst with solvent, dimethyl ether is obtained at a high yield. Applicable range of molar mixing ratio of hydrogen to carbon monoxide ($H_2/CO$) is wide, for instance, in a range of from 20 to 0.1 as ($H_2/CO$), and more preferably from 10 to 0.2.

According to the reaction system, the mixed gas does not directly contact with the catalyst, which direct contact occurs in a gas-solid catalytic reaction system, but the carbon monoxide and hydrogen contact with catalyst only after dissolved into a solvent. Consequently, selection of an adequate kind of solvent taking into account of the solubility of carbon monoxide and hydrogen to the solvent establishes a constant composition of carbon monoxide and hydrogen in the solvent independent of the gas composition, and sustains the supply of the mixed gas at an established composition to the catalyst surface.

In the case of a mixed gas with a significantly low ratio of ($H_2/CO$), for example, 0.1 or less, or in the case of solely carbon monoxide without containing hydrogen, it is necessary to separately supply steam to convert a part of the carbon monoxide into hydrogen and carbon dioxide within the reactor.

Since solvent exists between the raw material gases and the catalyst, the gas composition does not necessarily agree with the composition on the catalyst surface. Therefore, it is acceptable that the mixed gas of carbon monoxide and hydrogen, or solely carbon monoxide gas includes a relatively high concentration of carbon dioxide (in a range of from 20 to 50%).

The manufacturing method according to the present invention significantly reduces. the effect of ingredients that may act as a catalyst-poison on the catalyst compared with the gas-solid contact catalyst system. Examples of the catalyst-poisoning ingredients which may exist in the raw material gas are sulfur compounds such as hydrogen sulfide, cyan compounds such as hydrogen cyanide, and chlorine compounds such as hydrogen chloride. Even when the catalyst activity is decreased as a result of poisoning, the productivity of the total reactor system is maintained at a constant level by withdrawing the slurry from the reactor and by charging fresh slurry containing catalyst of high activity to the reactor.

The reaction heat is recovered in a form of medium pressure steam using a cooling coil installed inside of the reactor while passing hot water through the cooling coil. The cooling system controls the reaction temperature at an arbitrary level.

A preferable reaction temperature is in a range of from 150 to 400° C., and particularly preferable in a range of from 200 to 350° C. The reaction temperature below 150° C. and above 400° C. degrades the conversion of carbon monoxide.

A preferable reaction pressure is in a range of from 10 to 300 kg/cm², and particularly preferable in a range of from 15 to 150 kg/cm². The reaction pressure below 10 kg/cm² results in a low conversion of carbon monoxide, and that above 300 kg/cm² requires special design of reactor and is uneconomical because of the need of a large amount of energy for pressurizing the system.

A preferable space velocity (charge rate of mixed gas per 1 g of catalyst under standard condition) is in a range of from 100 to 50000 ml/g·h, and particularly preferable from 500 to 30000 ml/g·h. The space velocity above 50000 ml/g·h degrades the conversion of carbon monoxide, and that below 100 ml/g·h is uneconomical because of the need of an excessively large reactor.

EXAMPLE

I. Preparation of Catalyst

1) Preparation of Catalyst [1]

Each of 185 g of copper nitrate ($Cu(NO_3)_2 3H_2O$), 117 g of zinc nitrate ($Zn(NO_3)_2 6H_2O$), and 52 g of aluminum nitrate ($Al(NO_3)_3 9H_2O$) were dissolved into about 1 liter of ion-exchanged water. Separately, about 200 g of sodium carbonate ($Na_2CO_3$) was dissolved into about 1 liter of ion-exchanged water. Both of the solutions were added dropwise to about 3 liters of ion-exchanged water in a stainless steel vessel which was controlled at about 60° C. within about 2 hours while maintaining the contents to pH 7.0±0.5. Then, the contents were allowed to stand for about 1 hour for aging. When, during the treatment, the pH value went out from a range of pH 7.0±0.5, either of an aqueous solution of about 1 mole/liter nitric acid or an aqueous solution of about 1 mole/liter sodium carbonate was added dropwise to keep the range of pH 7.0±0.5. The resulted precipitate was filtered, and the cake was rinsed by ion-exchanged water until nitric acid ion was not detected anymore. After the rinse, the cake was dried at 120° C. for 24 hours, followed by calcining thereof in air at 350° C. for 3 hours to obtain the catalyst [1].

Analysis of thus obtained catalyst [1] gave the composition as $CuO:ZnO:Al_2O_3=61:37:7$ (by weight).

2) Preparation of Catalyst [2]

Each of 91 g of copper nitrate ($Cu(NO_3)_2 3H_2O$) and 256 g of zinc nitrate ($Zn(NO_3)_2 6H_2O$) were dissolved into about 1 liter of ion-exchanged water. Separately, about 130 g of sodium carbonate ($Na_2CO_3$) was dissolved into about 1 liter of ion-exchanged water. Both of the solutions were added dropwise to about 3 liters of ion-exchanged water in a stainless steel vessel which was controlled at about 60° C. within about 2 hours, while maintaining the contents to pH 8.5±0.5. Then, the contents were allowed to stand for about 1 hr for aging. When, during the treatment, the pH value went out from a range of pH 8.5±0.5, either of an aqueous solution of about 1 mole/l nitric acid or an aqueous solution of about 1 mole/liter sodium carbonate was added dropwise to keep the range of pH 8.5±0.5. The resultant precipitate was filtered, and the cake was rinsed by ion-exchanged water until nitric acid ion was not detected anymore. After the rinse, the cake was dried at 120° C. for 24 hours, followed by calcining thereof in air at 350° C. for 3 hours to obtain the catalyst [2].

Analysis of thus obtained catalyst [2] gave the composition as $CuO:ZnO=3:7$ (by weight).

3) Preparation of Catalyst [3]

An 100 g of alumina (N612, Nikki Kagaku Co.) was dried in air at 120° C. for 24 hours, followed by calcining in air at 450° C. for 3 hours to obtain the target alumina catalyst [3].

4) Preparation of Catalyst [4]

A 15.7 g of copper acetate ($Cu(CH_3COO)_2H_2O$) was dissolved into about 200 ml of ion-exchanged water. A 95 g aliquot of alumina catalyst prepared in the step 3) was further added to the mixture. The mixture was then vaporized to dry. The dried material was further dried in air at 120° C. for 24 hours, followed by calcining in air at 450° C. for 3 hours. The calcined material was treated in hydrogen gas stream at 400° C. for 3 hours to obtain the catalyst [4]. Analysis of the catalyst gave the composition as $Cu:Al_2O_3=5:95$ (by weight).

5) Preparation of Catalyst [5]

A 736 g of aluminum nitrate ($Al(NO_3)_3 9H_2O$) was dissolved into about 2 liters of ion-exchanged water. Separately, about 350 g of sodium carbonate ($Na_2CO_3$) was dissolved into about 2 liters of ion-exchanged water. Both of the solutions were added dropwise to about 3 liters of ion-exchanged water in a stainless steel vessel at room temperature within about 2 hours while maintaining the contents to pH 7.5±0.5. Then, the contents were allowed to stand for about 1 hour for aging. When, during the treatment, the pH value went out from a range of pH 7.5±0.5, either of an aqueous solution of about 1 mole/liter nitric acid or an aqueous solution of about 1 mole/liter sodium carbonate was added dropwise to keep the range of pH 7.5±0.5. The resulted precipitate was filtered, and the cake was rinsed by ion-exchanged water until nitric acid ion was not detected anymore. After the rinse, the cake was dried at 120° C. for 24 hours, followed by calcining thereof in air at 350° C. for 3 hours to obtain alumina.

Then, 15.7 g of copper acetate ($Cu(CH_3COO)_2H_2O$) was dissolved into about 200 ml of ion-exchanged water. A 95 g aliquot of the prepared alumina was added to the mixture, which mixture was then evaporated to dry. The dried material was further dried in air at 120° C. for 24 hours followed by calcining in air at 450° C. for 4 hours. The calcined material was treated in hydrogen gas stream at 400° C. for 3 hours. to obtain the catalyst [5]. Analysis of thus obtained catalyst [5] gave the composition as $CuO:Al_2O_3=5:95$ (by weight).

Example 1

The catalyst [1] was pulverized in a ball mill to fine powder having an average particle size of 16.9 µm. The catalyst [2] was pulverized in a ball mill to fine powder having an average particle size of 15.6 µm. The catalyst [3] was pulverized in a ball mill to fine powder having an average particle size of 15.5 µm. A 2.4 g aliquot of the fine powder of catalyst [1], an 1.2 g aliquot of the fine powder of catalyst [2], and an 1.2 g aliquot of the fine powder of catalyst [3] were physically mixed together.

Example 2

The catalyst [1] was pulverized in a ball mill to fine powder having an average particle size of 16.9 µm. The catalyst [4] was pulverized in a ball mill to fine powder having an aver age particle size of 15.2 µm. A 2.4 g aliquot of the fine powder of catalyst [1] and an 1.2 g aliquot of the fine powder of catalyst [4] were physically mixed together.

Example 3

A 2.4 g aliquot of the fine powder of catalyst [1] having an average particle size of 14.4 µm and an 1.2 g aliquot of the fine powder of catalyst [4] having an average particle size of 12.9 µm were physically mixed together.

Example 4

A 2.4 g aliquot of the fine powder of catalyst [1] having an average particle size of 16.9 µm and an 1.2 g aliquot of the fine powder of catalyst [5] having an average particle size of 18.4 μm were physically mixed together.

Comparative Example 1

Catalysts were mixed conforming to the procedure of Example 1 except that the average particle size of the catalyst [2] was 20.1 μm and that the average particle size of the catalyst [3] was 18.5 μm.

Comparative Example 2

Catalysts were mixed conforming to the procedure of Example 2 except that the average particle size of the catalyst [4] was 12.9 μm.

II. Method for Activating Catalyst and Reaction Method

A 24 g of n-hexadecane (31.1 ml) was charged to a bubble-tower reactor having 2 cm of inside diameter and 2 m of height, and 3.6 g of each of the above-described catalyst powders was added to make the contents of the reactor in a suspended state. A mixed gas of hydrogen, carbon monoxide, and nitrogen (at a molar ratio $H_2:CO:N_2$ of 1:1:9) was introduced to pass through the bubble-tower at a flow rate of about 300 ml/min. While flowing the mixed gas through the bubble-tower, the temperature in the bubble-tower was gradually raised from room temperature to 220° C. within a period of several hours. At the same time, the concentration of nitrogen in the mixed gas was gradually reduced to a final level of zero. Then, the reaction system was held at 220° C. for about 3 hours to activate the catalyst.

The reaction was conducted at a specified temperature and pressure while introducing the mixed gas of hydrogen, carbon monoxide, and carbon dioxide at a molar ratio of $H_2/CO/CO_2=47.5/47.5/5.0$ and at a flow rate of 336 mil/min. (converted at a condition of normal temperature and pressure).

The obtained reaction products and non-reacted substances were analyzed by gas chromatography.

III. Reaction Conditions and Experimental Results

The reaction conditions and experimental results are shown in Tables 11 and 12.

$$\text{Conversion of dimethylether}(\%) = \frac{\text{Charge rate of dimethylether} - \text{Discharge rate of non-reacted dimethyleter}}{\text{Charge rate of dimethylether}} \times 100$$

$$\text{Yield of methanol}(\%) = \frac{\frac{1}{2} \times \text{Yielding rate methanol}}{\text{Charge rate of dimethylether}} \times 100$$

$$\text{Yield of hydrocarbons}(\%) = \frac{\sum \left[n/2 \times \text{yielding rate of hydrocarbons (number of carbons: } n)\right]}{\text{Charge rate of dimethylether}} \times 100$$

$$\text{Yield of } CO_2 (\%) = \frac{\frac{1}{4} \times \text{Yielding rate of } CO_2}{\text{Charge rate of dimethylether}} \times 100$$

TABLE 11

| | | Example 1 | | | Example 2 | | Example 3 | |
|---|---|---|---|---|---|---|---|---|
| Catalyst | Catalyst No. | ① | ② | ③ | ① | ④ | ① | ④ |
| | Particle Density (g/cm²) | 28.2 | 3.17 | 3.20 | 2.82 | 3.31 | 2.82 | 3.31 |
| | Particle size (cm) × 10⁴ | 16.9 | 15.6 | 15.5 | 16.9 | 15.2 | 14.4 | 12.9 |
| | Weight (g) | 2.4 | 1.2 | 1.2 | 2.4 | 1.2 | 2.4 | 1.2 |
| | Value of A (g/cm) × 10⁵ | 5.85 | 5.83 | 5.83 | 5.85 | 5.86 | 4.25 | 4.22 |
| Condition | Temperature (° C.) | 280 | | | 280 | | 280 | |
| | Pressure (kg/cm²-G) | 30 | | | 30 | | 30 | |
| Reaction Result | CO conversion (%) | 40.1 | | | 53.9 | | 52.1 | |
| | Yield Dimethyl ether | 31.2 | | | 36.2 | | 34.0 | |
| | (C-mol %) Methanol | 2.5 | | | 2.5 | | 2.6 | |
| | Hydrocarbons | 1.2 | | | 0.8 | | 0.5 | |
| | $CO_2$ | 5.5 | | | 14.4 | | 15.0 | |
| | Dimethyl ether space time yield (g/kg-cat · h) | 853 | | | 990 | | 930 | |

TABLE 12

| | | Example 1 | | Comparative example 1 | | | Comparative example 2 | |
|---|---|---|---|---|---|---|---|---|
| Catalyst | Catalyst No. | ① | ⑤ | ① | ② | ③ | ① | ④ |
| | Particle Density (g/cm²) | 2.82 | 2.50 | 2.82 | 3.17 | 3.20 | 2.82 | 3.31 |
| | Particle size (cm) × 10⁴ | 16.9 | 18.4 | 16.9 | 20.1 | 18.5 | 16.9 | 12.9 |
| | Weight (g) | 2.4 | 1.2 | 2.4 | 2.4 | 1.2 | 2.4 | 1.2 |
| | Value of A (g/cm) × 10⁵ | 5.85 | 5.85 | 5.85 | 9.68 | 8.31 | 5.85 | 4.22 |
| Condition | Temperature (° C.) | 280 | | 280 | | | 280 | |
| | Pressure (kg/cm²-G) | 30 | | 30 | | | 30 | |

TABLE 12-continued

|  |  | Example 1 | Comparative example 1 | Comparative example 2 |
|---|---|---|---|---|
| Reaction Result | CO conversion (%) | 52.7 | 33.4 | 41.6 |
|  | Yield Dimethyl ether | 35.1 | 23.3 | 26.9 |
|  | (C-mol %) Methanol | 2.1 | 1.2 | 2.0 |
|  | Hydrocarbons | 0.9 | 0.8 | 0.5 |
|  | $CO_2$ | 14.6 | 8.1 | 12.2 |
|  | Dimethyl ether space time yield (g/kg-cat · h) | 960 | 637 | 736 |

The catalyst for manufacturing dimethyl ether according to the present invention provides effects of preventing separation of individual catalyst ingredients from each other during reaction, of assuring smooth progress of reaction cycle, and of achieving high dimethyl ether yield owing to the controlled particle density and particle size for each of the methanol synthesis catalyst, the methanol-dehydration catalyst, and the water gas shift catalyst conforming to a derived equation.

The method for manufacturing dimethyl ether according to the present invention uses a slurry of solvent with a catalyst comprising a methanol synthesis catalyst, a methanol-dehydration catalyst, and a water gas shift catalyst being integrated together, so the method provides effects of achieving high space time yield of dimethyl ether, of being free from problems of plugging of catalyst and of mechanical strength of catalyst, of easiness for removing reaction heat and for controlling reaction heat, of assuring wide application range of the ratio of carbon monoxide to hydrogen, of progress of reaction under the presence of high concentration of carbon dioxide, and of less influence of impurities and catalyst poisons.

Embodiment 5

Synthesis of dimethyl ether proceeds following the three equilibrium reactions shown below.

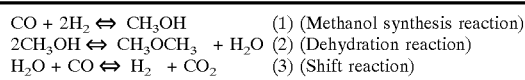

| | |
|---|---|
| $CO + 2H_2 \Leftrightarrow CH_3OH$ | (1) (Methanol synthesis reaction) |
| $2CH_3OH \Leftrightarrow CH_3OCH_3 + H_2O$ | (2) (Dehydration reaction) |
| $H_2O + CO \Leftrightarrow H_2 + CO_2$ | (3) (Shift reaction) |

In the case that the reaction (1) is solely carried out, the reaction is what is called the methanol synthesis reaction. The methanol synthesis reaction has a limitation of equilibrium, and a high pressure (80 to 120 kg/cm$^2$) is necessary to obtain a target conversion. In the single stage process, however, the reaction (2) which is significantly superior in terms of equilibrium successively proceeds within the same reactor to consume the methanol as the reaction product, so the inferior reaction equilibrium of reaction (1) is compensated. As a result, the dimethyl ether synthesis becomes very easy compared with conventional methanol synthesis process. That is, the single stage process increases the conversion of CO/H$_2$.

The reaction mixture comprises non-reacted CO and H$_2$, reaction products methanol, dimethyl ether, and CO$_2$, and slight amount of byproducts such as alkane. Since the composition depends on the reaction rate and equilibrium of each of the reactions (1) through (3), the single stage process cannot increase the amount of solely a target product. In particular, methanol as an intermediate is unavoidably left in the reaction products.

Reaction rate in each reaction is controlled by changing the ratio of methanol synthesis catalyst, dehydration catalyst, and shift catalyst. Thus the composition of the reaction products is controlled. Since, however, these three types of reactions proceed simultaneously and since all of these three reactions are equilibrium reactions, the control has a limitation owing to the limit of equilibrium. With that type of reaction system and under a normal reaction condition, it is very difficult to attain the selectivity of dimethyl ether over 95% (in the products excluding CO$_2$).

The difficulty is described below referring to a thermodynamic calculation.

Figure 2:
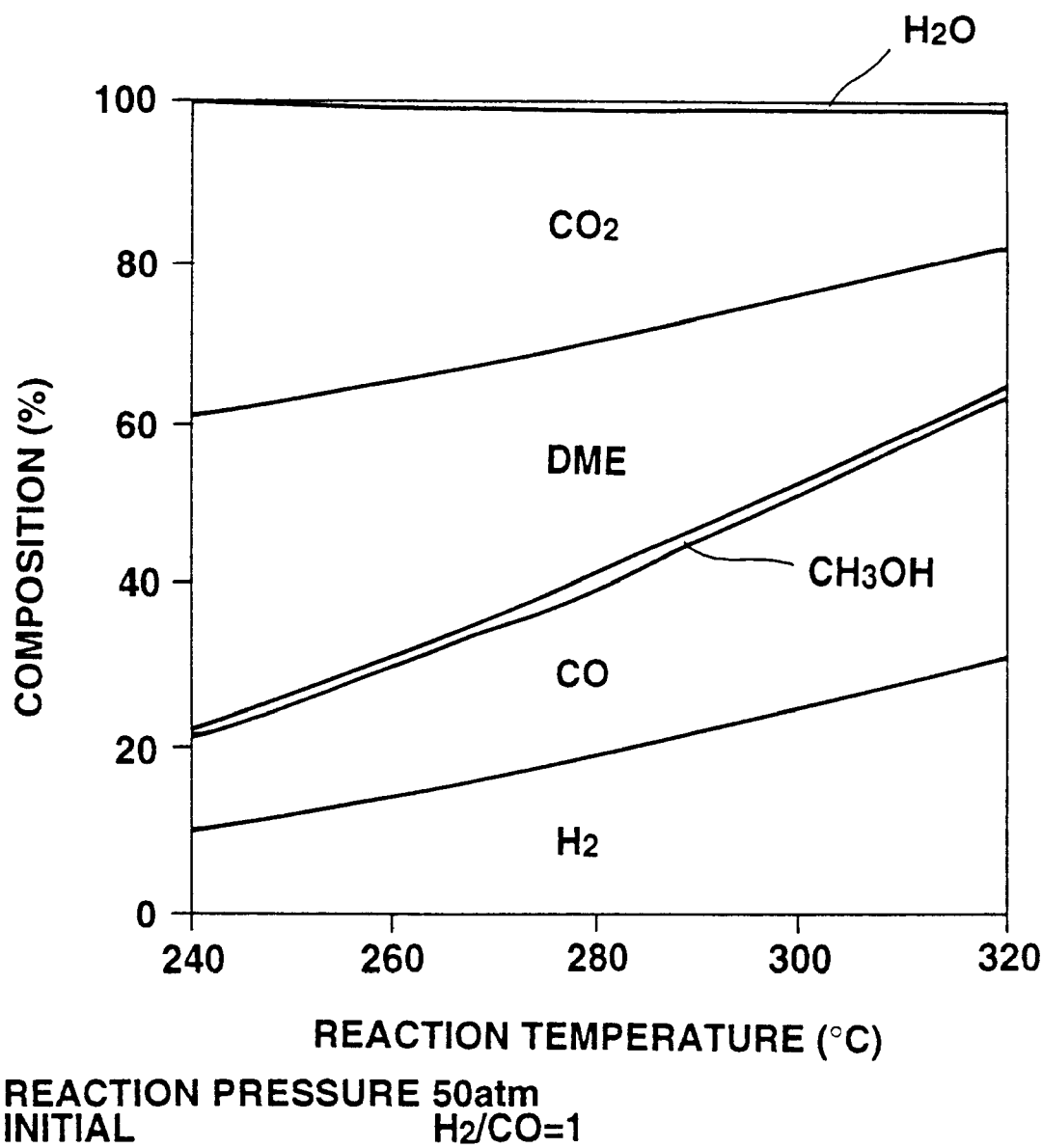
FIG. 2 is a graph showing reaction equilibria of $H_2$, CO, methanol, $CO_2$, and $H_2O$.

FIG. 2 shows reaction equilibria of H$_2$, CO, methanol, CO$_2$, and water, on the basis of reactions (1), (2), and (3). For instance, under a condition of 300° C. of reaction temperature, 50 atm of reaction pressure, and 1 of initial CO/H$_2$ ratio, the selectivity of dimethyl ether (starting material of CO, carbon molar basis, excluding CO$_2$) at the reaction equilibrium is 98%. Establishing a reaction equilibrium is, however, impossible in actual process, and the selectivity of dimethyl ether becomes significantly lower level than the calculated value owing to the presence of methanol as an intermediate. In a state of lower temperature than the above example, for instance at 240° C. of reaction temperature, 50 atm of reaction pressure, and 1 of initial CO/H$_2$ ratio, the selectivity of dimethyl ether at a reaction equilibrium becomes 99% which is somewhat higher than that in the above example. Under the condition, however, the rate of methanol-synthesis reaction (1) is low and actually the reaction equilibrium is never established.

The method according to the present invention uses a mixture of methanol synthesis catalyst, dehydration catalyst or dehydration and shift catalyst in the first stage reaction to yield crude dimethyl ether, and uses dehydration and/or shift catalyst in the second stage reaction to convert most of the remained methanol into dimethyl ether, thus attains a high selectivity of dimethyl ether.

That is, the first stage reaction increases the conversion of CO/H$_2$ raw material mixed gas by using a combined methanol synthesis catalyst+dehydration catalyst+shift catalyst. The second stage reaction uses dehydration catalyst and/or shift catalyst, and adopts a reaction condition particularly suitable for the above-described reactions, thus achieving the conversion of most part of the remaining methanol into dimethyl ether to increase the selectivity of dimethyl ether.

The second stage reaction uses only dehydration and/or shift catalyst without applying methanol synthesis catalyst. When the second stage reaction adopts a reaction condition particularly suitable for the dehydration and/or shift reaction, solely the dehydration and/or shift reaction proceeds and only these reactions approach the equilibrium state. In a reaction system where no methanol synthesis catalyst exists, no additional methanol yields, and the remained methanol is converted into dimethyl ether, so the selectivity of dimethyl ether increases.

Accordingly, the present invention provides a method for manufacturing dimethyl ether comprising the steps of: using a mixed gas as a raw material gas containing carbon monoxide and either or both of hydrogen and water vapor, or further containing carbon dioxide; conducting a first stage reaction by contacting the raw material gas with a catalyst containing a synthesis catalyst, a methanol-dehydration catalyst, and a shift catalyst; and conducting a second stage reaction by contacting the first stage product gas with a catalyst containing at least one of the dehydration catalyst and the shift catalyst.

The catalyst used in the first stage according to the present invention is a combination of known methanol synthesis catalyst, known dehydration catalyst, and known water gas shift catalyst. Applicable methanol synthesis catalyst includes common industrial catalysts for methanol synthesis, such as those of copper oxide-zinc oxide system, zinc oxide-chromium oxide system, copper oxide-zinc oxide/chromium oxide system, copper oxide-zinc oxide/alumina system. Examples of dehydration catalyst are acid-base catalyst such as γ-alumina, silica, silica-alumina, and zeolite. Examples of the metallic oxide ingredient in zeolite are oxide of alkali metal such as sodium and potassium, and oxide of alkali earth metal such as calcium and magnesium. Examples of water gas shift catalyst are copper oxide-zinc oxide system, copper oxide-chromium oxide-zinc oxide system, and iron oxide-chromium oxide system. Since methanol synthesis catalyst has a strong activity as a shift catalyst, it can substitute for the water gas shift catalyst. A copper oxide supported by alumina is applicable as a dehydration catalyst and also as a water gas shift catalyst.

The mixing ratio of the above-described methanol synthesis catalyst, dehydration catalyst, and water gas shift catalyst is not specifically limited, and it depends on the kind of each ingredient and reaction condition. Normally the ratio is often in an approximate range of from 0.1 to 5 wt.parts of dehydration catalyst to 1 wt.parts of methanol synthesis catalyst, more preferably in an approximate range of from 0.2 to 2; in an approximate range of from 0.2 to 5 wt.parts of water gas shift catalyst, more preferably in an approximate range of from 0.5 to 3. When the methanol synthesis catalyst substitutes for the water gas shift catalyst, the above-described amount of the water gas shift catalyst is added to the amount of the methanol synthesis catalyst.

The catalyst used in the second stage reaction is a combination of dehydration catalyst, dehydration-shift catalyst, and a combination of dehydration catalyst+shift catalyst. The dehydration-shift catalyst may use a catalyst of copper oxide supported by γ-alumina as the catalyst having activity of both dehydration and shifting.

Preferable catalysts used in the second stage reaction include those listed as examples of dehydration catalyst, shift catalyst, and dehydration-shift catalyst in the first stage reaction.

Above-described catalysts in both of first and second stage reactions are used in a powder state. A preferable average particle size is 300 μm or less, more preferably in an approximate range of from 1 to 200 μm, and most preferably in an approximate range of from 10 to 150 μm. To prepare powder of that range of particle size, the catalysts may further be pulverized.

The type of the catalyst reactor for the first stage and the second stage may be either a fixed bed type or a slurry bed type. When the fixed bed type reactor is applied, the catalysts are granulated to a suitable size by a known method. When the slurry bed type reactor is applied, the applicable solvent is an arbitrary kind if only the solvent maintains liquid state under the reaction condition. Examples of the solvent are hydrocarbons of aliphatic, aromatic, and alicyclic groups, alcohol, ether, ester, ketone, halide, or their mixture. Alternatively, gas oil after removing sulfur ingredients, vacuum gas oil, high boiling point distillates of coal tar after treated by hydrogenation are also applicable as the solvent. The amount of catalyst in solvent depends on the kind of solvent and the reaction condition. Normally, a preferable range of the catalyst is from 1 to 50 wt. % to the amount of solvent, more preferably in a range of from 2 to 30 wt. %.

The mixing ratio of hydrogen and carbon monoxide may be in a range of from 20 to 0.1 as $H_2/CO$ molar ratio, more preferably in a range of from 10 to 0.2. In the case of a mixed gas with significantly low ratio of ($H_2/CO$), for example, 0.1 or less, or in the case of sole carbon monoxide without containing hydrogen, it is necessary to separately supply steam to conduct the shift reaction (3) in the reactor to convert a part of the carbon monoxide into hydrogen and carbon dioxide. A preferable charge rate of steam is 1 or less to the charge rate of CO. A preferable amount of carbon dioxide yielded from the reaction is 50% or less.

A preferable condition of the first stage reaction is the reaction temperature in a range of from 150 to 400° C., particularly in a range of from 200 to 350° C. The reaction temperature below 150° C. and above 400° C. results in a reduction of carbon monoxide conversion. A preferable reaction pressure is in a range of from 10 to 300 $kg/cm^2$, particularly in a range of from 15 to 150 $kg/cm^2$. The reaction pressure below 10 $kg/cm^2$ results in a low conversion of carbon monoxide, and that above 300 $kg/cm^2$ requires special design of reactor and is uneconomical because of the need of a large amount of energy for pressurizing the system. A preferable space velocity (charge rate of mixed gas per 1 g of catalyst under standard condition) is in a range of from 100 to 50000 l/kg·h, and particularly preferable from 500 to 30000 l/kg·h. The space velocity above 50000 l/kg·h degrades the conversion of carbon monoxide, and that below 100 l/kg·h is uneconomical because of the need of an excessively large reactor.

The condition of the second stage reaction may be the same with that of the first stage reaction. A major characteristic of the method according to the present invention is to conduct the second stage reaction separately from the first one, which allows selecting an optimum condition particularly for the dehydration reaction (2) and for the shift reaction (3). That is, according to an analysis of reaction equilibrium, the reactions of (2) and (3) become advantageous at a low temperature level, and these reactions attain sufficient levels of reaction rate at a low temperature compared with the reaction of (1). Therefore, the second stage reaction favorably adopts lower temperature than the first stage reaction. Since the reaction pressure does not affect the reaction equilibrium, low pressure level is applicable.

A practical reaction condition is in a temperature range of from room temperature to 300° C., more preferably in a range of from 100 to 300° C., and preferably in a pressure range of from atmospheric pressure to the pressure of first stage reaction. Higher pressure is preferable because the reactor volume decreases. Nevertheless, it is not preferable to apply higher pressure than that of the first stage reaction because of the necessity of additional energy for pressurizing the system. Space velocity depends on the intensity of catalyst activity. A preferable space velocity is normally in a range of from 100 to 50000 l/kg·h, and particularly preferable from 500 to 30000 l/kg·h. The space velocity above 50000 l/kg·h results in failing to fully approach to the equilibrium and failing to increase the selectivity of dimethyl ether.

The ratio of the amount of catalyst in the first and second stages depends on the activity of individual catalysts. A preferable ratio of them (first stage/second stage) is normally in a range of from 1:10 to 10:1, more preferably in a range of from 1:5 to 5:1.

The CO conversion, the selectivity of dimethyl ether, and the selectivity of methanol referred to herein are defined as follows.

Amount of CO gas charged to reactor (Nl/min.):Fin(CO)
Amount of CO gas discharged from reactor:Fout(CO)
Amount of DME gas discharged from reactor:Fout(DME)
Amount of MeOH gas discharged from reactor:Fout(MeOH)
Amount of methane gas discharged from reactor:Fout($CH_4$)

$$(\text{CO conversion}) = \frac{Fin(CO) - Fout(CO)}{Fin(CO)} \times 100 \ (\%)$$

$$(\text{Selectivity of dimethylether}) = \frac{2 \times Fout(DME)}{2 \times Fout(DME) + Fout(MeOH) + Fout(CH_4)}$$

$$(\text{Selectivity of methanol}) = \frac{Fout(MeOH)}{2 \times Fout(DME) + Fout(MeOH) + Fout(CH_4)}$$

EXAMPLE

Example 1

An applied apparatus is shown in FIG. 1. The apparatus comprises a series of a first stage reactor 1 which is a slurry bed type and a second stage-reactor 2 which is a fixed bed type. To the bottom of the first stage reactor 1, a $H_2$ gas pipe and a CO gas pipe are connected, each of which is equipped with an automatic pressure control valve and with a mass flow rate controller, respectively, FRCA2 and FRCA1. The top of the first stage reactor 1 is connected to the bottom of the second stage reactor 2. The top of the second stage reactor 2 is connected to a gas-liquid separator 4 via a cooler 3. The gas exit of the gas-liquid separator 4 is connected to an exhaust line via a gas meter 5. The liquid exit of the gas-liquid separator 4 is connected to a product storage tank 6. A branch is located on the line between the exit of the reactor 2 and the cooler 3, through which the composition of exit gas is analyzed.

Catalyst A: $CuO$—$ZnO$—$Al_2O_3$ Catalyst

Each of 185 g of copper nitrate ($Cu(NO_3)_2 3H_2O$), 117 g of zinc nitrate ($Zn(NO_3)_2 6H_2O$), and 52 g of aluminum nitrate ($Al(NO_3)_3 9H_2O$) were dissolved into about 1 liter of ion-exchanged water. Separately, about 1.4 kg of sodium carbonate ($Na_2CO_3$) was dissolved into about 1 liter of ion-exchanged water. Both of the solutions were added dropwise to about 3 liters of ion-exchanged water in a stainless steel vessel which was controlled at about 60° C. within about 2 hours while maintaining the contents to pH 7.0±0.5. Then, the contents were allowed to stand for: about 1 hour for aging. When, during the treatment, the pH value went out from a range of pH 7.0±0.5, an aqueous solution of about 1 mole/liter sodium carbonate was added dropwise to keep the range of pH 7.0±0.5. The resulted precipitate was filtered, and the cake was rinsed by ion-exchanged water until nitric acid ion was not detected anymore. After the rinse, the cake was dried at 120° C. for 24 hours followed by calcining thereof in air at 350° C. for 5 hours to obtain the target catalyst. Analysis of thus obtained catalyst gave the composition as $CuO:ZnO:Al_2O_3$=61:32:7 (by weight).

Catalyst B: $CuO$—$Al_2O_3$ Catalyst

A 15.7 g of copper acetate ($Cu(CH_3COO)_2 H_2O$) was dissolved into about 200 ml of ion-exchanged water. A 95 g of γ-alumina (N612, Nikki Kagaku Co.) was further added to the mixture. The mixture was then vaporized to dry. The dried material was calcined in air at 450° C. for 4 hours. The calcined material was treated in hydrogen gas stream at 400° C. for 3 hours to obtain a catalyst. Analysis of the catalyst gave the composition as $Cu:Al_2O_3$=5:95 (by weight).

Each of the catalyst thus prepared was pulverized in a ball mill to a particle size of 120 μm or less.

The reactor (1) was filled with 5584 ml of n-hexadecane as the heating medium oil, 430 g of the catalyst A, and 215 g of catalyst B: that is, (catalyst A/catalyst B)=2/1, and (catalyst/heating medium oil)=15/100. The reactor B was filled solely with 645 g of catalyst B.

(Preliminary Reduction)

Under a condition of 10 kg/cm² of reactor pressure, 220° C. of reactor temperature, a mixed gas ($H_2/N_2$=1/4) was introduced to the reactor at a flow rate of 10 l/min. for 12 hours to conduct preliminary reduction.

Examples 1 Through 4

A mixed gas ($H_2/CO$=1/1) was introduced to the reaction system at a flow rate of 80 l/min. The condition of the reactor 1 was kept unchanged at 50 kg/cm² of reaction pressure and 260° C. of reaction temperature, while the condition of the reactor 2 was changed for conducting the dimethyl ether synthesis. A gas chromatograph was used for analyzing the gas composition, and a gas meter was used to determine the gas flow rate at exit of the reaction system. Thus, the CO conversion and the selectivity of each reaction product (carbon molar basis, in the products excluding $CO_2$) were computed. The result is shown in table 13.

TABLE 13

|  | Example 1 (Comparative Example) | Example 2 | Example 3 | Example 4 |
|---|---|---|---|---|
| Pressure in the reactor (2) (kg/cm²) | Reactor (2) was by-passed | 30 | 10 | 30 |
| Temperature in the reactor (2) (° C.) |  | 240 | 240 | 260 |
| CO conversion (%) | 34.0 | 42.4 | 42.2 | 41.4 |
| DME selectivity (%) | 67.1 | 96.1 | 94.4 | 93.6 |
| Methanol selectivity (%) | 32.8 | 3.8 | 5.5 | 6.3 |
| Methane selectivity (%) | 0.1 | 0.1 | 0.1 | 0.1 |

Examples 5 Through 8

A mixed gas ($H_2/CO$=1.5/1) was introduced to the reaction system at a flow rate of 66.7 l/min. The condition of the reactor (1) was kept unchanged at 50 kg/cm² of reaction pressure and 280° C. of reaction temperature, while the condition of the reactor (2) was changed for conducting the dimethyl ether synthesis. With the same analytical method as in Examples 1 through 4, the CO conversion and the selectivity of each reaction product were determined. The result is shown in Table 14.

TABLE 14

|  | Example 1 (Comparative Example) | Example 2 | Example 3 | Example 4 |
|---|---|---|---|---|
| Pressure in the reactor (2) (kg/cm²) | Reactor (2) was by-passed | 30 | 10 | 30 |

TABLE 14-continued

|  | Example 1 (Comparative Example) | Example 2 | Example 3 | Example 4 |
|---|---|---|---|---|
| Temperature in the reactor (2) (° C.) |  | 240 | 240 | 260 |
| CO conversion (%) | 51.5 | 66.4 | 64.4 | 64.9 |
| DME selectivity (%) | 84.4 | 94.9 | 93.8 | 93.2 |
| Methanol selectivity (%) | 15.3 | 4.8 | 5.9 | 6.5 |
| Methane selectivity (%) | 0.3 | 0.3 | 0.3 | 0.3 |

The method according to the present invention yields dimethyl ether from carbon monoxide and hydrogen (or water vapor) at a high conversion and a high selectivity. As a result, dimethyl ether is obtained from the reaction products readily at a high purity, thus manufactures dimethyl ether at a large volume at a low cost.

Embodiment 6

The inventors studied a means to maintain a high CO conversion level while decreasing the concentration of $CO_2$ in the recycle gas to increase the use efficiency of raw material gas, or a means to fully remove $CO_2$ from the non-reacted gas. A method for removing $CO_2$ may be the one to pass the non-reacted gas containing high concentration level of $CO_2$ through an alkali solution such as aqueous caustic soda to remove thereof through reaction-absorption operation. The method is, however, not a favorable one because it needs a complex process, high investment cost, and high operation cost to recover and reuse alkali. The inventors focused on the solubility and absorbability of CO2 in DME (dimethyl ether), and found that $CO_2$ is efficiently removed from the reacted gas by recycling a part of DME which was separated from $CO_2$ to the non-reacted gas separation step (S2) and by using $CO_2$ as a material being absorbed.

In concrete terms, the present invention relates to a method for manufacturing dimethyl ether which comprises: letting a raw material gas containing at least carbon monoxide and hydrogen catalytically react to yield dimethyl ether; and letting carbon monoxide and hydrogen left in reaction products recycle for reuse thereof, wherein carbon dioxide accompanied by the recycling carbon monoxide and hydrogen is removed therefrom by making the recycling gas mixture contact with a liquid dimethyl ether which was separated from the reaction products to absorb and remove the carbon dioxide from the recycling gas mixture.

An applicable mixing ratio of hydrogen to carbon monoxide in the raw material gas is in a molar ratio ($H_2$/CO) ranging from 0.1 to 20, more preferably from 0.2 to 5. Examples of the raw material gas are coal gasified gas and synthesis gas produced from natural gas.

A mixed catalyst of a methanol synthesis catalyst and a methanol-dehydration catalyst is used as the dimethyl ether-synthesis catalyst, and, at need, further a water gas shift catalyst is added to the mixed catalyst system. Alternatively, the water gas shift catalyst may be separately used to configure a two-stage reaction system. The present invention is applicable to any of these catalysts.

An applicable methanol synthesis catalyst includes common industrial catalysts for methanol synthesis, such as those of copper oxide-zinc oxide system, zinc oxide-chromium oxide system, copper oxide-zinc oxide/chromium oxide system, copper oxide-zinc oxide/alumina system. Examples of methanol-dehydration catalyst are acid-base catalyst such as γ-alumina, silica, silica-alumina, and zeolite. Examples of the metallic oxide ingredient in zeolite are oxide of alkali metal such as sodium and potassium, and oxide of alkali earth metal such as calcium and magnesium. Examples of water gas shift catalyst are copper oxide-zinc oxide system, copper oxide-chromium oxide-zinc oxide system, and iron oxide-chromium oxide system. Since a methanol synthesis catalyst has a strong activity as a shift catalyst, it can substitute for the water gas shift catalyst. A copper oxide supported by alumina is applicable as a methanol-dehydration catalyst and also as a water gas shift catalyst.

The mixing ratio of the above-described methanol synthesis catalyst, methanol-dehydration catalyst, and water gas shift catalyst is not specifically limited, and it depends on the kind of each ingredient and reaction condition. Normally the ratio is often in an approximate range of from 0.1 to 5 wt.parts of methanol-dehydration catalyst to 1 wt.parts of methanol synthesis catalyst, more preferably in an approximate range of from 0.2 to 2; in an approximate range of from 0.2 to 5 wt.parts of water gas shift catalyst, more preferably in an approximate range of from 0.5 to 3. When the methanol synthesis catalyst substitutes for the water gas shift catalyst, the above-described amount of the water gas shift catalyst is added to the amount of the methanol synthesis catalyst.

The above-described catalysts are applicable to any type of reaction in fixed bed, fluidized bed, and slurry-bed type reactors. In particular, the slurry-bed reaction provides uniform temperature within the reactor and yields less by-products. The following description deals with the slurry-bed reaction as a typical mode.

For the case of a slurry-bed reaction, the catalyst is used in a fine powder shape. A preferable average particle size is 300 μm or less, more preferably in an approximate range of from 1 to 200 μm, and most preferably in an approximate range of from 10 to 150 μm. To prepare powder of that range of particle size, the catalysts may further be pulverized.

An applicable kind of medium oil is an arbitrary one if only the medium oil maintains liquid state under the reaction condition. For example, the medium oil may be hydrocarbons of aliphatic, aromatic, and alicyclic groups, alcohol, ether, ester, ketone, halide, or their mixture. Alternatively, gas oil after removing sulfur ingredients, vacuum gas oil, high boiling point distillates of coal tar after treated by hydrogenation, Fischer-Tropsch synthesis oil, and high boiling point food oil are also applicable as the medium oil. The amount of catalyst in solvent depends on the kind of solvent and the reaction condition. Normally, a preferable range of the catalyst is from 1 to 50 wt. % to the amount of solvent, more preferably in a range of from 2 to 30 wt. %.

For the reaction condition in a slurry-bed reactor, a preferable reaction temperature in the reactor is in a range of from 150 to 400° C., and particularly preferable in a range of from 250 to 350° C. The reaction temperature below 150° C. and above 400° C. degrades the conversion of carbon monoxide. A preferable reaction pressure is in a range of from 10 to 300 $kg/cm^2$, more preferably in a range of from 15 to 150 $kg/cm^2$, and most preferably in a range of from 20 to 70 $kg/cm^2$. The reaction pressure below 10 $kg/cm^2$ results in a low conversion of carbon monoxide, and that above 300 $kg/cm^2$ requires a special design of reactor and is uneconomical because of the need of a large amount of energy for pressurizing the system. A preferable space velocity (charge rate of mixed gas per 1 kg of catalyst under standard condition) is in a range of from 100 to 50000 l/kg·h, and particularly preferable from 500 to 30000 l/kg·h. The space velocity above 50000 l/kg·h degrades the conversion of carbon monoxide, and that below 100 l/kg·h is uneconomical because of the need of an excessively large reactor.

Thus obtained reacted gas contains carbon dioxide, carbon monoxide, hydrogen, water, and methanol, adding to dimethyl ether, and further contains by-products such as methane, and impurities carried-in by the raw material gas. An approximate composition of the reacted gas is: 1 to 40% of dimethyl ether, normally 3 to 25%; 1 to 40% of carbon dioxide, normally 3 to 25%; 10 to 70% of carbon monoxide, normally 20 to 50%; 10 to 70% of hydrogen, normally 20 to 50%; 0.2 to 5% of methanol, normally 0.5 to 3%; 0.05 to 0.8% of water, normally 0.1 to 0.5%; and 0 to 5% of other ingredients.

Arbitrary means is applicable to separate dimethyl ether from the reacted gas, and a method to use difference in condensation temperature or to use difference in boiling point is a preferable one. For the case that the difference in condensation temperature is used, firstly methanol and water condense during the passage of cooling of reacted gas. The condensate may be utilized for other uses or may be further separated into water and methanol, and the methanol may be recycled to the reactor. Further cooling of the reacted gas induces the condensation of dimethyl ether to which carbon dioxide dissolves thereinto, while leaving carbon monoxide and hydrogen, which are the non-reacted gas ingredients, in the gas phase. Separation of carbon dioxide from dimethyl ether may be conducted by distillation.

According to the method of the present invention, the above-described carbon monoxide and hydrogen as the non-reacted gas are brought into contact with the liquid dimethyl ether which was treated in the $CO_2$ separator to remove the dissolved carbon dioxide. Thus the carbon dioxide existing in the non-reacted gas is removed by dissolving into the dimethyl ether. Any type of the non-reacted gas separator may be used if only the separator cools the reacted gas and dimethyl ether and maintains the contact thereof by each other in a satisfactory degree. Examples of the separator are a shell-tube heat exchanger with a liquid holder, and a tank holding liquefied dimethyl ether with an injector of reacted gas thereinto. By the contact of reacted gas with dimethyl ether, $CO_2$ is dissolved into and absorbed by the liquefied dimethyl ether. The liquefaction of dimethyl ether occurs at $-25°$ C. under atmospheric pressure. The liquefaction becomes easy and the $CO_2$ solubility increases with increased pressure (partial pressure of dimethyl ether) and decreased temperature. When the separation temperature is low, the $CO_2$ separation efficiency increases, but the necessary scale of refrigerator also increases to increase the investment cost. Accordingly, a preferable temperature of the non-reacted gas separator is in a range of from 0 to $-70°$ C., more preferably from $-20$ to $-50°$ C. The pressure in separation stage may normally be the same with that of the reaction process.

The amount of recycling dimethyl ether is in a range of from 1 to 10 fold of the amount of $CO_2$ in the reacted gas which is brought to contact with the liquid dimethyl ether, and more preferably in a range of from 2 to 5 fold.

Based on the following definitions, the formulae 1 through 3 are derived.

Flow rate of CO gas fed to reactor (Nl/min.):Fin(CO)
Flow rate of CO gas discharged from reactor:Fout(CO)
Flow rate of DME gas discharged from reactor:Fout(DME)
Flow rate of MEOH gas discharged from reactor:Fout(MeOH)
Flow rate of methane gas discharged from reactor:Fout($CH_4$)

$$(COconversion) = \frac{Fin(CO) - Fout(CO)}{Fin(CO)} \times 100 \; (\%)$$

$$(\text{Selectivity of dimethylether}) = \frac{2 \times Fout(DME)}{2 \times Fout(DME) + Fout(MeOH) + Fout(CH_4)}$$

$$(\text{Selectivity of methanol}) = \frac{Fout(MeOH)}{2 \times Fout(DME) + Fout(MeOH) + Fout(CH_4)}$$

Figure 3:
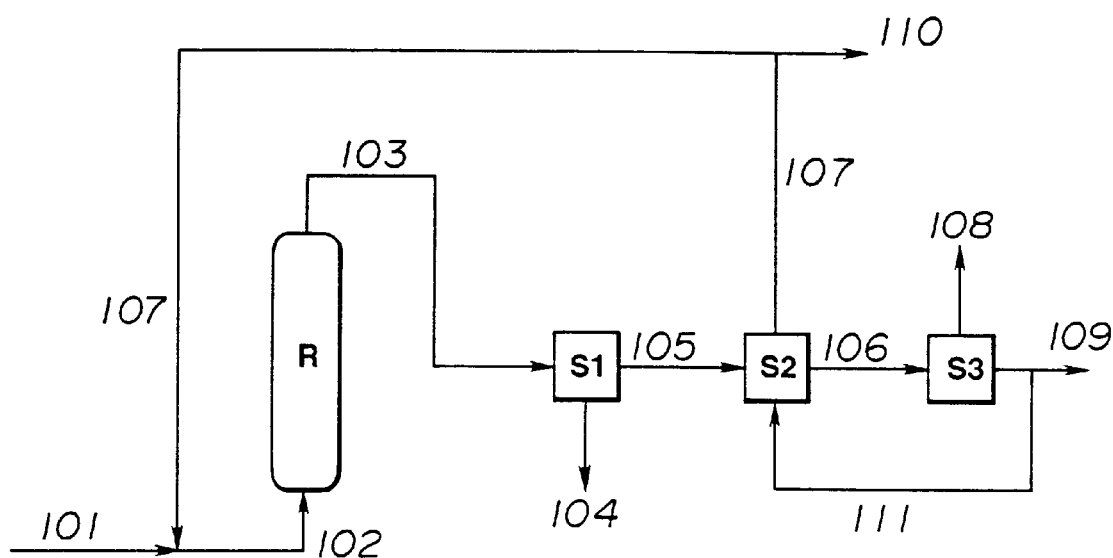
FIG. 3 is a schematic representation showing the apparatus for producing dimethyl ether used in the embodiment 6.

FIG. 3 shows an example of apparatus applied to the method according to the present invention. The apparatus includes a DME recycle line 111 which branches from the DME line 109 coming from the $CO_2$ separator S3 and which returns to the non-reacted gas separator S2. Lines (pipes or conduits) 102, 103, 108 and 110 are also depicted in FIG. 3.

Figure 4:
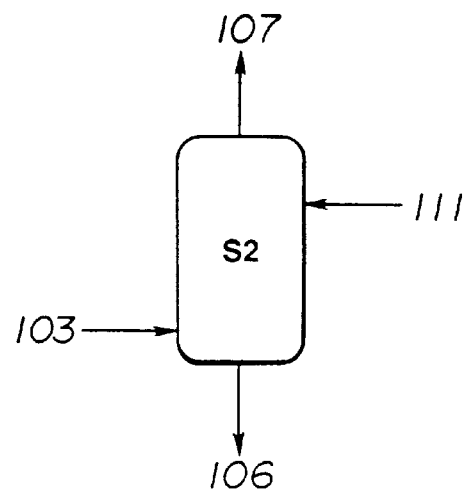
FIG. 4 is an enlarged view of the non-reacted gas separator in FIG. 3 indicating the connection of pipelines.

FIG. 4 shows an enlarged view of the non-reacted gas separator S2 used in the apparatus of FIG. 3. The non-reacted gas separator S2 comprises a vessel with a cooling jacket, and a set of pipelines, namely, a reacted gas line 105 at lower portion thereof, a DME, $CO_2$ line 106 at bottom thereof, a DME recycle line 111 at upper portion thereof, and a recycle gas line 107 at top thereof.

EXAMPLE

Example 1

A reaction experiment was conducted using an apparatus shown in FIG. 3 adopting a bubble-tower reactor R (90 mm of inner diameter, 2000 mm of height) under a reaction condition of 280° C. and 30 kg/cm². The content of the reactor was a slurry of 860 g of catalyst powder with 5730 g of n-hexadecane. The unit S1 separated methanol and water from the reactor exit gas, and discharge the separated methanol and water and discharged thereof through a methanol-water line 104. The unit S2 separated a part of the DME and $CO_2$ gas and discharge thereof through a DME, $CO_2$ line. Thus the non-reacted gas was refined. The refined non-reacted gas was recycled to the inlet of reactor via a recycle gas line 107. The consumed CO gas and hydrogen gas were supplied, and the flow rate through a CO gas and hydrogen gas make up gas line 101 was adjusted to maintain the flow rate of CO gas and hydrogen gas at the inlet of reactor to 30 Nl/min. The recycle gas contains $CO_2$ gas left un-separated in the S2 unit, and the purge rate of the recycle gas was adjusted to maintain the $CO_2$ gas flow rate at inlet of the reactor to 9 Nl/min. By assuring the gas composition at the inlet of reactor to the above-described level, the CO conversion was kept to 42%. The S2 unit was controlled to a state of $-30°$ C. and 30 kg/cm², and the DME from which $CO_2$ was removed in the S3 unit was recycled at a flow rate of 0.5 mole/min. through a line 111. The purge rate of the recycle gas in the above case was 3.8%, and the loss of CO gas and hydrogen gas relative to the make up rate was 5.0% and 3.4%, respectively.

Comparative Example 1

An experiment was conducted under the same condition with Example 1 except that the DME from which $CO_2$ was removed in the S3 unit was not recycled. The purge rate of the recycle gas in that case was 29.7%, and the loss of CO gas and hydrogen gas relative to the make up rate was 29.1% and 21.5%, respectively.

Example 2

Using a vessel with a cooling jacket, which is shown in FIG. 4, a test gas ($CO_2$:DME:CO:$H_2$=10:10:40:40) was introduced to the reactor at a flow rate of 50 mmole/min. through a line 103, and DME was introduced to the reactor at a flow rate of 5 mmole/min. through a line 111. At the same time, a discharged gas was collected through a line 107, and DME was withdrawn from the reactor through a line 106 to maintain the amount of liquefied DME in the vessel at a fixed level. The internal pressure of the vessel was 50 kg/cm$^2$G, and the internal temperature of the vessel was −30° C. The collected gas flow rate was determined by a gas meter, and the composition thereof was analyzed by a gas-chromatograph (detector: TCD). The $CO_2$ in the discharged gas was 1.9 mmole/min. and the $CO_2$ separation efficiency was 38%.

Example 3

An experiment was conducted under the same condition with Example 2 except that the DME introduction flow rate through the line 111 was set to 10 mmole/min. The $CO_2$ in the discharged gas was 2.6 mmole/min. and the $CO_2$ separation efficiency was 52%.

Example 4

An experiment was conducted under the same condition with Example 2 except that the DME introduction flow rate through the line 111 was set to 20 mmole/min. The $CO_2$ in the discharged gas was 4.1 mmole/min. and the CO, separation efficiency was 82%.

Comparative Example 2

An experiment was conducted under the same condition with Example 2 except that the DME introduction through the line 111 was not applied. The $CO_2$ in the discharged gas was 1.0 mmole/min. and the $CO_2$ separation efficiency was 20%.

Example 5

An experiment was conducted under the same condition with Example 3 except that the internal temperature of the vessel was set to −40° C. The $CO_2$ in the discharged gas was 3.1 mmole/min. and the $CO_2$ separation efficiency was 62%.

Example 6

An experiment was conducted under the same condition with Example 3 except that the internal temperature of the vessel was set to −25° C. The $CO_2$ in the discharged gas was 2.4 mmole/min. and the $CO_2$ separation efficiency was 48%.

The method according to the present invention suppresses the $CO_2$ concentration in the recycle gas to a low level, and maintains the CO conversion in DME synthesis reaction to a high level. Since the method allows to minimize the purge of the recycle gas or does not need to purge thereof, both CO and $H_2$ are effectively utilized. In addition, the method allows to use the product DME as a $CO_2$ absorbent which is readily separated from the reacted products, and the process becomes a simple one.

Embodiment 7

The present invention relates to an apparatus for manufacturing dimethyl ether comprising: a slurry-bed reactor filled with a dimethyl ether-synthesis catalyst and a medium oil therefor; a condenser for condensing a gasified medium oil discharged from the reactor; a desulfurization tank for adsorbing to remove a catalyst-deactivation ingredient from the medium oil condensed in the condenser; and a recycle line for recycling the medium oil by connecting the reactor, the condenser, and the desulfurization tank. And relates to a method for manufacturing dimethyl ether comprising the steps of: letting a raw material gas containing at least carbon monoxide and hydrogen contact a slurry of a suspended dimethyl ether-synthesis catalyst in a medium oil; cooling a reaction product gas generated from a catalytic reaction to condense to separate a gasified medium oil carried along with the reaction product gas; obtaining dimethyl ether from the reaction product gas; removing a catalyst-deactivation ingredient from a condensed medium oil to recycle the medium oil free of catalyst-deactivation ingredient to the slurry.

The reactor according to the present invention may be an arbitrary type if only it is a slurry-bed type.

A dimethyl ether-synthesis catalyst according to the present invention is a mixture of a methanol synthesis catalyst and a methanol-dehydration catalyst, and, if needed, a water gas shift catalyst is further added to the catalyst system. These catalyst ingredients may be used in a mixed state, or the water gas shift catalyst may be separated from other two catalyst ingredients to configure a two stage reaction system. The present invention is applicable for any types of the above-described catalyst systems.

Examples of a methanol synthesis catalyst are copper oxide-zinc oxide system, zinc oxide-chromium oxide system, copper oxide-zinc oxide/chromium oxide system, copper oxide-zinc oxide/alumina system which catalyst systems are commonly used in industrial methanol synthesis. Examples of a methanol-dehydration catalyst are acid-base catalyst such as γ-alumina, silica, silica-alumina, and zeolite. Examples of the metallic oxide ingredient in zeolite are oxide of alkali metal such as sodium and potassium, and oxide of alkali earth metal such as calcium and magnesium. Examples of a water gas shift catalyst are copper oxide-zinc oxide system, copper oxide-chromium oxide-zinc oxide system, and iron oxide-chromium oxide system. Since a methanol synthesis catalyst has a strong activity as a shift catalyst, it can substitute for the water gas shift catalyst. A copper oxide supported by alumina is applicable as dehydration catalyst and also as water gas shift catalyst.

The mixing ratio of above-described methanol synthesis catalyst, methanol-dehydration catalyst, and water gas shift catalyst is not specifically limited, and it depends on the kind of each ingredient and reaction condition. Normally the ratio is often in an approximate range of from 0.1 to 5 wt.parts of methanol-dehydration catalyst to 1 wt.parts of methanol synthesis catalyst, more preferably in an approximate range of from 0.2 to 2; in an approximate range of from 0.2 to 5 wt.parts of water gas shift catalyst, more preferably in an approximate range of from 0.5 to 3. When the methanol synthesis catalyst substitutes for the water gas shift catalyst, the above-described amount of the water gas shift catalyst is added to the amount of the methanol synthesis catalyst.

The above-described catalysts are used in a powder state. A preferable average particle size is 300 μm or less, more preferably in an approximate range of from 1 to 200 μm, and most preferably in an approximate range of from 10 to 150 μm. To prepare powder of that range of particle size, the catalysts may further be pulverized.

An applicable kind of medium oil is arbitrary if only the medium oil maintains liquid state under the reaction condition. Examples of the medium oil are hydrocarbons of aliphatic, aromatic, and alicyclic groups, alcohol, ether, ester, ketone, halide, or their mixture. Alternatively, gas oil after removing sulfur ingredients, vacuum gas oil, high boiling point distillates of coal tar after treated by hydrogenation, Fischer-Tropsch synthesis oil, and high boiling point food oil are also applicable as the medium oil. The amount of catalyst in the solvent depends on the kind of solvent and the reaction conditions. Normally, a preferable range of the catalyst is from 1 to 50 wt. % to the amount of solvent, more preferably in a range of from 2 to 30 wt. %.

The condenser according to the present invention is arbitrary if only it condenses vaporized medium oil. A heat exchanger or other types may be applied.

Removal of catalyst deactivation ingredients is preferably carried out using an adsorbent. An applicable type of the adsorbent may be the commonly used one such as γ-alumina, activated carbon, and zeolite adsorber. A necessary amount of the adsorbent depends on the adsorption capacity of the applied adsorbent The number of adsorbers is preferably more than one to ensure continuous adsorption operation during regeneration cycle of an adsorber.

The recycle line establishes a recycle passage through the slurry-bed reactor, the condenser, and the adsorber. A means to prevent backflow is located in the line. The backflow-preventive means may be a simple check valve or may be a forced circulation system using a pump.

The apparatus according to the present invention is further provided with a storage tank, an intermediate tank, valves, and instruments, as needed.

The molar mixing ratio of hydrogen and carbon monoxide, ($H_2$/CO), may be in a range of from 0.5 to 3.0, more preferably from 0.8 to 2.0. In the case of a mixed gas with significantly low ratio of ($H_2$/CO), for example, 0.5 or less, or in the case of sole carbon monoxide without containing hydrogen, it is necessary to separately supply steam to convert a part of the carbon monoxide into hydrogen and carbon dioxide within the reactor. The amount of steam supply is equal to the amount of carbon monoxide to be converted (equal to the insufficient amount of hydrogen). The amount of carbon dioxide becomes the same molar amount of the converted carbon monoxide. Examples of that type of raw material gas are coal gasified gas, synthesis gas derived from natural gas, and methane in coal stratum. When sulfur compounds exist in the raw material gas, a preliminary desulfurization is needed to prevent catalyst deactivation. The desulfurization treatment reduces the concentration of sulfur compounds to several hundreds of ppm or less, normally in an approximate range of from 50 to 200 ppm. Sulfur compounds include SOx, $H_2S$, and COS.

A preferable reaction temperature in the slurry-bed reactor is in a range of from 150 to 400° C., and particularly preferable in a range of from 250 to 350° C. The reaction temperature below 150° C. and above 400° C. degrades the conversion of carbon monoxide. A preferable reaction pressure is in a range of from 10 to 300 kg/cm$^2$, more preferably in a range of from 15 to 150 kg/cm$^2$, and most preferably in a range of from 20 to 70 kg/cm$^2$. The reaction pressure below 10 kg/cm$^2$ results in a low conversion of carbon monoxide, and that above 300 kg/cm$^2$ requires a special design of reactor and is uneconomical because of the need to a large amount of energy for pressurizing the system. A preferable space velocity (charge rate of mated gas per 1 kg of catalyst under standard condition) is in a range of from 100 to 50000 l/kg·h, and particularly preferable from 500 to 30000 l/kg·h. The space velocity above 50000 l/kg·h degrades the conversion of carbon monoxide, and that below 100 l/kg·h is uneconomical because of the need of an excessively large reactor.

A condition for eliminating the catalyst deactivation ingredients is to reduce the concentration of catalyst deactivation ingredients remaining in a medium oil after removal thereof by adsorption to 100 ppm or less, and more preferably to 50 ppm or less.

EXAMPLE

Example 1

Figure 5:
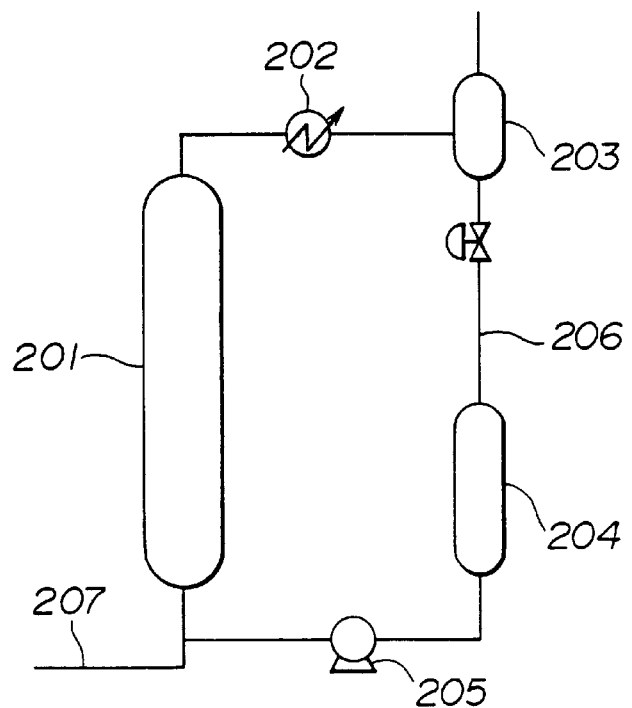
FIG. 5 is a schematic representation showing the apparatus for producing dimethyl ether used in the embodiment 7.

FIG. 5 shows an apparatus for manufacturing dimethyl ether as an example according to the present invention. The apparatus comprises a slurry reactor 201, a condenser 202, a gas-liquid separator 203, an adsorber 204, and a pump 205. These units are connected each other by pipes to form a recirculation line 206. A raw material gas is charged to the bottom of the slurry reactor 201 via a raw material gas feed pipe 207. A medium oil which is vaporized from the slurry reactor 201 or which is discharged from the slurry reactor 201 along with a high temperature reacted gas is cooled to a temperature of condensing point or below by exchanging heat thereof in the condenser 202. The cooled and partially condensed medium oil enters the gas-liquid separator 203 to separate thereof to reacted products and non-reacted gas. Thus separated and collected medium oil is sent to the adsorber 204, where the catalyst deactivation ingredients are adsorbed to remove thereof from the medium oil. The clean medium oil is then recycled to the reactor 201 by the pump 205 to maintain the concentration of catalyst deactivation ingredients in the medium oil at a low level. The desulfurization in the adsorption-desulfurization tank 204 may be carried out under the same high pressure condition with that in the reactor or may be conducted at atmospheric pressure after depressurizing. The number of adsorbers 204 may be two or more for alternative use.

An gas-flow type autoclave was used as the slurry-bed reactor. The reaction experiment was carried out under the conditions of 30 kg/cm$^2$G of pressure, 280° C. of temperature. The charged raw material gas contained carbon monoxide and hydrogen at a ratio of 1:1. The ratio of the weight of catalyst to the molar flow rate of carbon monoxide was W/F=4.0 g-cat.·h/CO-mole. The used medium oil contained different levels of dissolved sulfur ingredient concentration for each run. The applied catalyst was a mixture of methanol synthesis catalyst of copper-zinc-alumina system and methanol-dehydration catalyst of copper-alumina system at a weight ratio of 2 to 1, both in powder form.

A medium oil was n-cetane which contained no sulfur ingredient. A medium oil was industrial gas oil 1 which was refined to a level of 250 ppm of sulfur ingredients. A medium oil was industrial gas oil 2 which was refined to a level of 100 ppm of sulfur ingredients. A medium oil was industrial gas oil 3 which was refined to a level of 50 ppm of sulfur ingredients.

The resulted conversion of carbon monoxide was: 50.5% in n-cetane medium oil, 8.1% in industrial gas oil 1 containing 250 ppm of sulfur ingredients, 35.2% in industrial gas oil 2 containing 100 ppm of sulfur ingredients, and 45.6% in industrial gas oil 3 containing 50 ppm of sulfur ingredients. Therefore, according to the present invention, the concentration of sulfur ingredients in a medium oil after the sulfur ingredients were removed by adsorption is necessary to 100 ppm or less, and preferably to 50 ppm or less.

The above-described experimental result is shown in Table 15. The reaction ratio is expressed by the conversion of carbon monoxide, a raw material, on molar basis.

TABLE 15

| Medium oil | Concentration of dissolved sulfur ingredients (ppm) | Carbon monoxide conversion (C-mol %) |
| --- | --- | --- |
| Industrial gas oil 1 | 250 | 8.1 |
| Industrial gas oil 2 | 100 | 35.2 |
| Industrial gas oil 3 | 50 | 45.6 |

For the case that a n-cetane having 286.8° C. of boiling point and 226 of molecular weight was used as the medium oil, and that the internal condition of the reactor was set to 30 kg/cm²G, 280° C., W/F (ratio of catalyst weight to raw material gas carbon monoxide)=6 kg-cat/CO-kg·mol, and 20 wt. % of slurry concentration, the calculated amount of medium oil discharged from the reactor determined from a vapor-liquid equilibrium relation under the internal condition of reactor results in about 50%/h in terms of weight ratio to the initially existing amount of the medium oil in the reactor.

The actual discharge amount of the medium oil is, however, less than the calculated value owing to the temperature decrease at upper part of the reactor and to other variables. Nevertheless, under a normal condition, sufficient amount of medium oil for rectifying thereof recirculates to the adsorber 204 in FIG. 5.

Example 2

Same procedure as in Example 1 was conducted using the medium oils listed in Table 16. The result is shown in Table 16.

TABLE 16

| Medium oil | Concentration of dissolved metallic carbonyl (ppm) | Conversion of carbon monoxide (C-mol %) |
| --- | --- | --- |
| Industrial gas oil 4 | 230 (iron carbonyl) | 9.2 |
| Industrial gas oil 5 | 51 (iron carbonyl) | 32.7 |
| Industrial gas oil 6 | 3 (iron carbonyl) | 44.8 |
| Industrial gas oil 7 | 190 (nickel carbonyl) | 7.6 |
| Industrial gas oil 8 | 45 (nickel carbonyl) | 31.1 |
| Industrial gas oil 9 | 2 (nickel carbonyl) | 43.6 |

Example 3

A continuous flow high pressure reaction gas was used to suppress continuously the concentration of sulfur ingredients in the medium oil. The effectiveness of the apparatus and method according to the present invention was confirmed.

Figure 6:
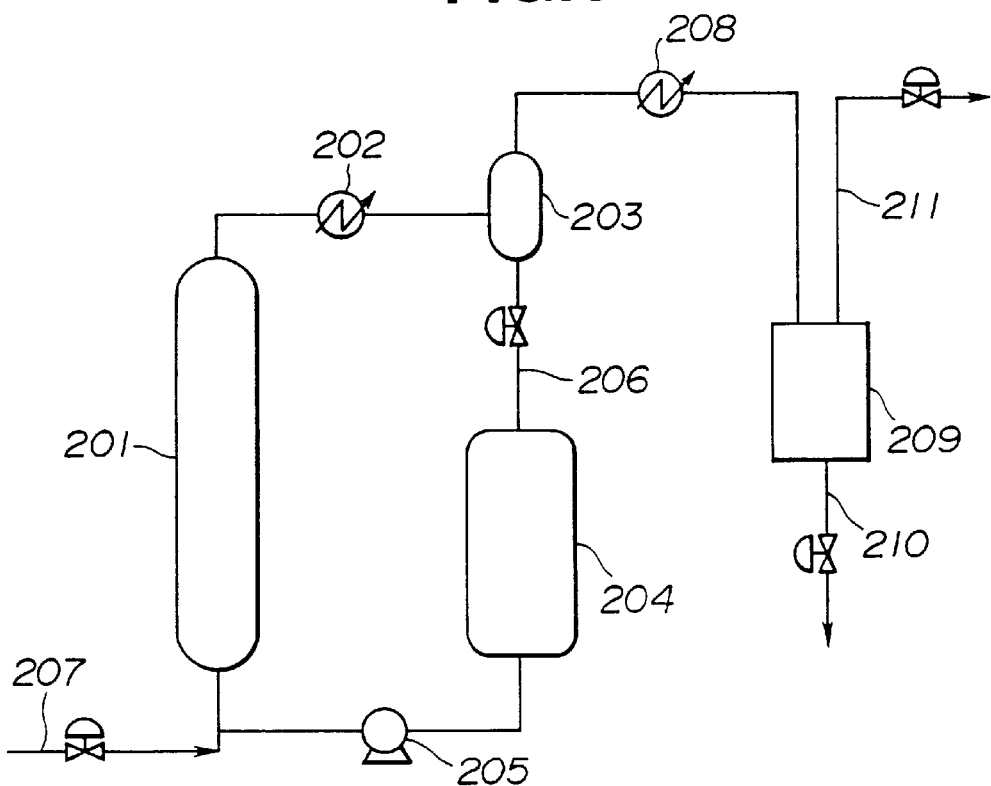
FIG. 6 is another schematic representation showing the apparatus for producing dimethyl ether used in the embodiment 7.

The applied apparatus is shown in FIG. 6. Adding to the configuration of the apparatus in FIG. 5, a second condenser 208 and a second gas-liquid separator 209 are located to the gas exhaust line of the gas-liquid separator 203.

The reacted and refined gas which was separated from medium oil in the gas-liquid separator 203 is cooled in the second condenser 208, and is then separated into liquid phase containing dimethyl ether, methanol, and water, and gas phase containing non-reacted gas and carbon dioxide in the second gas-liquid separator 209. The liquid phase is recovered through a line 210, and the gas phase is recovered through a line 211.

The reaction condition was the same with that in Example 1. The raw material charged to the reactor was a mixture of carbon monoxide and hydrogen at 1:1 ratio containing 600 ppm of hydrogen sulfide as the impurity. The applied medium oil was n-cetane containing no sulfur ingredient. The adsorbent used was granular γ-alumina A sufficient volume of adsorbent to adsorb and desulfurize the hydrogen sulfide dissolved in the medium oil was charged into the adsorber 204.

Figure 7:
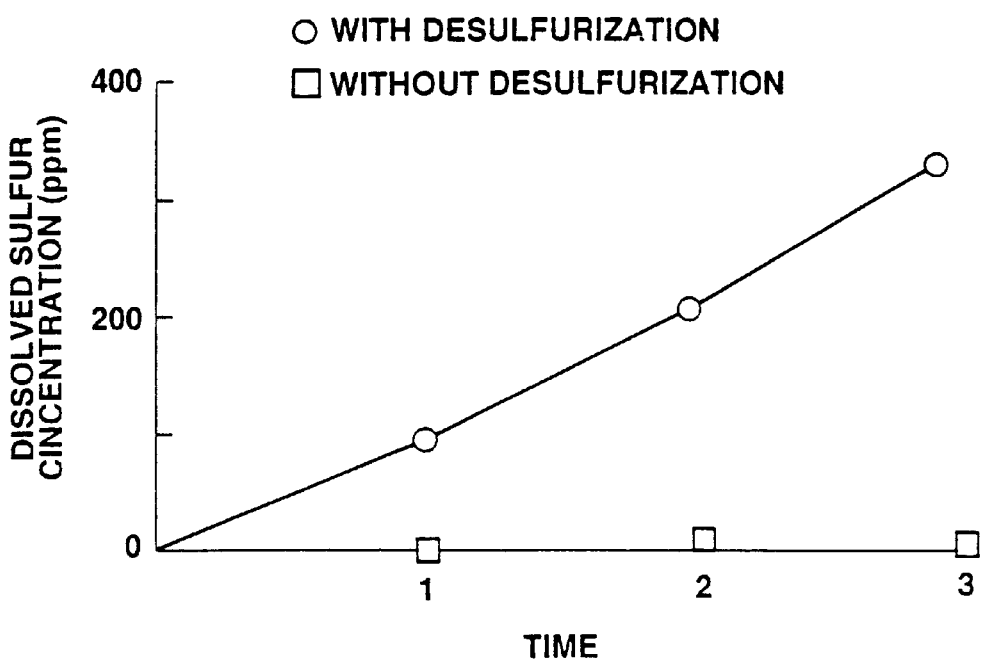
FIG. 7 is a graph showing the change of dissolved sulfur concentration with time in the case that the apparatus of FIG. 6 was used.
Figure 8:
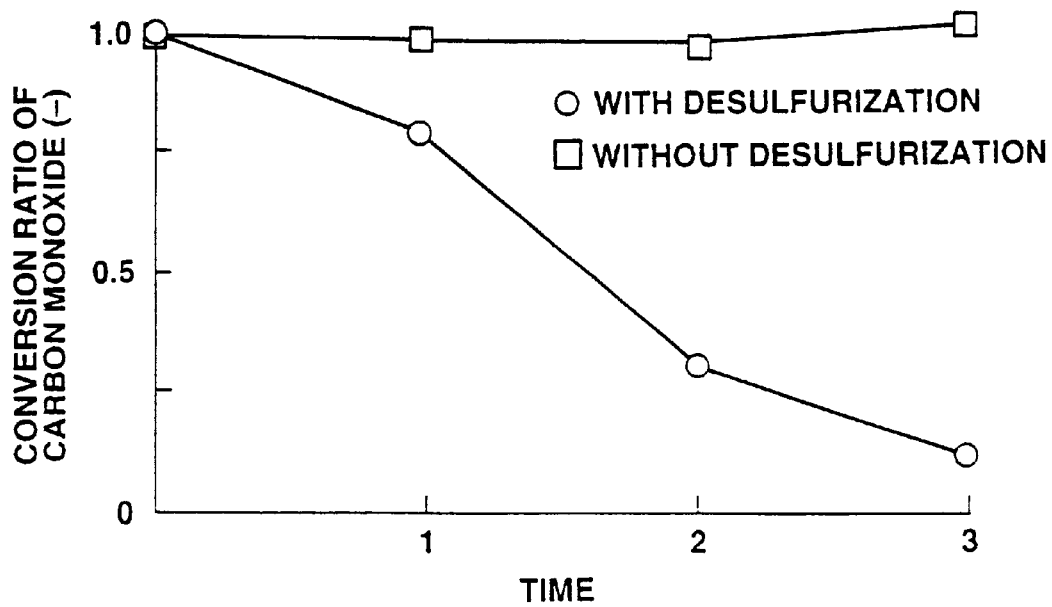
FIG. 8 is a graph showing the change in conversion of carbon monoxide with time in the case that the apparatus of FIG. 6 was used.

The result of the reaction is shown in FIGS. 7 and 8.

FIG. 7 shows the change in concentration of sulfur ingredients in the medium oil for the case of empty adsorber 204 and of adsorber 204 containing adsorbent. For the case of application of desulfurization treatment, the sulfur concentration in the recycling medium oil is kept to near zero level. For the case of non-application of desulfurization treatment, however, the sulfur concentration in the medium oil increases with the operating time.

FIG. 8 shows the change in conversion of carbon monoxide as a raw material responding to the change in sulfur ingredients with time shown in FIG. 7. For the case of application of desulfurization treatment, the conversion of carbon monoxide as a raw material keeps nearly the initial level. For the case of non-application of desulfurization treatment, however, the conversion of carbon monoxide as a raw material shows an abrupt decrease with time. The phenomena prove the effectiveness of the present invention.

According to the apparatus and method of present invention, a raw material mixed gas consisting mainly of carbon monoxide in a coal gasified gas, a synthesis gas produced from natural gas, or the like, and hydrogen is charged to a slurry of reaction catalyst with medium oil in a reactor to synthesize dimethyl ether, wherein the slight amount of catalyst deactivation ingredients existing in the raw material gas is continuously removed to maintain the concentration of catalyst deactivation ingredients in the medium oil to a low level, thus keeping a high catalyst activity for a long period.

Embodiment 8

The present invention relates to a slurry-bed reactor which comprises: a catalyst reaction layer in a state of slurry of a suspending powder catalyst with a high boiling point medium oil, charging a reaction raw material gas thereto at a bottom portion of the reactor; a condenser to condense the medium oil vaporized from the catalyst slurry layer inside of the reactor, wherein the condenser and the catalyst slurry layer are separated from each other by a separation member having a liquid seal mechanism to form a condensation chamber.

The reactor according to the present invention is a slurry-bed reactor, and the section for holding catalyst slurry as the slurry-bed is equipped with a cooling mechanism for removing reaction heat.

At an upper space of the reactor, a condenser is installed to condense the high boiling point medium oil vaporized from the catalyst slurry bed. The condenser may be an arbitrary type, and a preferable one is a multi-tube type. When the upper space in the reactor is insufficient for installing the condenser, the upper portion of the reactor may be extended in length or extending in diameter to secure the space for the installation area thereof.

The condenser and the catalyst slurry bed are separated from each other by a separation member having a liquid seal mechanism to create a condensation chamber that is separated from the catalyst slurry bed. The liquid seal mechanism means a mechanism that allows passing a gas freely therethrough in an empty state and that prohibits gas passing freely therethrough when the mechanism is filled with liquid while the gas is allowed to pass the filled liquid by a pressure difference or by dissolving into and vaporizing from the filled liquid. An example of a preferred liquid seal member is a bubble-cap plate which is used in a distillation column.

There is a need to prepare a return line for smoothly returning the medium oil condensed in the condensation chamber to the catalyst slurry layer. The return line is required to maintain the independence of the condensation chamber from the catalyst slurry layer. Accordingly, the line has a sealed structure separate from the space between the catalyst slurry layer and the condensation chamber. In addition, for assuring the independence of the line exit, it is preferable to apply a liquid seal mechanism. In that case, the discharge opening of the liquid seal mechanism is necessary at a lower level than the liquid level in the liquid seal mechanism of the separation member so as the condensed liquid to be collected to the return line and to be discharged into the catalyst slurry layer. It is also preferable that the lower end of the return line is positioned inside of the catalyst slurry layer to let the catalyst slurry layer function as the liquid seal mechanism. In any way, it is preferable that the return of condensed liquid to the catalyst slurry layer is done by a natural flow down motion.

The sections in the reactor other than the above-described sections may be similar with those in conventional reactors. The raw material gas charge line is connected to the bottom or near the bottom of the reactor. The reaction product gas discharge line is connected to the top or near the top of the reactor. For the case of dimethyl ether-synthesis reactor, the recycle line of a mixed gas of carbon monoxide and hydrogen separated from the reaction product gas is connected to either the passage of the raw material gas charge line or the reactor directly. In addition, instruments such as a pressure gauge and a thermometer, and if necessary, an agitator and an auxiliary raw material charge line may be mounted to the reactor.

A dimethyl ether-synthesis apparatus that contains the dimethyl ether-synthesis reactor using the reactor according to the present invention may be the same configuration with conventional apparatus except that the condenser to condense the medium oil and the gas-liquid separator to separate the condensed medium oil are not required. That is, at the exit of the reactor, a series of equipment are connected in a sequent order of: a methanol-water separator which cools the reaction product gas to condense methanol and water to separate them from the gas phase; a non-reacted gas separator which further cools the gas to condense dimethyl ether and carbon dioxide, thus separating thereof from carbon monoxide and hydrogen; and a $CO_2$ separator which separates dimethyl ether and carbon dioxide from the condensed mixture. Each of the methanol-water separator and the non-reacted gas separator may further be divided into a condenser and a gas-liquid separator. Alternatively, methanol, water, dimethyl ether, and carbon dioxide may be condensed or solidified together, then carbon monoxide and hydrogen may be separated, followed by separating dimethyl ether from the condensed solid.

Figure 11:
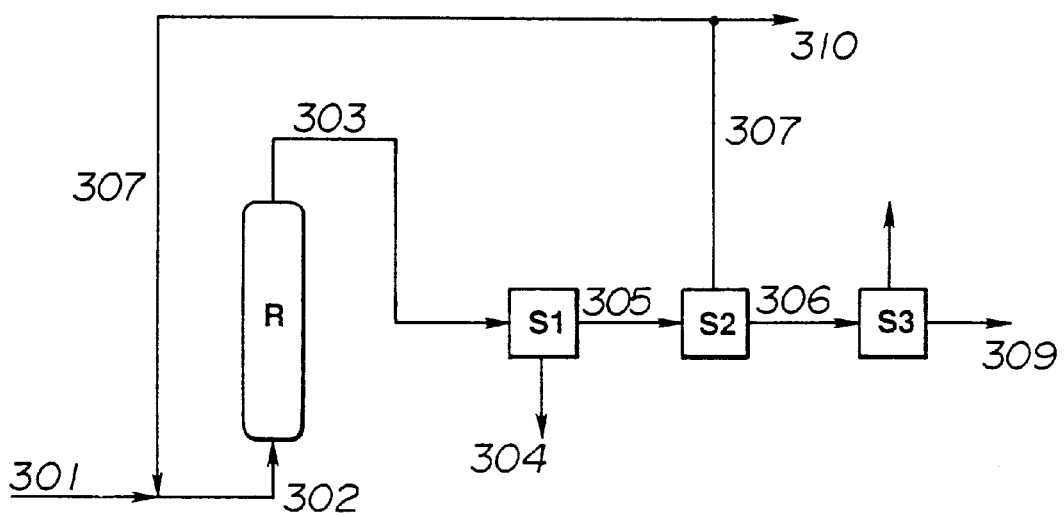
FIG. 11 is a schematic representation showing the apparatus for producing dimethyl ether into which the reactor of the embodiment 8 is installed.

FIG. 11 shows an example of the apparatus implementing the above-described alternative method. The apparatus comprises a reactor R, a methanol-water separator S1, a non-reacted gas separator S2, and a $CO_2$ separator S3. A raw material gas charge line 302 is connected to the bottom of the reactor R. To the raw material gas charge line 302, a make-up (fresh) gas line 301 through which the fresh raw material gas is supplied, and a recycle gas line 307 through which the non-reacted CO and $H_2$ gases are supplied are connected. A reaction product gas line 303 to discharge the reaction products connects the top of the reactor R to the inlet of the methanol-water separator S1. A methanol-water line 304 is connected to the exit of methanol-water separator S1. A reaction product gas line 305 is connected to the exit of reaction products on the methanol-water separator S1. The other end of the reaction product gas line 305 is connected to the inlet of the non-reacted gas separator S2. The other end of the recycle gas line 7 is connected to the exit of non-reacted gas on the non-reacted gas separator S2. The recycle gas line 7 is provided with a branched purge line 310 to draw out a part of the gas. A DME, $CO_2$ line 306 is connected to the exit of DME, $CO_2$ on the non-reacted gas separator S2. The other end of the DME, $CO_2$ line 306 is connected to the $CO_2$ separator S3. A $CO_2$ line 308 is connected to the $CO_2$ exit on the $CO_2$ separator S3. A DME line 309 is connected to the exit of DME on the $CO_2$ separator S3.

When the reactor according to the present invention is used as the dimethyl ether-synthesis reactor, a mixed catalyst of a methanol synthesis catalyst and a methanol-dehydration catalyst is used as the dimethyl ether-synthesis catalyst to fill the reactor, and, if needed, a water gas shift catalyst is further added to the mixed catalyst system.

An applicable kind of medium oil is arbitrary if only the medium oil maintains liquid state under the reaction condition. In the case of dimethyl ether synthesis, for example, the medium oil may be hydrocarbons of aliphatic, aromatic, and alicyclic groups, alcohol, ether, ester, ketone, halide, or their mixture. Alternatively, gas oil after removing sulfur ingredients, vacuum gas oil, high boiling point distillates of coal tar after treated by hydrogenation, Fischer-Tropsch synthesis oil, and high boiling point food oil are also applicable as the medium oil. The amount of catalyst in the solvent depends on the kind of solvent and the reaction condition. Normally, a preferable range of the catalyst is from 1 to 50 wt. % to the amount of solvent, more preferably in a range of from 2 to 30 wt. %.

For the case of a dimethyl ether synthesis reaction, a preferable reaction temperature in the reactor is in a range of from 150 to 400° C., and particularly preferable in a range of from 250 to 350° C. The reaction temperature below 150° C. and above 400° C. degrades the conversion of carbon monoxide. A preferable reaction pressure is in a range of from 10 to 300 $kg/cm^2$, more preferably in a range of from 15 to 150 $kg/cm^2$, and most preferably in a range of from 20 to 70 $kg/cm^2$. The reaction pressure below 10 $kg/cm^2$ results in a low conversion of carbon monoxide, and that above 300 $kg/cm^2$ requires special design of reactor and is uneconomical because of the need of large amount of energy for pressurizing the system. A preferable space velocity (charge rate of mixed gas per 1 kg of catalyst under standard condition) is in a range of from 100 to 50000 l/kg·h, and particularly preferable from 500 to 30000 l/kg·h. The space velocity above 50000 l/kg·h degrades the conversion of carbon monoxide, and that below 100 l/kg·h is uneconomical because of the need of an excessively large reactor.

EXAMPLE

Figure 9:
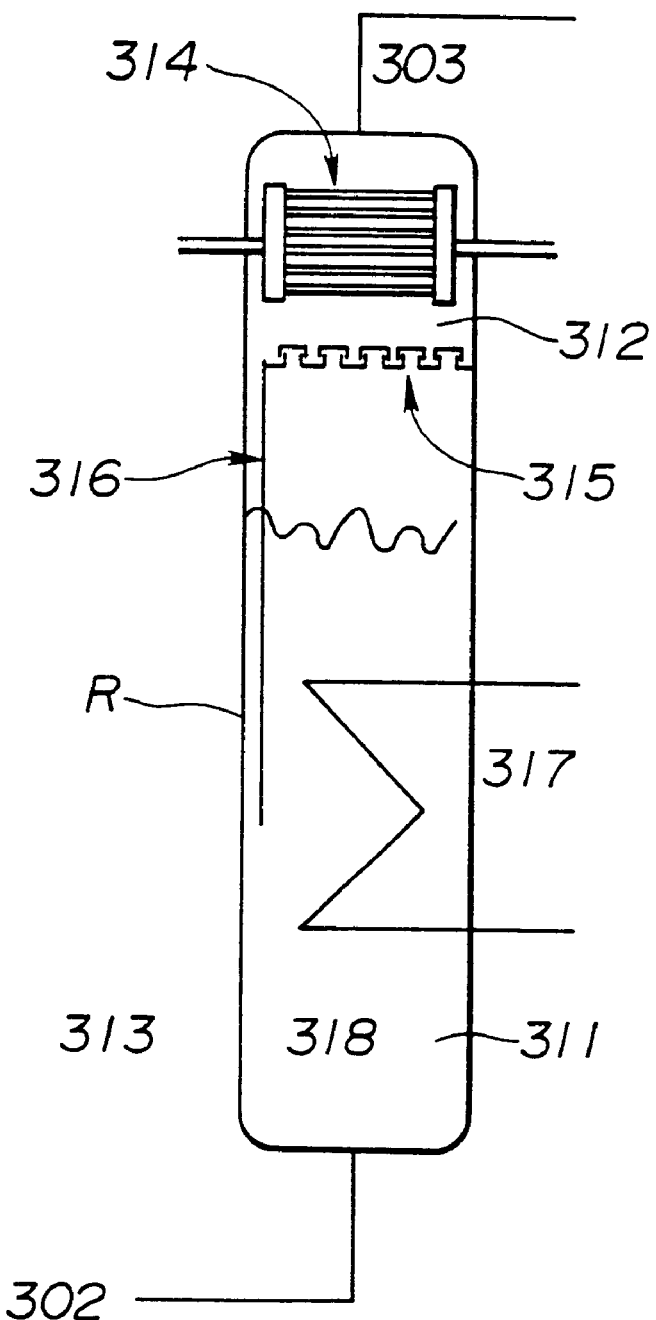
FIG. 9 is a schematic side view of a reactor of the embodiment 8.
Figure 10:
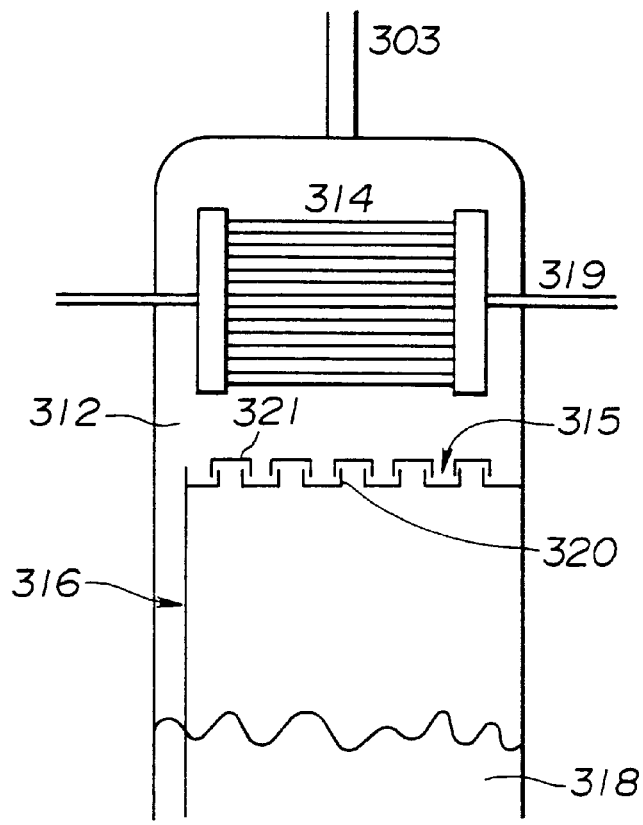
FIG. 10 is a part-enlarged view of the reactor of FIG. 9.

FIG. 9 shows the structure of reactor as an example according to the present invention. FIG. 10 shows a partial-enlarged view of the upper portion of the reactor.

The body 313 of the reactor R is in a cylindrical shape. A slurry-bed chamber 311 located at the lower part of the body 313 is filled with a catalyst slurry 318. A heat transfer tube 317 is located in the catalyst slurry phase 318 to remove reaction heat. The reactor body 313 is extended upward, and a condensation chamber 312 at the upper portion of the body 313 contains a multi-tube condenser 314 to condense a medium oil, to which condenser 314 a coolant pipe 319 is connected. The condensation chamber 312 and the slurry-bed chamber 311 are separated from each other by a bubble-cap plate 315. The bubble-cap plate 315 has a structure of a plate with multiple short-pipes 320 penetrating therethrough, with a cap 321 on each of the short pipes 320. In an operating state, the medium oil condensed in the condenser 314 falls dropwise onto the plate to be held thereon, which hold-up fills the gap between the short pipe 320 and the cap 321 to function as a liquid seal. A downcomer 316 is located at one side of the plate 315 to return the condensed medium oil to the catalyst slurry layer 318, and the lower end of the downcomer enters into the catalyst slurry layer 318. A raw material gas line 302 is connected to the bottom of the reactor body 313, and a reaction product gas line 303 is connected to the top thereof. A mixed powder of a methanol synthesis catalyst and a methanol-dehydration catalyst is used in the reactor R, and further, at need, powder of a water gas shift catalyst is mixed thereinto. To the catalyst, a high boiling point medium oil such as n-cetane having 286.8° C. of boiling point and 226 of molecular weight is added to form a slurry of the catalyst with liquid. Concentration of the slurry is at around 20 wt. %. A raw material gas such as synthesis gas containing carbon monoxide and hydrogen as main raw materials is supplied through the pipe 302 into the lower part of the reactor R. The raw material gas reacts during the ascending passage through the catalyst slurry layer 318, and the reacted products are discharged from the pipe 303 at top of the reactor R. The reaction is carried out under a condition of 30 kg/cm$^2$G, 280° C., and W/F=6 kg·cat/CO·kg·mole of raw material gas charge rate (W/F is the ratio of the weight of catalyst to the charge rate of raw material carbon monoxide). Since the dimethyl ether synthesis is a significantly exothermic reaction, a heat transfer tube 317 is located in the catalyst slurry layer 318 within the reactor R to remove the reaction heat. During the operation of the reactor, the upper side of the bubble-cap plate 315 is covered with the cooled and condensed high boiling point medium oil. As a result, a part of the vapor of high boiling point medium oil came from lower section of the reactor is caught by the liquid high boiling point medium oil during the passage of crossing the bubble-cap plate 315. The vapor of high boiling point medium oil which was not caught by the liquid on the bubble-cap plate 315 is cooled in the condenser 314 to fall onto the bubble-cap plate 315 as droplets. The high boiling point medium oil thus efficiently cooled and separated from the reaction product gas returns to the catalyst slurry layer passing through a downcomer 316 which connects the bubble-cap plate 315 with the catalyst slurry layer 318 and which immerses the bottom end thereof into the catalyst slurry layer 318. A low temperature heating medium may be introduced to the condenser 314 to cool the ascended vapor of high boiling point medium oil, or a low temperature process fluid such as the raw material gas may be used as the cooling medium.

If no cooling for recovering the medium oil is applied, the n-cetane concentration in the discharged gas reaches to as high as 2 to 4 mole %. Since the volume of discharged gas is large, the net amount of discharged n-cetane becomes large.

According to the present invention, there is no need to recycle the discharged medium oil to the reactor, and the operation of the reactor is stabilized. In particular, the structure of reaction product gas line of the reactor becomes significantly simple, and there is no need to apply high pressure pump nor as-liquid separator for recycling the medium oil.

Embodiment 9

Regarding the dimethyl ether-synthesis reaction in a slurry-bed reactor, six molar volumes of raw material gas changes to two molar volumes of reaction product gas when the reaction proceeded to 100%. Since, however, actual one-pass conversion of the raw material gas is at about 50%, six molar volumes of raw material gas changes to one fold of volume of reaction product gas, and three fold of volume of reaction gas is discharged from the reactor as the non-reacted gas. That is, the gas volume reduces to one third.

According to the present invention, the principle of the above-described gas volume reduction is utilized. In concrete terms, the internal of the reactor is divided into two sections: upper reaction tank and lower reaction tank. The lower tank firstly makes the non-reacted recycle gas react, thus reducing the volume of non-reacted gas flowing through the reactor. Then, the gas is added to the make up gas to let these gases react in the upper tank.

Therefore, according to the present invention, a reactor with a smaller inner diameter maintains the flow condition in the reactor at a uniform bubble-tower state owing to the reduction of the gas volume by reacting the non-reacted recycle gas firstly in the reactor.

The reactor according to the present invention is a slurry-bed reactor which is divided into two tanks: upper tank and lower tank. Each of the upper tank and the lower tank has a slurry-bed holding section and an upper space. The slurry-bed holding section, or the catalyst slurry holding section, is provided with a cooling mechanism to remove reaction heat. The boundary of the upper tank and the lower tank is necessary to have a structure that the slurry in the upper tank does not flow down into the lower tank and that the reaction product gas in the lower tank enters into the slurry-bed in the upper tank. A structure having the necessary functions is to open a connection hole on the bottom plate of the upper tank while mounting a check valve to the connection hole to prevent the slurry in the upper tank from flowing down into the lower tank. An alternative structure is to install a connection pipe between the upper space of the lower tank and the upper tank, which connection pipe is extended to a height that the slurry in the upper tank does not flow down into the lower tank even when the reaction stops. The latter structure may further be assured its function by installing an open/close valve to the connection pipe. The connection pipe may be installed either inside or outside of the tanks. For both structures, there is no need for the separation wall between the upper tank and the lower tank to have pressure-resistant performance as a high pressure vessel because the pressure difference between these tanks is within several atm.

The raw material gas feed pipe through which the fresh raw material gas is charged to the reactor may be connected to either of the upper space of the lower tank or the slurry-bed of the upper tank.

Other sections than those described above may be similar with those in conventional reactors, and instruments such as a pressure gauge and a thermometer, and if necessary, an agitator and an auxiliary raw material charge line may be mounted to the reactor.

A dimethyl ether-synthesis apparatus that contains the dimethyl ether-synthesis reactor using a reactor according to the present invention may be the same configuration with conventional apparatus. That is, at the exit of the reactor, a series of equipment are connected in a sequent order of: a condenser to condense the medium oil vaporized from the reactor; a gas-liquid separator to separate the condensed medium oil; a methanol-water separator which cools the reaction product gas to condense methanol and water to separate them from the gas phase; a non-reacted gas separator which further cools the gas to condense dimethyl ether and carbon dioxide, thus separating thereof from carbon monoxide and hydrogen; and a $CO_2$ separator which separates dimethyl ether and carbon dioxide from the condensed mixture. Each of the methanol-water separator and the non-reacted gas separator may further be divided into a condenser and a gas-liquid separator. Alternatively, methanol, water, dimethyl ether, and carbon dioxide may be condensed or solidified together, then carbon monoxide and hydrogen may be separated, followed by separating dimethyl ether from the condensed solid.

Figure 14:
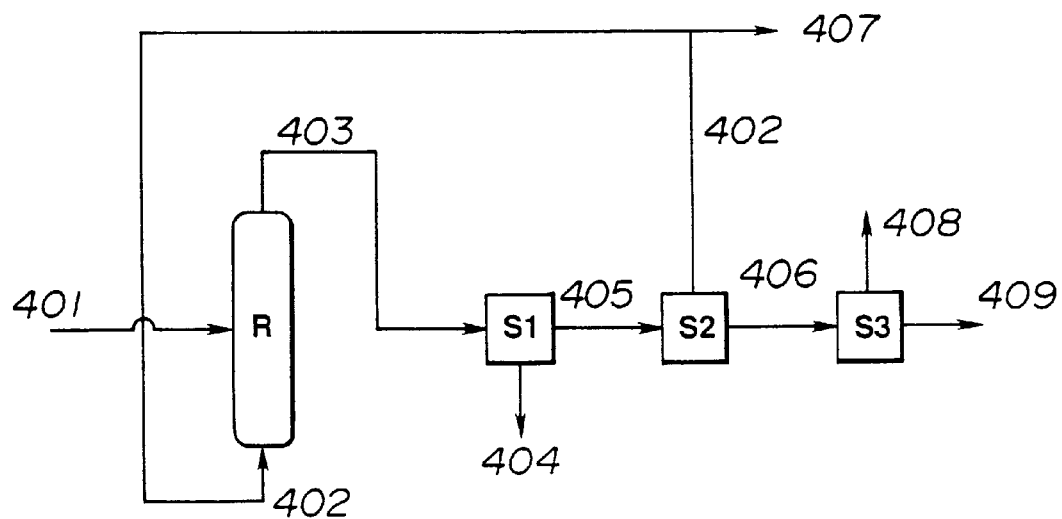
FIG. 14 is a schematic representation showing the apparatus for producing dimethyl ether into which the reactor of the embodiment 9 is installed.

FIG. 14 shows an example of the apparatus implementing the above-described method. The apparatus comprises a reactor R, a methanol-water separator S1, a non-reacted gas separator S2, and a $CO_2$ separator S3. A make up (fresh) gas line 401 is connected to the center part of the reactor R. A recycle gas line 402 through which the non-reacted CO and H2 are recycled to charge is connected to the bottom of the reactor. A reaction product gas line 403 to discharge the reaction products connects the top of the reactor R to the inlet of the methanol-water separator S1, (the condenser for medium oil and the gas-liquid separator therefor are installed upstream of the methanol-water separator S1, if needed). A methanol-water line 404 is connected to the exit of methanol-water on the methanol-water separator S1. A reaction product gas line 405 is connected to the exit of reaction products on the methanol-water separator S1. The other end of the reaction product gas line 405 is connected to the inlet of the non-reacted gas separator S2. The other end of the recycle gas line 402 is connected to the exit of non-reacted gas on the non-reacted gas separator S2. The recycle gas line 402 is provided with a branched purge line 407 to withdraw a part of the gas. A DME, $CO_2$ line 406 is connected to the exit of DME, $CO_2$ on the non-reacted gas separator S2. Other end of the DME, $CO_2$ line 406 is connected to the $CO_2$ separator S3. A $CO_2$ line 408 is connected to the $CO_2$ exit on the $CO_2$ separator S3. A DME line 409 is connected to the exit of DME on the $CO_2$ separator S3.

A mixed catalyst of a methanol synthesis catalyst and a methanol-dehydration catalyst is used as the dimethyl ether-synthesis catalyst to fill the reactor according to the present invention, and, if needed, a water gas shift catalyst is added to the mixed catalyst system.

An applicable kind of medium oil is arbitrary if only the medium oil maintains liquid state under the reaction condition. In the case of dimethyl ether synthesis, for example, the medium oil may be hydrocarbons of aliphatic, aromatic, and alicyclic groups, alcohol, ether, ester, ketone, halide, or their mixture. Alternatively, gas oil after removing sulfur ingredients, vacuum gas oil, high boiling point distillates of coal tar after treated by hydrogenation, Fischer-Tropsch synthesis oil, and high boiling point food oil are also applicable as the medium oil. The amount of catalyst in the solvent depends on the kind of solvent and the reaction condition. Normally, a preferable range of the catalyst is from 1 to 50 wt. % to the amount of solvent, more preferably in a range of from 2 to 30 wt. %.

For the case of dimethyl ether synthesis reaction, a preferable reaction temperature in the reactor is in a range of from 150 to 400° C., and particularly preferable in a range of from 250 to 350° C. The reaction temperature below 150° C. and above 400° C. degrades the conversion of carbon monoxide. A preferable reaction pressure is in a range of from 10 to 300 kg/cm², more preferably in a range of from 15 to 150 kg/cm², and most preferably in a range of from 20 to 70 kg/cm². The reaction pressure below 10 kg/cm² results in a low conversion of carbon monoxide, and that above 300 kg/cm² requires special design of reactor and is uneconomical because of the need of large amount of energy for pressurizing the system. A preferable space velocity (charge rate of mixed gas per 1 kg of catalyst under standard condition) is in a range of from 100 to 50000 l/kg·h, and particularly preferable from 500 to 30000 l/kg·h. The space velocity above 50000 l/kg·h degrades the conversion of carbon monoxide, and that below 100 l/kg·h is uneconomical because of the need of an excessively large reactor.

EXAMPLE

Figure 12:
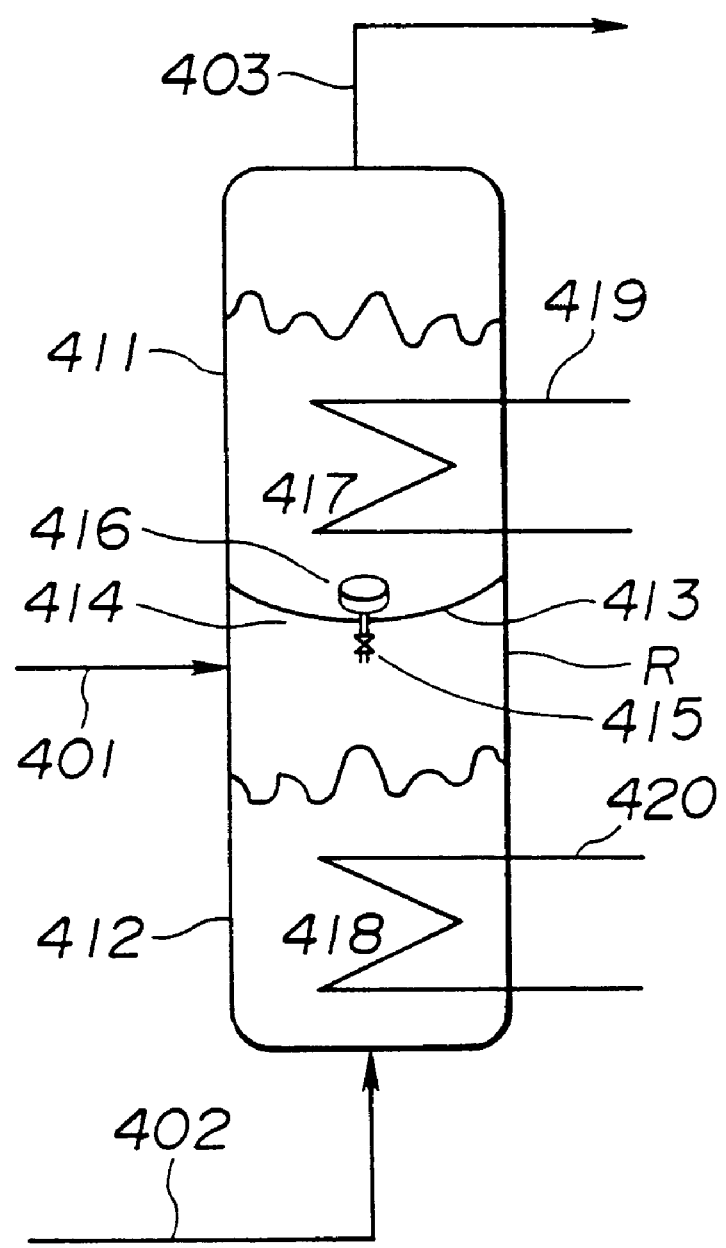
FIG. 12 is a schematic side view of a reactor of the embodiment 9.

FIG. 12 shows the structure of reactor as an example according to the present invention.

A reactor R is totally in a longitudinal cylindrical shape. Inside of the reactor is divided into an upper tank 411 and a lower tank 412 with a dish-shaped separation plate 413. At the center of the separation plate 413, a connection pipe 414 having a check valve 415 is located to connect the upper tank with the lower tank while preventing the slurry-bed of the upper tank from flowing down. A gas distributor 416 is located at the upper end of the connection pipe 414 in the upper tank. Both of the upper tank 411 and the lower tank 412 are filled with slurry-bed. Each of the slurry-beds 417, 418 has a heat transfer tube 419, 420, respectively, to remove the reaction heat.

According to the reactor, only the non-reacted gas is pumped to the bottom of the lower tank 412 of the reactor through a recycle gas line 402. The raw material make up gas is supplied through a make up gas line 401 into the upper space of the catalyst slurry layer 418 in the lower tank 412 of the reactor to mix with the reaction product gas coming from the non-reacted recycle gas line. The mixed gas then passes through the connection pipe 414 in the reactor, enters the upper tank 411 of the reactor, and after reacted, flows out from the reaction product gas line 403.

When the reactor treats 1000 Nm³/min. of make up raw material gas and four fold of volume of non-reacted recycle gas at an one-pass conversion of 50% under a condition of 30 kg/cm²G of reaction pressure and 300° C. of reaction temperature, the non-reacted recycle gas of 4000 Nm³/min. reduces its volume in the lower tank 412 of the reactor to 4000×2/3=2667 Nm³/min. As a result, the gas is mixed with the make up raw material gas of 1000 Nm³/min. to become a volume of 3667 Nm³/min. That is, the upper tank 411 to which the maximum volume of gas enters in the reactor accepts the gas of 3667 Nm³/min.

Under a sustained state of internal flow condition of the reactor, the cross sectional area of the reactor is proportional to the maximum gas flow rate. Since the cross sectional area of the reactor is proportional the square of the inner diameter thereof, the inner diameter of the reactor is proportional to the square root of the maximum gas flow rate. Accordingly, the example calculation given above results in about 10.4 m of inner diameter of reactor to treat the gas of 5000 Nm³/min. compared with about 12.2 m of inner diameter in conventional reactor for the same gas flow rate. The difference is a significant merit for fabricating a commercial large scale reactor.

Figure 13:
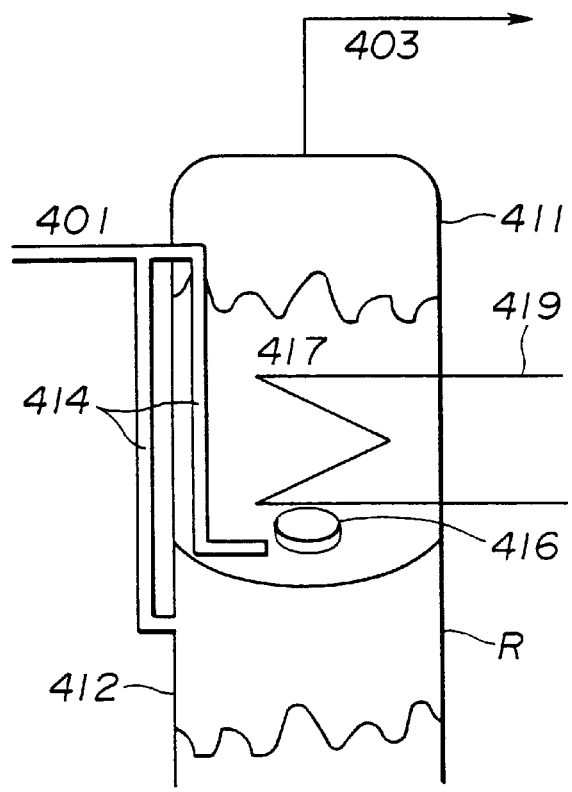
FIG. 13 is a schematic side view of another reactor of the embodiment 9.

FIG. 13 is another example of reactor according to the present invention. For the reactor R, a connection pipe 414 comes out from the upper space of the lower tank to outside of the reactor, and extends upward to the upper level than the surface of the slurry-bed 417 in the upper tank 411, then connects with a make up gas line 401 to enter the upper tank 411 down into the bottom section of the upper tank 411, and finally joins to a gas distributor 416. The other structure is the same with that of FIG. 12.

A reactor according to the present invention synthesizes dimethyl ether by charging a raw material gas such as coal gasified gas and synthesis gas produced from natural gas, containing carbon monoxide and hydrogen as the main raw materials, to a slurry reactor in which a reaction catalyst is suspended in a medium oil. By decreasing the maximum gas flow rate inside of the reactor relative to the same throughput, the reactor size is decreased, thus reducing the fabrication cost of the high pressure reactor, which cost occupies a large portion of the investment cost in a high pressure process.

Embodiment 10

Synthesis of dimethyl ether proceeds following the three equilibrium reactions shown below.

(1) (Methanol synthesis reaction)
(2) (Dehydration reaction)
(3) (Shift reaction)

In the case that the reaction (1) is solely carried out, the reaction is what is called the methanol synthesis reaction. The methanol synthesis reaction has a limitation of equilibrium, and a high pressure (80 to 120 kg/cm$^2$) is necessary to obtain a target conversion. In the single stage process, however, the reaction (2) which is significantly superior in terms of equilibrium successively proceeds within the same reactor to consume the methanol as the reaction product, so the inferior reaction equilibrium of reaction (1) is compensated. As a result, the dimethyl ether synthesis becomes very easy compared with conventional methanol synthesis process. In other words, the single stage process increases the conversion of $CO/H_2$.

The reaction products comprise non-reacted CO and $H_2$, reaction products methanol, dimethyl ether, and $CO_2$, and slight amount of byproducts such as alkane. Since the composition depends on the reaction rate and equilibrium of each of the reactions (1) through (3), the single stage process cannot increase the amount of solely a target product. In particular, methanol as an intermediate is unavoidably left in the reaction products.

The reaction rate in each reaction is controlled by changing the ratio of methanol synthesis catalyst, dehydration catalyst, and shift catalyst. Thus the composition of the reaction products is controlled. Since, however, these three types of reactions proceed simultaneously and since all of these three reactions are equilibrium reactions, the control has a limitation owing to the limit of equilibrium. With that type of reaction system and under a normal reaction condition, it is very difficult to attain the selectivity of dimethyl ether over 95% (in the products excluding $CO_2$).

The difficulty is described below referring to a thermodynamic calculation.

Figure 15:
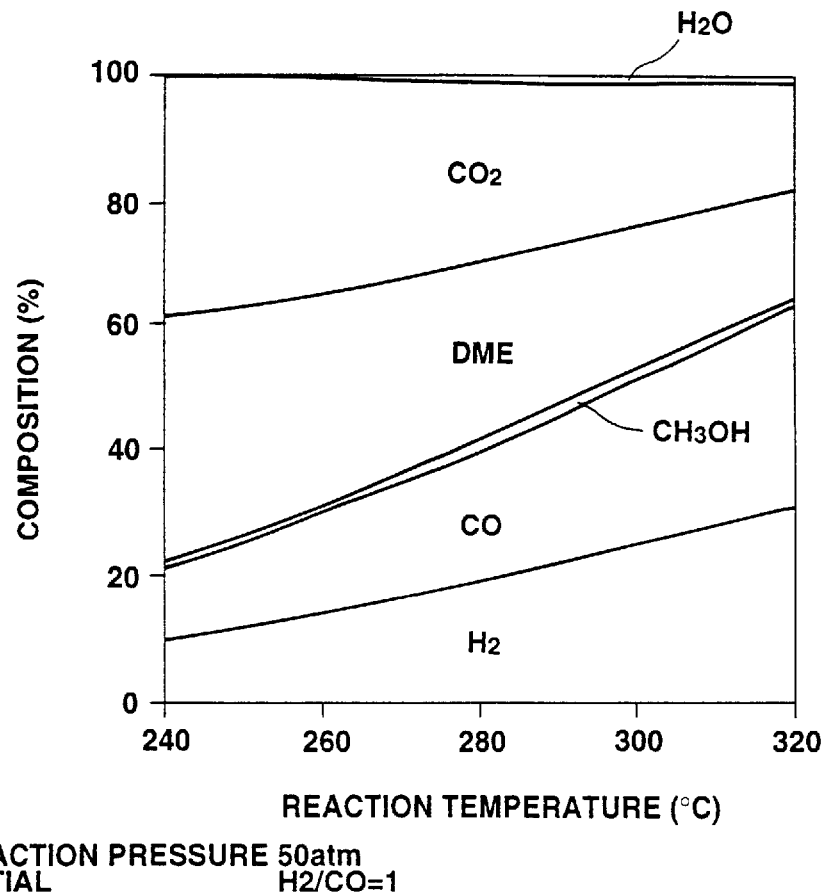
FIG. 15 is a graph showing reaction equilibria of $H_2$, CO, methanol, $CO_2$, and $H_2O$.

FIG. 15 shows reaction equilibria of $H_2$, CO, methanol, $CO_2$, and water, on the basis of reactions (1), (2), and (3). For instance, under a condition of 300° C. of reaction temperature, 50 atm of reaction pressure, and 1 of initial $CO/H_2$ ratio, the selectivity of dimethyl ether (starting material of CO, carbon molar basis, excluding $CO_2$) at the reaction equilibrium is 98%. Establishing a reaction equilibrium is, however, impossible in actual process, and the selectivity of dimethyl ether becomes significantly lower level than the calculated value owing to the presence of methanol as an intermediate. In a state of a lower temperature than the above example, for instance at 240° C. of reaction temperature, 50 atm of reaction pressure, and 1 of initial $CO/H_2$ ratio, the selectivity of dimethyl ether at a reaction equilibrium becomes 99% which is somewhat higher than that in the above example. Under the condition, however, the rate of methanol-synthesis reaction (1) is low and actually the reaction equilibrium is never established.

To cope with the situation, the method according to the present invention uses a mixture of a methanol synthesis catalyst, a dehydration catalyst or a dehydration and a shift catalyst in the first stage reaction to yield crude dimethyl ether, and uses a dehydration and/or a shift catalyst in the second stage reaction to convert most of the remaining methanol into dimethyl ether, thus attains a final high selectivity of dimethyl ether.

When the second stag,e reaction uses only a dehydration and/or a shift catalyst without applying a methanol synthesis catalyst, solely the dehydration and/or shift reaction proceeds and only these reactions approach the equilibrium state. In a reaction system where no methanol synthesis catalyst exists, no additional methanol yields, and the remained methanol is converted into dimethyl ether, so the selectivity of dimethyl ether increases.

The above-described process, however, needs an additional reactor, which increases investment cost. In this respect, the inventors developed a reactor having two separated sections therein using the similarity of reaction condition (temperature and pressure) for both the first stage reaction and the second stage reaction. The reactor is described below.

The present invention was completed on the basis of the above-described concept, and the above-described object is attained by providing a reaction apparatus for synthesizing dimethyl ether which comprises: a reactor for synthesizing dimethyl ether from a mixed gas as a raw material gas containing carbon monoxide and either or both of hydrogen and water vapor, or from a mixed gas as a raw material gas containing carbon monoxide, either or both of hydrogen and water vapor, and carbon dioxide, which reactor comprises a lower stage holding a catalyst slurry and an upper stage holding a catalyst fixed bed; a raw material gas feed pipe connected to the lower stage; a reaction product gas discharge pipe connected to the upper stage.

The lower stage of the reactor according to the present invention is a vertical type slurry-bed reactor which holds a catalyst slurry and has a heat exchanger therein to remove reaction heat.

The catalyst used in the slurry-bed is a combination of known methanol synthesis catalyst, known dehydration catalyst, and known water gas shift catalyst. An applicable methanol synthesis catalyst includes common industrial catalysts for methanol synthesis, such as those of copper oxide-zinc oxide system, zinc oxide-chromium oxide system, copper oxide-zinc oxide/chromium oxide system, copper oxide-zinc oxide/alumina system. Examples of dehydration catalyst are acid-base catalyst such as γ-alumina, silica, silica-alumina, and zeolite. Examples of the metallic oxide ingredient in zeolite are oxide of alkali metal such as sodium and potassium, and oxide of alkali earth metal such as calcium and magnesium. Examples of water gas shift catalyst are copper oxide-zinc oxide system, copper oxide-chromium oxide-zinc oxide system, and iron oxide-chromium oxide system. Since methanol synthesis catalyst has a strong activity as a shift catalyst, it can substitute for the water gas shift catalyst. A copper oxide supported by alumina is applicable as a dehydration catalyst and also as a water gas shift catalyst.

The mixing ratio of the above-described methanol synthesis catalyst, dehydration catalyst, and water gas shift catalyst is not specifically limited, and it depends on the kind of each ingredient and reaction condition. Normally the ratio is often in an approximate range of from 0.1 to 5 wt.parts of dehydration catalyst to 1 wt.parts of methanol synthesis catalyst, more preferably in an approximate range of from 0.2 to 2; in an approximate range of from 0.2 to 5 wt.parts of water gas shift catalyst, more preferably in an approximate range of from 0.5 to 3. When the methanol synthesis catalyst substitutes for the water gas shift catalyst, the above-described amount of the water gas shift catalyst is added to the amount of the methanol synthesis catalyst.

The above-described catalyst is used in a powder state. A preferable average particle size is 300 $\mu$m or less, more preferably in an approximate range of from 1 to 200 $\mu$m, and most preferably in an approximate range of from 10 to 150 $\mu$m. To prepare powder of that range of particle size, the catalysts may further be pulverized.

An applicable kind of heating medium oil for dispersing catalyst is arbitrary if only the heating medium oil maintains liquid state under the reaction condition. For example, the heating medium oil may be hydrocarbons of aliphatic, aromatic, and alicyclic groups, alcohol, ether, ester, ketone, halide, or their mixture. Alternatively, gas oil after removing sulfur ingredients, vacuum gas oil, high boiling point distillates of coal tar after being treated by hydrogenation, Fischer-Tropsch synthesis oil, and high boiling point food oil are also applicable as the heating medium oil. The amount of catalyst in the solvent depends on the kind of solvent and the reaction condition. Normally, a preferable range of the catalyst is from 1 to 50 wt. % to the amount of solvent, more preferably in an approximate range of from 10 to 30 wt. %.

A raw material gas is injected from a gas-injection nozzle mounted to the slurry-bed reactor section to make the raw material gas contact with the catalyst. With agitation to mix the slurry in the reactor, the reaction is enhanced. By inserting heat transfer tubes into the reactor, the reaction heat is removed from the reactor. The removed reaction heat may be recovered to be utilized in other applications. Since a slurry-bed reactor is easy for agitation, the reaction heat is uniformly dispersed to the whole reaction system. As a result, hot spots hardly appear, which makes the heat recovery easy. In addition, temperature distribution within the reactor hardly becomes irregular, so the amount of yielded byproducts is small. Furthermore, that type of reactor is easy for charge and withdrawal of catalyst, and easy for start up and stop operation.

As described before, however, a reaction in a slurry-bed unavoidably leave methanol in the reaction system as an intermediate product of the reaction.

To cope with the residual methanol issue, a fixed bed reactor section is installed at the upper part of the reactor to convert the remaining methanol into dimethyl ether. A catalyst applied to the fixed bed reactor contains at least one of dehydration catalyst and dehydration and shift catalyst. As for the dehydration catalyst, one of the above-described groups may be used. For the dehydration and shift catalyst, copper oxide supported by $\gamma$-alumina may be used as a catalyst having both the dehydration activity and the shift activity. The catalyst in the fixed bed needs to be firmly held in the bed and also needs to have a void that allows for a gas to pass freely through the fixed bed. To do this, the catalyst particle size may be granulated to an approximate size ranging from 1 to 20 mm, more preferably from 1.5 to 10 mm. Members such as perforated plate and meshed material are installed at the bottom of the bed, as needed, to support the catalyst particles. The catalyst may be a porous block having lots of throughhole pores.

The ratio of the amount of catalyst in a slurry-bed to that in a fixed bed depends on the activity of the catalyst in each bed. Normally, the weight ratio of the catalyst (slurry bed)/(fixed bed) is in a range of from 1:10 to 10:1, more preferably from 1:5 to 5:1.

The boundary between the upper stage and the lower stage is in an arbitrary state if only gas freely passes therethrough. Entrainment emitted from the lower fluidized catalyst layer is allowed to attach the upper fixed bed.

The raw material gas feed pipe is connected to the lower stage of the reactor to charge the raw material gas into the fluidized catalyst layer. The reaction product gas discharge pipe is connected to the upper stage to let the gas pass through the fixed catalyst bed and exit from the reactor.

Other sections than those described above may be similar with those in conventional reactors, and instruments such as a pressure gauge and a thermometer, and if necessary, an agitator and an auxiliary raw material charge line may be mounted to the reactor.

A dimethyl ether-synthesis apparatus that contains the dimethyl ether-synthesis reactor using the reactor according to the present invention may be the same configuration with a conventional apparatus. That is, at the exit of reactor, a series of equipment are connected in a sequent order of: a condenser to condense the heating medium oil vaporized from the reactor; a gas-liquid separator to separate the condensed heating medium oil; a methanol-water separator which cools the reaction product gas to condense methanol and water to separate them from the gas phase; a non-reacted gas separator which further cools the gas to condense dimethyl ether and carbon dioxide, thus separating thereof from carbon monoxide and hydrogen; and a $CO_2$ separator which separates dimethyl ether and carbon dioxide from the condensed mixture. Each of the methanol-water separator and the non-reacted gas separator may further be divided into a condenser and a gas-liquid separator. Alternatively, methanol, water, dimethyl ether, and carbon dioxide may be condensed or solidified together, then carbon monoxide and hydrogen may be separated, followed by separating dimethyl ether from the condensed solid.

Figure 16:
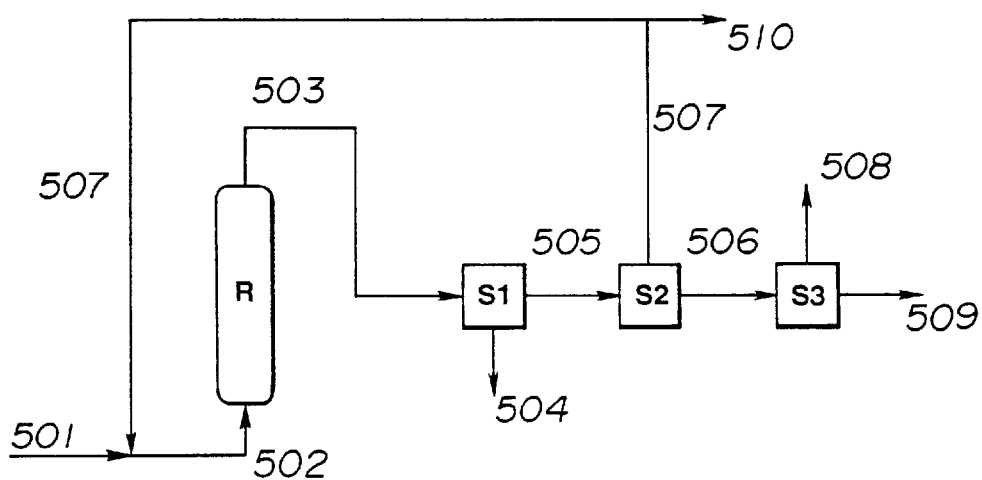
FIG. 16 is a schematic representation showing the apparatus for producing dimethyl ether into which the reactor of the embodiment 10 is installed.

FIG. 16 shows an example of the apparatus implementing the above-described method. The apparatus comprises a reactor R, a methanol-water separator S1, a non-reacted gas separator S2, and a $CO_2$ separator S3. A raw material gas line 502 is connected to the bottom of reactor R. To the raw material gas line 502, a make up (fresh) gas line 501 which supplies fresh raw material gas and a recycle gas line 507 through which the non-reacted CO and H2 are recycled to charge are connected. A reaction product gas line 503 to discharge the reaction products connects the top of reactor R to the inlet of methanol-water separator S1, (a condenser for heating medium oil and a gas-liquid separator therefor are installed upstream of the methanol-water separator S1, at need). A methanol-water line 504 is connected to the exit of methanol-water on the methanol-water separator S1. A reaction product gas line 505 is connected to the exit of reaction products on the methanol-water separator S1. The other end of the reaction product gas line 505 is connected to the inlet of the non-reacted gas separator S2. The other end of the recycle gas line 507 is connected to the exit of non-reacted gas on the non-reacted gas separator S2. The recycle gas line 507 is provided with a branched purge line 510 to withdraw a part of the gas. A DME, $CO_2$, line 506 is connected to the exit of DME, $CO_2$ on the non-reacted gas separator S2. Other end of the DME, $CO_2$ line 6 is connected to the $CO_2$ separator S3. A $CO_2$ line 508 is connected to the $CO_2$ exit on the $CO_2$ separator S3. A DME line 509 is connected to the edit of DME on the $CO_2$ separator S3.

The mixing ratio of hydrogen and carbon monoxide may be in a range of from 20 to 0.1 as $H_2CO$ molar ratio, more preferably in a range of from 10 to 0.2. In the case of a mixed gas with a significantly low ratio of ($H_2CO$), for example, 0.1 or less, or in the case of solely carbon monoxide without containing hydrogen, it is necessary to separately supply steam to conduct the shift reaction in the reactor to convert a part of the carbon monoxide into hydrogen and carbon dioxide. A preferable charge rate of steam is 1 or less to the charge rate of CO. A preferable amount of carbon dioxide yielded from the reaction is 50% or less.

A preferable condition for both the upper and lower stage reactions is the reaction temperature in a range of from 150 to 400° C., particularly in a range of from 200 to 350° C. The reaction temperature below 150° C. and above 400° C. results in a reduction of carbon monoxide conversion. A preferable reaction pressure is in a range of from 10 to 300 $kg/cm^2$, particularly in a range of from 15 to 70 $kg/cm^2$. The reaction pressure below 10 $kg/cm^2$ results in a low conversion of carbon monoxide, and that above 300 $kg/cm^2$ requires a special design of reactor and is uneconomical because of the need of a large amount of energy for pressurizing the system. A preferable space velocity (charge rate of mixed gas per 1 g of catalyst under standard condition) is in a range of from 100 to 50000 l/kg·h, and particularly preferable from 500 to 30000 l/kg·h. The space velocity above 50000 l/kg·h degrades the conversion of carbon monoxide, and that below 100 l/kg·h is uneconomical because of the need of an excessively large reactor.

For the reactor according to the present invention, the use of a combination of methanol synthesis catalyst, dehydration catalyst, and shift catalyst in the first stage reaction increases the conversion of $CO/H_2$ in the raw material gas, and the use of dehydration catalyst and/or shift catalyst in the second stage reaction converts most part of the remained methanol into dimethyl ether, thus the selectivity of dimethyl ether increases. In spite of two stage reaction, the reactor is designed to a compact type configuring two separated sections integrated in a single vessel utilizing almost the same reaction condition (temperature and pressure) for both stages.

Amount of CO gas charged to reactor (Nl/min.):Fin(CO)
Amount of CO gas discharged from reactor:Fout(CO)
Amount of DME gas discharged from reactor:Fout(DME)
Amount of MeOH gas discharged from reactor:Fout(MeHO)
Amount of methane gas discharged from reactor:Fout($CH_4$)

$$(\text{CO conversion}) = \frac{Fin(CO) - Fout(CO)}{Fin(CO)} \times 100 \ (\%)$$

$$(\text{Selectivity of dimethylether}) = \frac{2 \times Fout(DME)}{2 \times Fout(DME) + Fout(MeOH) + Fout(CH_4)}$$

$$(\text{Selectivity of methanol}) = \frac{Fout(MeOH)}{2 \times Fout(DME) + Fout(MeOH) + Fout(CH_4)}$$

EXAMPLE

Catalyst A: CuO—ZnO—$Al_2O_3$ Catalyst

Each of 185 g of copper nitrate ($Cu(NO_3)_2 3H_2O$), 117 g of zinc nitrate ($Zn(NO_3)_2 6H_2O$), and 52 g of aluminum nitrate ($Al(NO_3)_3 9H_2O$) were dissolved into about 1 liter of ion-exchanged water. Separately, about 1.4 kg of sodium carbonate ($Na_2CO_3$) was dissolved into about 1 liter of ion-exchanged water. Both of the solutions were added dropwise to about 3 liters of ion-exchanged water in a stainless steel vessel which was controlled at about 60° C. within about 2 hours. while maintaining the contents to pH 7.0±0.5. Then, the contents were allowed to stand for about 1 hour for aging. When, during the treatment, the pH value went out from a range of pH 7.0±0.5, an aqueous solution of about 1 mole/liter sodium carbonate was added dropwise to keep the range of pH 7.0±0.5. The resultant precipitate was filtered, and the cake was rinsed by ion-exchanged water until nitric acid ion was not detected anymore. After the rinse, the cake was dried at 120° C. for 24 hours, followed by calcining thereof in air at 350° C. for 5 hours to obtain the target catalyst. Analysis of the thus obtained catalyst gave the composition as $CuO:ZnO:Al_2O_3=61:32:7$ (by weight).

Catalyst B: CuO—$Al_2O_3$ catalyst

A 15.7 g of copper acetate ($Cu(CH_3COO)_2 H_2O$) was dissolved into about 200 ml of ion-exchanged water. A 95 g of γ-alumina (N612, Nikki Kagaku Co.) was further added to the mixture. The mixture was then vaporized to dry. The dried material was calcined in air at 450° C. for 4 hours. The calcined material was treated in hydrogen gas stream at 400° C. for 3 hours to obtain a catalyst. Analysis of the catalyst gave the composition as $Cu:Al_2O_3=5:95$ by weight).

Each of the catalyst thus prepared was pulverized in a ball mill to a particle size of 120 μm or less.

The lower stage of the reactor was filled with 5584 ml of n-hexadecane as the heating medium oil, 430 g of the catalyst A, and 215 g of catalyst B: that is, (catalyst A/catalyst B)=2/1, and (catalyst/heating medium oil)=15/100. The upper stage of the reactor was filled solely with 645 g of catalyst B.

(Preliminary Reduction)

Under a condition of 10 $kg/cm^2$ of reactor pressure, 220° C. of reactor temperature, a mixed gas ($H_2/N_2=1/4$) was introduced to the reactor at a flow rate of 10 l/min. for 12 hours to conduct preliminary reduction.

A gas of $H_2/CO=1/1$ was introduced to the reaction system at a flow rate of 18 l/min. to conduct the dimethyl ether synthesis under a condition of 50 $kg/cm^2$G and 260° C. for both the upper and the lower stages. Gas analysis was conducted by gas-chromatography, and the gas flow rate at the exit of reaction system was determined by a gas meter. From the analysis and flow rate determination, CO conversion and selectivity of each reaction product were calculated, (carbon molar basis, excluding $CO_2$). The result showed 41.0% of CO conversion, 95.5% of DME selectivity, 4.4% of methanol selectivity, and 0.1% of methane selectivity.

Comparative Example

Dimethyl ether synthesis was conducted under the same conditions in the preceding Example except that the upper stage of the reactor did not contain catalyst. The result showed 34.0% of CO conversion, 67.1% of DME selectivity, 32.8% of methanol selectivity, and 0.1% of methane selectivity. The DME selectivity was at a low level.

The reactor according to the present invention provides dimethyl ether from carbon monoxide and hydrogen (or water vapor) at a high conversion and high selectivity. As a result, high purity dimethyl ether is obtained from the reaction products, thus allowing mass production of dimethyl ether at a low cost.

What is claimed is:

1. An apparatus for producing dimethyl ether comprising:
   (a) a slurry-bed reactor filled with a dimethyl ether synthesis catalyst and a medium oil therefor, the slurry-bed reactor comprising (i) an upper tank having a reaction product gas discharge pipe to discharge a reaction product gas and (ii) a lower tank having a raw material gas feed pipe and a recirculation pipe for recirculating a non-reacted gas separated from the reaction product gas;

(b) a condenser for condensing a gasified medium oil discharged from the reactor;

(c) an adsorber for removing a catalyst-deactivation ingredient from the medium oil condensed in the condenser;

(d) recycle means for recycling the medium oil to the slurry-bed reactor; and (e) a separation member having a liquid seal mechanism for separating the slurry-bed reactor and the condenser.

2. The apparatus of claim 1, wherein the condenser is mounted on an upperside of the slurry-bed reactor.

3. The apparatus of claim 1, wherein the slurry-bed reactor comprises:

a lower stage which holds a catalyst slurry, the lower stage having a raw material gas feed pipe; and an upper stage which holds a catalyst fixed bed, the upper stage having a product gas discharge pipe.

4. The apparatus of claim 1, wherein the condenser is a heat exchanger.

5. The apparatus of claim 1, wherein the liquid seal mechanism is a bubble-cap plate.

6. The apparatus of claim 1, wherein the upper tank and the lower tank are separated by a dish-shaped separation plate.

7. The apparatus of claim 6, wherein a connection pipe having a check valve is disposed at the center of the separation plate.

8. The apparatus of claim 7, wherein a gas distributor is disposed at an upper end of the connection pipe and in the upper tank.

* * * * *